US012590080B2

(12) United States Patent
Zeng et al.

(10) Patent No.: US 12,590,080 B2
(45) Date of Patent: Mar. 31, 2026

(54) COMPOUNDS

(71) Applicant: PACKINAX PTY LTD, Blackburn (AU)

(72) Inventors: Jun Zeng, Victoria (AU); Mehrdad Nikfarjam, Victoria (AU); Hong He, Victoria (AU)

(73) Assignee: PAKINAX PTY LTD., Victoria (AU)

(*) Notice: Subject to any disclaimer, the term of this patent is extended or adjusted under 35 U.S.C. 154(b) by 548 days.

(21) Appl. No.: 18/002,187

(22) PCT Filed: Jun. 30, 2021

(86) PCT No.: PCT/AU2021/050691
§ 371 (c)(1),
(2) Date: Dec. 16, 2022

(87) PCT Pub. No.: WO2022/000031
PCT Pub. Date: Jan. 6, 2022

(65) Prior Publication Data

US 2023/0242519 A1 Aug. 3, 2023

(30) Foreign Application Priority Data

Jun. 30, 2020 (AU) ................................ 2020902199

(51) Int. Cl.
*C07D 405/04* (2006.01)
*C07D 409/04* (2006.01)

(52) U.S. Cl.
CPC ......... *C07D 405/04* (2013.01); *C07D 409/04* (2013.01)

(58) Field of Classification Search
None
See application file for complete search history.

(56) References Cited

PUBLICATIONS

CAS Reg. No. 837415-88-0 (Year: 2005).*
Murray et al., Small-molecule p21-activated kinase inhibitor PF-3758309 is a potent inhibitor of oncogenic signaling and tumor growth. Proc Natl Acad Sci U S A. May 18, 2010;107(20):9446-51 (Year: 2010).*
Rudolph, J. et al., "Inhibitors of p21-Activated Kinases (PAKs)"; J. Med. Chem. 2015, 58, p. 111-129.
Murray, Brion W., et al. "Small-molecule p21-activated kinase inhibitor PF-3758309 is a potent inhibitor of oncogenic signaling and tumor growth." Proceedings of the National Academy of Sciences 107.20 (2010): 9446-9451; https://doi.org/10.1073/pnas.091186310.

(Continued)

*Primary Examiner* — Jeffrey S Lundgren
(74) *Attorney, Agent, or Firm* — Tarolli, Sundheim, Covell & Tummino LLP

(57) ABSTRACT

Described herein are compounds that are inhibitors of p21-activated kinases (PAKS). In particular, the compounds described herein are demonstrated to be selective PAK4 inhibitors. The compounds described herein are also demonstrated to reduce the expression of key immune checkpoint molecules, such as PD-1 and CHEK2. Also described herein are pharmaceutical compositions containing such compounds, methods for using such compounds in the treatment of cancers, more specifically, the treatment of pancreatic and lung cancers, and to related uses.

20 Claims, 6 Drawing Sheets

(56) References Cited

PUBLICATIONS

Staben, Steven T., et al. "Back pocket flexibility provides group II p21-activated kinase (PAK) selectivity for type I 1/2 kinase inhibitors." Journal of medicinal chemistry 57.3 (2014): 1033-1045; https://doi.org/10.1021/jm401768t.

Applicant: Pakinax PTY Ltd; International Application No. PCT/AU2021/050691 Filed Jun. 30, 2021; PCT International Search Report dated Jul. 26, 2021; 4 pgs.

* cited by examiner

COMPOUNDS

FIELD

The present disclosure relates to compounds that are inhibitors of p21-activated kinases (PAKs). The disclosure also relates to pharmaceutical compositions containing such compounds, methods for using such compounds in the treatment of cancers, more specifically, the treatment of pancreatic and lung cancers, and to related uses.

BACKGROUND

Cancer is the term given to a collection of related diseases in which abnormal cells divide in an uncontrolled manner, such that they invade nearby tissues. Cancer is recognised as a leading cause of death, with the Agency for Research on Cancer estimating 18.1 million new cancer cases, and 9.6 million cancer deaths, in 2018.

The p21-activated kinases (PAKs) are a family of serine/threonine protein kinases with two subgroups: PAK1, PAK2, and PAK3 (subgroup I), and PAK4, PAK5, and PAK6 (subgroup II). Since their discovery in the mid-1990s, the understanding of the regulation and biology of these important signalling proteins has increased tremendously, with the PAKs thought to play a role in cytoskeletal organisation, cellular morphogenesis, and cell survival. As a consequence, the PAKs have been implicated in many diseases, including cancer, infectious diseases, and neurological disorders.

In particular, it is PAKs recognition as being integral to growth factor signalling networks, as well as oncogenic processes that control cell proliferation, cell polarity, invasion and actin cytoskeleton organisation, that implicates them in major, yet varied, roles in the oncogenic processes. To date, a number of cancers have been associated with alterations in the expression and/or activation of PAKs.

Of the PAK family, the PAK4 sub-type is a key downstream effector of the RHO family of GTPases downstream of Ras (Dart and Wells, 2013), and is found to be particularly overexpressed in pancreatic ductal adenocarcinoma (PDAC) cells compared to normal human pancreatic ductal epithelia (Hakoshima, Shimizu, Maesaki, 2003; Himmelman, Hezel et al, 2008; Mahlamaki, Kauraniemi et al, 2004). As a consequence, PAK4 is an attractive therapeutic target in cancers, particularly PDAC cancer, pancreatic cancer, colon cancer, prostate cancer, and lung cancer.

The inhibition of PAKs therefore presents as a useful therapeutic target in the prevention and/or treatment of cancers, and other disorders.

However, few PAK inhibitors with satisfactory kinase selectivity and drug-like properties have been reported to date. There are even fewer reported potent PAK inhibitors that are selective for particular PAK sub-types, including PAK4. There is therefore a need for novel, potent, and/or selective PAK inhibitors.

An emerging field of cancer therapeutics are the immunotherapies. Immunotherapy refers to the treatment of a disease by activating or suppressing the immune system. The T cells of the immune system possess the capacity to selectively recognise and kill pathogens or unhealthy cells, including cancer cells, by orchestrating a coordinated immune response. Many checkpoints ensure that the cells of the immune system do not mistakenly destroy healthy cells during an immune response (known as an autoimmune reaction). Cancer cells can exploit these immune checkpoints as a way to evade immune detection and elimination.

There are numerous immune checkpoint molecules that may provide a target in cancer therapy, including, but not limited to, A2AR, BTLA, CTLA-4, NOX2, TIM-3, and LAG3. To date, these inhibitory checkpoint molecules remain relatively unexplored in cancer therapy.

One such immune checkpoint molecule, the programmed cell death-1 (PD-1) receptor, is expressed on the surface of activated T cells. Its ligands, PD-L1 and PD-L2, are commonly expressed on the surface of dendritic cells or macrophages. PD-1 and PD-L1/PD-L2 belong to the family of immune checkpoint proteins that act as co-inhibitory factors that can halt or limit the development of the T cell response. The PD-1/PD-L1 interaction ensures that the immune system is activated only at the appropriate time in order to minimise the possibility of chronic autoimmune inflammation.

PD-L1 is commonly over-expressed on tumor cells or on non-transformed cells in the tumor microenvironment. PD-L1 expressed on the tumor cells binds to PD-1 receptors on the activated T cells, which leads to the inhibition of the cytotoxic T cells. These deactivated T cells remain inhibited in the tumor microenvironment. Accordingly, by blocking immune checkpoint proteins, including PD-1 and PD-L1, it has been found that the immune system can overcome cancer's ability to resist the immune responses and stimulate the body's own mechanisms to remain effective in its defense against cancer.

Examples of approved cancer therapies which act via blocking the interaction between PD-1 and PD-L1 include the antibody products Keytruda® (pembrolizumab) and Opdivo® (nivolumab).

While immune checkpoint inhibition through PD-1 blockade has brought significant treatment benefits, the currently approved agents have limitations, and the potential for development of resistance may be a major obstacle to long-term treatment with those agents.

Accordingly, there remains a need for new therapies for treating cancer.

SUMMARY

The subject matter of the present disclosure is predicated in part on the surprising discovery that compounds of Formula (I) are inhibitors of PAK and have antiproliferative effects.

The examples also support that the compounds decrease expression of the immune checkpoint molecules, PD-L1 and CHEK2, and so find application in immunotherapy.

The compounds described herein are PAK4 inhibitors, and are also considered to be molecules that may modulate the tumour microenvironment to enhance the efficacy of immune checkpoint inhibitors, and may bring significant improvement to the immune checkpoint blockade when used in combination therapy.

Accordingly, in one aspect there is provided a compound of Formula (I) or a salt thereof:

Formula (I)

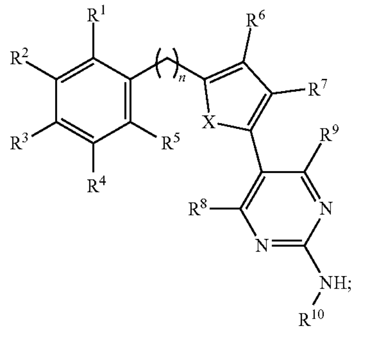

wherein $R^1$, $R^3$, and $R^5$ are each independently selected from the group consisting of hydrogen, halogen, —$C_{1-6}$alkyl, —O—$C_{1-6}$alkyl, —$C_{1-6}$haloalkyl, —O—$C_{1-6}$haloalkyl, —$C_{2-6}$alkenyl, —$C_{2-6}$alkynyl, $C_{3-10}$carbocyclyl, 3-10 membered heterocyclyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$, wherein said alkyl, alkenyl, alkynyl, carbocyclyl or heterocyclyl may be unsubstituted or substituted with one or more substituents each independently selected from the group consisting of halogen, $C_{1-4}$alkyl, O—$C_{1-4}$alkyl, $C_{1-4}$haloalkyl, —O—$C_{1-4}$haloalkyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$;

$R^2$ and $R^4$ are each independently selected from the group consisting of hydrogen, halogen, —$C_{1-4}$alkyl, —O—$C_{1-4}$alkyl, —$C_{1-4}$haloalkyl, and —O—$C_{1-4}$haloalkyl;

n is an integer of from 0 to 2;

X is S, O, or NH;

$R^6$ is selected from the group consisting of hydrogen, halogen, —$C_{1-4}$alkyl, —O—$C_{1-4}$alkyl, —$C_{1-4}$haloalkyl, and —O—$C_{1-4}$haloalkyl;

$R^7$ is selected from the group consisting of hydrogen, halogen, —CN, —$C_{1-6}$alkyl, —$C_{3-10}$carbocyclyl, —$C_{3-10}$heterocyclyl, —O—$C_{1-6}$alkyl, —O—$C_{3-10}$carbocyclyl, —O-(3-10 membered heterocyclyl), —NH($C_{1-6}$alkyl), —N($C_{1-6}$alkyl)$_2$, —NH—$C_{3-10}$carbocyclyl, —N($C_{1-4}$alkyl)-$C_{6-10}$carbocyclyl, —NH-(3-10 membered heterocyclyl), —N($C_{1-4}$alkyl)-(3-10 membered heterocyclyl), —C(O)—$C_{1-4}$alkyl, —C(O)—$C_{3-10}$carbocyclyl, —C(O)-(3-10 membered heterocyclyl), and —C(O)N($C_{1-4}$alkyl)$_2$, wherein said alkyl, carbocyclyl or heterocyclyl may be unsubstituted or substituted with up to two substituents each independently selected from the group consisting of —$C_{1-4}$alkyl, oxo, halogen, and —$C_{1-4}$haloalkyl;

$R^8$ is selected from the group consisting of hydrogen, —$C_{1-8}$alkyl, —O—$C_{1-8}$alkyl, —$C_{1-4}$alkylene-$R^{13}$, —O—$C_{1-4}$alkylene-$R^{13}$, and —$OR^{13}$;

$R^9$ is selected from the group consisting of hydrogen and halogen;

$R^{10}$ is selected from the group consisting of hydrogen, —$C_{1-6}$alkyl, —$C_{1-6}$haloalkyl, —$C_{6-10}$aryl, —$R^{14}$, —$C_{1-6}$alkylene-$R^{14}$, —$C_{1-10}$arylene-$R^{14}$, —NH—$C_{1-6}$alkyl-$R^{14}$, and —NH—C(O)—$C_{1-6}$alkyl-$R^{14}$;

wherein said aryl or arylene may optionally be substituted with one or two substituents each independently selected from the group consisting of —$C_{1-4}$alkyl, halogen, and —$C_{1-4}$haloalkyl;

if present, each $R^{11}$ and $R^{12}$ is independently selected from the group consisting of hydrogen, —$C_{1-6}$alkyl, —$C_{3-10}$carbocyclyl, and 3-10 membered heterocyclyl;

if present, $R^{13}$ is selected from the group consisting of hydrogen, —$C_{1-6}$alkyl, halogen, —CN, —$C_{3-10}$carbocyclyl, 3-10 membered heterocyclyl, —O—$C_{1-6}$alkyl, —O—$C_{3-10}$carbocyclyl, —O-(3-10 membered heterocyclyl), —NH($C_{1-6}$alkyl), —N($C_{1-6}$alkyl)$_2$, —NH—$C_{3-10}$carbocyclyl, —N($C_{1-4}$alkyl)-$C_{6-10}$carbocyclyl, —NH-(3-10 membered heterocyclyl), —N($C_{1-4}$alkyl)-(3-10 membered heterocyclyl), —C(O)—$C_{1-4}$alkyl, —C(O)—$C_{3-10}$carbocyclyl, —C(O)-(3-10 membered heterocyclyl), and —C(O)N($C_{1-4}$alkyl)$_2$, wherein said alkyl, carbocyclyl or heterocyclyl may be unsubstituted or substituted with up to two substituents each independently selected from the group consisting of —$C_{1-4}$alkyl, oxo, halogen and —$C_{1-4}$haloalkyl; and if present, $R^{14}$ is selected from the group consisting of —$NH_2$, —$C_{3-10}$heterocyclyl, —O—$C_{3-10}$heterocyclyl, —NH—$C_{3-10}$heterocyclyl, and —N(Me)-$C_{3-10}$heterocyclyl;

wherein said heterocyclyl may be unsubstituted or substituted with up to three substituents each independently selected from —$C_{1-4}$alkyl, oxo, halogen and —$C_{1-4}$haloalkyl.

In some embodiments, $R^1$ and $R^5$ are each independently selected from the group consisting of halogen and —$C_{1-4}$alkyl. In some embodiments, $R^1$ and $R^5$ are each halogen. In some embodiments, $R^1$ and $R^5$ are each chlorine. In some embodiments, $R^3$ is selected from the group consisting of $C_{1-6}$alkyl, —O—$C_{1-6}$alkyl, phenyl, or 5-6 membered heteroaromatic, said phenyl or heteroaromatic being unsubstituted or substituted by one or two $C_{1-4}$ alkyl groups. In some embodiments, $R^3$ is —O—$C_{1-4}$alkyl. In some embodiments, $R^3$ is —O—$CH_3$. In some embodiments, $R^2$ and $R^4$ are each hydrogen. In some embodiments, $R^6$ is selected from the group consisting of hydrogen, halogen, $C_{1-4}$alkyl and —O—$C_{1-4}$alkyl. In some embodiments, $R^6$ is hydrogen. In some embodiments, $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl. In some embodiments, $R^7$ is hydrogen. In some embodiments, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH$C_{3-10}$heterocyclyl. In some embodiments, $R^8$ is hydrogen. In some embodiments, $R^9$ is hydrogen. In some embodiments, $R^8$ and $R^9$ are each hydrogen. In some embodiments, $R^{10}$ is selected from the group consisting of hydrogen, $C_{1-6}$alkyl, $C_{1-6}$haloalkyl, $C_{6-10}$aryl, —$R^{14}$, —$C_{1-6}$alkylene-$R^{14}$ and —$C_{6-10}$arylene-$R^{14}$, wherein said aryl or arylene may optionally be substituted with one or two substituents each independently selected from the group consisting of $C_{1-4}$alkyl, halogen and $C_{1-4}$haloalkyl. In some embodiments, $R^{10}$ is —$CH_3$. In some embodiments, n is 1. In some embodiments, X is O. In some embodiments, n is 1 and X is O. In some embodiments, $R^1$ and $R^5$ are chlorine, $R^3$ is —$OCH_3$, and $R^2$ and $R^4$ are each hydrogen.

In some embodiments, the compound of Formula (I) is (Ia)

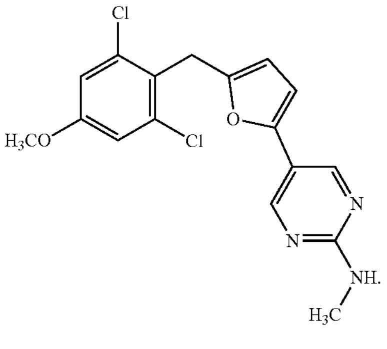

In some embodiments, the compound of Formula (I) is (Ic)

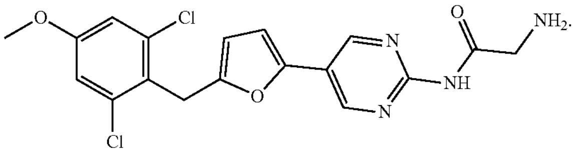

In some embodiments, the compound of Formula (I) is (Id)

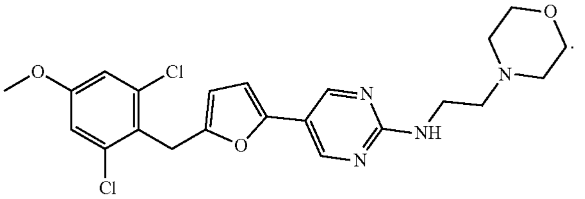

In some embodiments, n is 0. In some embodiments, X is S. In some embodiments, n is 0 and X is S. In some embodiments, $R^1$ and $R^5$ are chlorine, $R^3$ is $—OCH_3$, and $R^2$ and $R^4$ are each hydrogen.

In some embodiments, the compound of Formula (I) is (Ib)

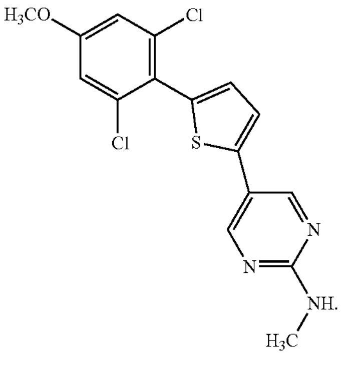

In a further aspect, there is provided a pharmaceutical composition comprising the compound or salt as described herein, and a pharmaceutically acceptable excipient. In some embodiments, the pharmaceutical composition further comprises a therapeutic agent. In some embodiments, the further therapeutic agent is an anti-cancer agent. In some embodiments, the further therapeutic agent is selected from the group consisting of ipilimumab, bevacizumab, pemetrexed, platinum chemotherapeutics, a taxane, etoposide, and gemcitabine. In some embodiments, the pharmaceutical composition further comprising a checkpoint inhibitor. In some embodiments, the checkpoint inhibitor is a PD-1 or PD-L1 inhibitor. In some embodiments, the checkpoint inhibitor is selected from the group consisting of nivolumab, pembrolizumab, pidilizumab, AMP-224, TSR-042, BMS-936559, BMS-1001, BMS-1166, BGB-A317, atezolizumab, avelumab, cemiplimab, and durvalumab. In some embodiments, the checkpoint inhibitor is a CHEK2 inhibitor. In some embodiments, the checkpoint inhibitor is selected from the group consisting of CCT241533 and BML-277.

In a further aspect, there is provided a compound or salt as described herein, or a pharmaceutical composition as described herein, for use in therapy. In some embodiments, the compound or salt as described herein, or a pharmaceutical composition as described herein is for use in immunotherapy. In some embodiments, the compound or salt as described herein, or a pharmaceutical composition as described herein is for use in preventing or treating cancer.

In a further aspect, there is provided a method of reducing PD-L1 expression, comprising contacting a compound or salt as described herein, or a pharmaceutical composition as described herein, with a PAK enzyme.

In a further aspect, there is provided a method of decreasing the binding of PD-L1 to PD-1, comprising contacting a compound or salt as described herein, or a pharmaceutical composition as described herein, with a PAK enzyme.

In a further aspect, there is provided a method of decreasing CHEK2 expression, comprising contacting a compound or salt as described herein, or a pharmaceutical composition as described herein, with a PAK enzyme.

In a further aspect, there is provided a method of inhibiting CHEK2, comprising contacting a compound or salt as described herein, or a pharmaceutical composition as described herein, with a PAK enzyme.

In a further aspect, there is provided a method of preventing or treating cancer in a subject, comprising administering an effective amount of the compound or salt as described herein, or a pharmaceutical composition as described herein, to the subject.

In a further aspect, there is provided a method of immunotherapy, comprising administering an effective amount of the compound or salt as described herein, or a pharmaceutical composition as described herein, to the subject.

In a further aspect, there is provided use of a compound or salt as described herein, in the preparation of a medicament for use in immunotherapy.

In a further aspect, there is provided use of a compound or salt as described herein, in the preparation of a medicament for use in preventing or treating cancer. In some embodiments, the compound or salt, or pharmaceutical composition, is administered in combination with a further therapeutic agent. In some embodiments, the further therapeutic agent is an anti-cancer agent. In some embodiments, the further therapeutic agent is selected from the group consisting of ipilimumab, bevacizumab, pemetrexed, platinum chemotherapeutics, a taxane, etoposide, and gemcitabine. In some embodiments, the compound or salt, or pharmaceutical composition, further comprises a checkpoint inhibitor. In some embodiments, the checkpoint inhibitor is a PD-1 or PDL-1 inhibitor. In some embodiments, the checkpoint inhibitor is selected from the group consisting of nivolumab, pembrolizumab, pidilizumab, AMP-224, TSR-042, BMS-936559, BMS-1001, BMS-1166, BGB-A317, atezolizumab, avelumab, cemiplimab, and durvalumab. In some embodiments, the checkpoint inhibitor is a CHEK2 inhibitor. In some embodiments, the checkpoint inhibitor is selected from the group consisting of CCT241533 and BML-277. In some embodiments, the cancer is selected from the group consisting of melanoma, kidney cancer, bladder cancer, head and neck cancer, Hodgkin's lymphoma, pancreatic cancer, breast cancer, gastric cancer, glioma, hepatocellular cancer, cholangiocarcinoma, lung cancer, ovarian cancer, osteosarcoma, oesophageal squamous cell cancer, colon cancer, prostate cancer, colorectal cancer, brain glioblastoma, liver cancer, and bile duct cancer. In some embodiments, the cancer is selected from the group consisting of melanoma, kidney cancer, bladder cancer, head and neck cancer, Hodgkin's lymphoma, and lung cancer. In some embodiments, the cancer is selected from the group consisting of pancreatic cancer, breast cancer, gastric cancer, glioma, hepatocellular cancer, cholangiocarcinoma, lung cancer, ovarian cancer, osteosarcoma, oesophageal squamous cell cancer, colon cancer, and prostate cancer.

BRIEF DESCRIPTION OF THE DRAWINGS

FIG. 7 shows the efficacy of Compound Ia in combination with Gemcitabine.

DESCRIPTION

General Definitions

Figure 1:
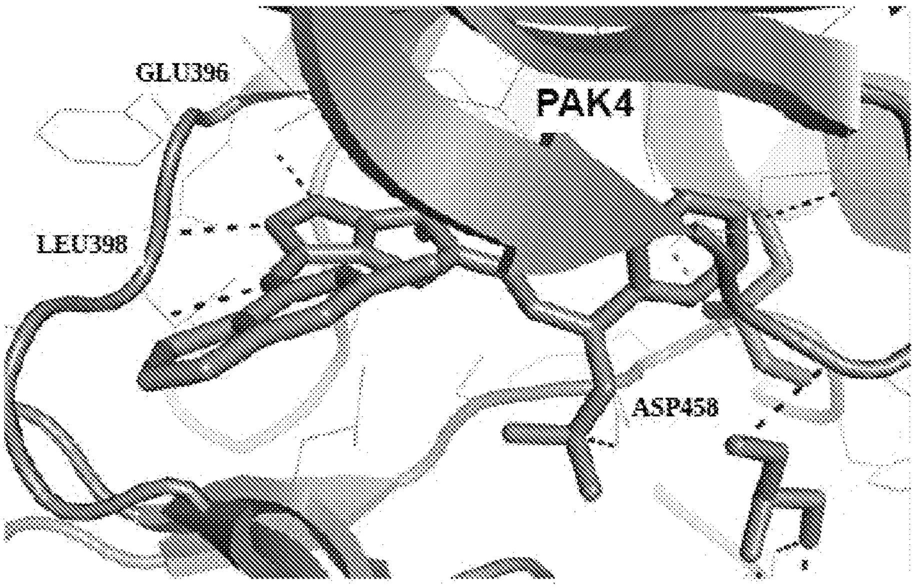
FIG. 1 shows an image of compound PF03758309 bound to PAK4.

Unless specifically defined otherwise, all technical and scientific terms used herein shall be taken to have the same meaning as commonly understood by one of ordinary skill in the art (e.g., chemistry, medicinal chemistry and the like).

As used herein, the term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, of the designated value.

As used herein, singular forms "a", "an" and "the" include plural aspects, unless the context clearly indicates otherwise.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "subject" refers to any organism susceptible to a disease or condition. For example, the subject can be a mammal, primate, livestock (e.g., sheep, cow, horse, pig), companion animal (e.g., dog, cat), or laboratory animal (e.g., mouse, rabbit, rat, guinea pig, hamster). In one example, the subject is a mammal. In one embodiment, the subject is human. In one embodiment, the disease or condition is cancer.

As used herein, the term "treating" includes alleviation of the symptoms associated with a specific disorder or condition and eliminating said symptoms. For example, as used herein, the term "treating cancer" refers to alleviating the symptoms associated with cancer and eliminating said symptoms. In one embodiment, the term "treating cancer" refers to a reduction in cancerous tumour size. In one embodiment, the term "treating cancer" refers to an increase in progression-free survival.

As used herein, the term "prevention" includes prophylaxis of the specific disorder or condition. For example, as used herein, the term "preventing cancer" refers to preventing the onset or duration of the symptoms associated with cancer. In one example, the term "preventing cancer" refers to slowing or halting the progression of the cancer. In one example, the term "preventing cancer" refers to slowing or preventing metastasis.

As would be understood by the person skilled in the art, a compound of Formula (I) or salt thereof would be administered in a therapeutically effective amount. The term "therapeutically effective amount", as used herein, refers to a compound of Formula (I) or salt thereof being administered in an amount sufficient to alleviate or prevent to some extent one or more of the symptoms of the disorder or condition being treated. The result can be the reduction and/or alleviation of the signs, symptoms, or causes of a disease or condition, or any other desired alteration of a biological system. In one embodiment, the term "therapeutically effective amount" refers to a compound of Formula (I) or salt thereof being administered in an amount sufficient to result in a reduction of symptoms associated with cancer. In one embodiment, the term "therapeutically effective amount" refers to a compound of Formula (I) or salt thereof being administered in an amount sufficient to result in a reduction in cancerous tumour size. The term, an "effective amount", as used herein, refers to an amount of a compound of Formula (I) or salt thereof effective to achieve a desired pharmacologic effect or therapeutic improvement without undue adverse side effects or to achieve a desired pharmacologic effect or therapeutic improvement with a reduced side effect profile. By way of example only, therapeutically effective amounts may be determined by routine experimentation, including but not limited to a dose escalation clinical trial. The term "therapeutically effective amount" includes, for example, a prophylactically effective amount. In one embodiment, a prophylactically effective amount is an amount sufficient to prevent cancer. It is understood that "an effective amount" or "a therapeutically effective amount" can vary from subject to subject, due to variation in metabolism of the compound and any of age, weight, general condition of the subject, the condition being treated, the severity of the condition being treated, and the judgment of the prescribing physician. Thus, it is not always possible to specify an exact "effective amount". However, an appropriate "effective amount" in any individual case may be determined by one of ordinary skill in the art using routine experimentation. Where more than one therapeutic agent is used in combination, a "therapeutically effective amount" of each therapeutic agent can refer to an amount of the therapeutic agent that would be therapeutically effective when used on its own, or may refer to a reduced amount that is therapeutically effective by virtue of its combination with one or more additional therapeutic agents.

The compounds of the present disclosure may contain chiral (asymmetric) centers or the molecule as a whole may be chiral. The individual stereoisomers (enantiomers and diastereoisomers) and mixtures of these are within the scope of the present invention.

The following definitions apply to the terms as used throughout this specification, unless otherwise limited in specific instances.

As used herein, the term "halogen" means fluorine, chorine, bromine, or iodine.

As used herein, the term "alkyl" encompasses both straight chain (i.e., linear) and branched chain hydrocarbon groups. Examples of alkyl groups include methyl, ethyl, n-propyl, iso-propyl, n-butyl, t-butyl, i-butyl, sec-butyl, pentyl, and hexyl groups. In one example, the alkyl group is of one to six carbon atoms (i.e. $C_{1-6}$alkyl).

As used herein, the term "alkoxy" refers to the group —O-alkyl, where "alkyl" is as described above. Examples of alkoxy groups include methoxy, ethoxy, propoxy, and butoxy groups. In one example, the alkoxy group is of one to six carbon atoms (i.e. —O—$C_{1-6}$alkyl).

As used herein, the term "alkenyl" refers to both straight and branched chain unsaturated hydrocarbon groups with at least one carbon-carbon double bond. Examples of alkenyl groups include ethenyl, propenyl, butenyl, pentenyl, and hexenyl groups. In one example, the alkenyl group is of two to six carbon atoms (i.e. $C_{2-6}$alkenyl).

As used herein, the term "alkynyl" refers to both straight and branched chain unsaturated hydrocarbon groups with at least one carbon-carbon triple bond. Examples of alkynyl groups include ethynyl, propynyl, butynyl, pentynyl, and hexynyl groups. In one example, the alkynyl group is of two to six carbon atoms (i.e. $C_{2-6}$alkynyl).

As used herein, the term "haloalkyl" refers to an alkyl group having at least one halogen substituent, where "alkyl" and "halogen" are as described above. Similarly, the term "dihaloalkyl" means an alkyl group having two halogen substituents, and the term "trihaloalkyl" means an alkyl group having three halogen substituents. Examples of haloalkyl groups include fluoromethyl, chloromethyl, bromomethyl, iodomethyl, fluoropropyl, and fluorobutyl groups. Examples of dihaloalkyl groups include difluoromethyl and difluoroethyl groups. Examples of trihaloalkyl groups include trifluoromethyl and trifluoroethyl groups. In one example, the haloalkyl group is of one to six carbon atoms (i.e. $C_{1-6}$haloalkyl).

As used herein, the term "oxyhaloalkyl" refers to the group —O-haloalkyl, where "haloalkyl" is as described above. Examples of —O-haloalkoxy groups include —O-fluoromethyl, —O— chloromethyl, —O-bromomethyl, —O-iodomethyl, —O-fluoropropyl, and —O-fluorobutyl groups. In one example, the oxyhaloalkyl group is of one to six carbon atoms (i.e. —O—$C_{1-6}$haloalkyl).

As used herein, the term "carbocyclyl" refers to an aromatic or non-aromatic cyclic group of carbon atoms. A carbocyclyl group may, for example, be monocyclic or polycyclic (i.e. bicyclic, tricyclic). A polycyclic carbocyclyl group may contain fused rings. In one example, the carbocyclyl group is of three to ten carbon atoms (i.e. $C_{3-10}$carbocyclyl).

Examples of monocyclic non-aromatic carbocyclyl groups include cyclopropyl, cyclobutyl, cyclopentyl, cyclopentenyl, cyclohexyl, cyclohexenyl, cycloheptyl, and cyclooctyl groups. Aromatic carbocyclyl groups include phenyl and napthalenyl.

As used herein, the term "heterocyclyl" refers to an aromatic or non-aromatic cyclic group which is analogous to a carbocyclic group, but in which from one to three of the carbon atoms is/are replaced by one or more heteroatoms independently selected from nitrogen, oxygen, or sulfur. A heterocyclyl group may, for example, be monocyclic or polycyclic (e.g. bicyclic). A polycyclic heterocyclyl may for example contain fused rings. In a bicyclic heterocyclyl group there may be one or more heteroatoms in each ring, or heteroatoms only in one of the rings. A heteroatom may be N, O, or S. Heterocyclyl groups containing a suitable nitrogen atom include the corresponding N-oxides. In one example, the heterocyclyl group is of three to ten atoms (i.e. 3-10-membered heterocyclyl). Examples of monocyclic non-aromatic heterocyclyl groups include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl. Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl, and benzoazepanyl. Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl. Examples of bicyclic aromatic heterocyclyl groups (also referred to as bicyclic heteroaryl groups) include quinoxalinyl, quinazolinul, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridyl, pyridopyrimidinyl, isoquinolinyl, and benzohydroxazole.

The present disclosure relates to compounds of Formula (I) and salts thereof. Salts may be formed in the case of embodiments of the compound of Formula (I) which contain a suitable acidic or basic group. Suitable salts of the compound of Formula (I) include those formed with organic or inorganic acids or bases. As used herein, the phrase "pharmaceutically acceptable salt" refers to pharmaceutically acceptable organic or inorganic salts. Exemplary acid addition salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Exemplary base addition salts include, but are not limited to, ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion. It will also be appreciated that nonpharmaceutically acceptable salts also fall within the scope of the present disclosure since these may be useful as intermediates in the preparation of pharmaceutically acceptable salts or may be useful during storage or transport.

Those skilled in the art of organic and/or medicinal chemistry will appreciate that many organic compounds can form complexes with solvents in which they are reacted or from which they are precipitated or crystallized. These complexes are known as "solvates". For example, a complex with water is known as a "hydrate". As used herein, the phrase "pharmaceutically acceptable solvate" or "solvate" refer to an association of one or more solvent molecules and a compound of the present disclosure. Examples of solvents that form pharmaceutically acceptable solvates include, but are not limited to, water, isopropanol, ethanol, methanol, DMSO, ethyl acetate, acetic acid, and ethanolamine. It will be understood that the present disclosure encompasses solvated forms, including hydrates, of the compounds of formula (I) and salts thereof.

Those skilled in the art of organic and/or medicinal chemistry will appreciate that the compounds of Formula (I) and salts thereof may be present in amorphous form, or in a crystalline form. It will be understood that the present disclosure encompasses all forms and polymorphs of the compounds of Formula (I) and salts thereof.

Compounds of Formula (I)

In one aspect, there is provided a compound of Formula (I) or a salt thereof:

Formula (I)

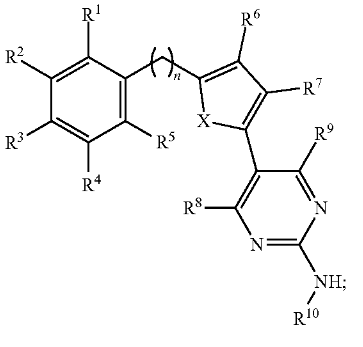

wherein $R^1$, $R^3$, and $R^5$ are each independently selected from the group consisting of hydrogen, halogen, $C_{1-6}$alkyl, —O—$C_{1-6}$alkyl, $C_{1-6}$haloalkyl, —O—$C_{1-6}$haloalkyl, $C_{2-6}$alkenyl, $C_{2-6}$alkynyl, $C_{3-10}$carbocyclyl, 3-10 membered heterocyclyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$, wherein said alkyl, alkenyl, alkynyl, carbocyclyl or heterocyclyl may be unsubstituted or substituted with one or more substituents each independently selected from the group consisting of halogen, $C_{1-4}$alkyl, O—$C_{1-4}$alkyl, $C_{1-4}$haloalkyl, —O—$C_{1-4}$haloalkyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$;

$R^2$ and $R^4$ are each independently selected from the group consisting of hydrogen, halogen, $C_{1-4}$alkyl, —O—$C_{1-4}$alkyl, $C_{1-4}$haloalkyl and —O—$C_{1-4}$haloalkyl;

n is an integer of from 0 to 2;

X is S, O, or NH;

$R^6$ is selected from the group consisting of hydrogen, halogen, $C_{1-4}$alkyl, —O—$C_{1-4}$alkyl, $C_{1-4}$haloalkyl and —O—$C_{1-4}$haloalkyl;

$R^7$ is selected from the group consisting of hydrogen, halogen, —CN, —$C_{1-6}$alkyl, $C_{3-10}$carbocyclyl, $C_{3-10}$heterocyclyl, —O—$C_{1-6}$alkyl, —O—$C_{3-10}$carbocyclyl, —O-(3-10 membered heterocyclyl), —NH($C_{1-6}$alkyl), —N($C_{1-6}$alkyl)$_2$, —NH—$C_{3-10}$carbocyclyl, —N($C_{1-4}$alkyl)-$C_{1-10}$carbocyclyl, —NH-(3-10 membered heterocyclyl), —N($C_{1-4}$alkyl)-(3-10 membered heterocyclyl), —C(O)—$C_{1-4}$alkyl, —C(O)—$C_{3-10}$carbocyclyl, —C(O)-(3-10 membered heterocyclyl), and —C(O)N($C_{1-4}$alkyl)$_2$, wherein said alkyl, carbocyclyl or heterocyclyl may be unsubstituted or substituted with up to two substituents each independently selected from the group consisting of $C_{1-4}$alkyl, oxo, halogen and $C_{1-4}$haloalkyl;

$R^8$ is selected from the group consisting of hydrogen, —$C_{1-8}$alkyl, —O—$C_{1-8}$alkyl, —$C_{1-4}$alkylene-$R^{13}$, —O—$C_{1-4}$alkylene-$R^{13}$ and —O—$R^{13}$;

$R^9$ is selected from the group consisting of hydrogen and halogen;

$R^{10}$ is selected from the group consisting of hydrogen, $C_{1-6}$alkyl, $C_{1-6}$haloalkyl, $C_{6-10}$aryl, —$R^{14}$, —$C_{1-6}$alkylene-$R^{14}$, —$C_{6-10}$arylene-$R^{14}$, —NH—$C_{1-6}$alkyl-$R^{14'}$ and —NH—C(O)—$C_{1-6}$alkyl-$R^{14}$;

wherein said aryl or arylene may optionally be substituted with one or two substituents each independently selected from the group consisting of $C_{1-4}$alkyl, halogen and $C_{1-4}$haloalkyl;

if present, each $R^{11}$ and $R^{12}$ is independently selected from the group consisting of hydrogen, $C_{1-6}$alkyl, $C_{3-10}$carbocyclyl, and 3-10 membered heterocyclyl;

if present, $R^{13}$ is selected from the group consisting of hydrogen, —$C_{1-6}$alkyl, halogen, —CN, $C_{3-10}$carbocyclyl, 3-10 membered heterocyclyl, —O—$C_{1-6}$alkyl, —O—$C_{3-10}$carbocyclyl, —O-(3-10 membered heterocyclyl), —NH($C_{1-6}$alkyl), —N($C_{1-6}$alkyl)$_2$, —NH—$C_{3-10}$carbocyclyl, —N($C_{1-4}$alkyl)-$C_{6-10}$carbocyclyl, —NH-(3-10 membered heterocyclyl), —N($C_{1-4}$alkyl)-(3-10 membered heterocyclyl), —C(O)—$C_{1-4}$alkyl, —C(O)—$C_{3-10}$carbocyclyl, —C(O)-(3-10 membered heterocyclyl), and —C(O)N($C_{1-4}$alkyl)$_2$, wherein said alkyl, carbocyclyl or heterocyclyl may be unsubstituted or substituted with up to two substituents each independently selected from the group consisting of $C_{1-4}$alkyl, oxo, halogen and $C_{1-4}$haloalkyl; and if present, $R^{14}$ is selected from the group consisting of —$NH_2$, $C_{3-10}$heterocyclyl, —O—$C_{3-10}$heterocyclyl, —NH—$C_{3-10}$heterocyclyl and —N(Me)-$C_{3-10}$heterocyclyl;

wherein said heterocyclyl may be unsubstituted or substituted with up to three substituents each independently selected from $C_{1-4}$alkyl, oxo, halogen and $C_{1-4}$haloalkyl.

$R^1$, $R^3$, and $R^5$ of Formula (I) are each independently selected from the group consisting of hydrogen, halogen, $C_{1-6}$alkyl, —O—$C_{1-6}$alkyl, $C_{1-6}$haloalkyl, —O—$C_{1-6}$haloalkyl, $C_{2-6}$alkenyl, $C_{2-6}$alkynyl, $C_{3-10}$carbocyclyl, 3-10 membered heterocyclyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$, wherein said alkyl, alkenyl, alkynyl, carbocyclyl or heterocyclyl may be unsubstituted or substituted with one or more substituents each independently selected from the group consisting of halogen, $C_{1-4}$alkyl, O—$C_{1-4}$alkyl, $C_{1-4}$haloalkyl, —O—$C_{1-4}$haloalkyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$. That is, $R^1$, $R^3$ and $R^5$ may each be the same, or independently different substituents, as described above.

In some embodiments, $R^1$, $R^3$ and $R^5$ of Formula (I) are each independently selected from the group consisting of hydrogen, halogen, $C_{1-6}$alkyl, —O—$C_{1-6}$alkyl, $C_{1-6}$haloalkyl, —O—$C_{1-6}$haloalkyl. In some embodiments, $R^1$, $R^3$ and $R^5$ are each independently selected from the group consisting of halogen, $C_{1-6}$alkyl, —O—$C_{1-6}$alkyl. In some embodiments, $R^1$, $R^3$ and $R^5$ are each independently selected from the group consisting of halogen and —O—$C_{1-6}$alkyl. In some embodiments, $R^1$ is halogen. In some embodiments, $R^1$ is chlorine. In some embodiments, $R^5$ is halogen. In some embodiments, $R^5$ is chlorine. In some embodiments, $R^3$ is methoxy. In some embodiments, $R^3$ is selected from the group consisting of $C_{1-6}$alkyl, —O—$C_{1-6}$alkyl, phenyl, or 5-6 membered heteroaromatic, said phenyl or heteroaromatic being unsubstituted or substituted by one or two $C_{1-4}$ alkyl groups.

In some embodiments, $R^1$ is halogen, $R^3$ is —O—$C_{1-6}$alkyl, and $R^5$ is halogen. In some embodiments, $R^1$ is chlorine, $R^3$ is methoxy, and $R^5$ is chlorine.

$R^2$ and $R^4$ of Formula (I) are each independently selected from the group consisting of hydrogen, halogen, $C_{1-4}$alkyl, —O—$C_{1-4}$alkyl, $C_{1-4}$haloalkyl and —O—$C_{1-4}$haloalkyl. That is, $R^2$ and $R^4$ of Formula (I) may each be the same, or independently different substituents, as described above. In some embodiments, $R^2$ and $R^4$ are each independently selected from the group consisting of hydrogen, halogen, and —O—$C_{1-4}$alkyl. In some embodiments, $R^2$ and $R^4$ are each independently selected from the group consisting of hydrogen and halogen. In some embodiments, $R^2$ is hydrogen. In some embodiments, $R^4$ is hydrogen. In some embodiments, $R^2$ is hydrogen and $R^4$ is hydrogen.

In some embodiments, $R^2$ is hydrogen, $R^4$ is hydrogen, and $R^1$, $R^3$ and $R^5$ are each independently selected from the group consisting of hydrogen, halogen, $C_{1-6}$alkyl, —O—$C_{1-6}$alkyl, $C_{1-6}$haloalkyl, —O—$C_{1-6}$haloalkyl. In some embodiments, $R^2$ is hydrogen, $R^4$ is hydrogen, and $R^1$, $R^3$ and $R^5$ are each independently selected from the group consisting of halogen, $C_{1-6}$alkyl, —$OC_{1-6}$alkyl. In some embodiments, $R^2$ is hydrogen, $R^4$ is hydrogen, and $R^1$, $R^3$ and $R^5$ are each independently selected from the group consisting of halogen and —O—$C_{1-6}$alkyl. In some embodiments, $R^2$ is hydrogen, $R^4$ is hydrogen, $R^1$ is halogen, $R^3$ is —O—$C_{1-6}$alkyl, and $R^5$ is halogen. In some embodiments, $R^2$ is hydrogen, $R^4$ is hydrogen, $R^1$ is chlorine, $R^3$ is methoxy, and $R^5$ is chlorine.

n is an integer of from 0 to 2. In some embodiments, n is 0. In such an instance where n is 0, it will be understood by the person skilled in the art that the six-membered benzene ring of Formula (I) is directly bonded to the five-membered ring of Formula (I). In some embodiments, n is 1. In such an instance where n is 1, it will be understood by the person skilled in the art that the six-membered benzene ring of Formula (I) is bonded to the five-membered ring of Formula (I) through one carbon atom, e.g. via a —$CH_2$— group. In some embodiments, n is 2. In such an instance where n is 2, it will be understood by the person skilled in the art that the six-membered benzene ring of Formula (I) is bonded to the five-membered ring of Formula (I) through two carbon atoms, e.g. via a —$CH_2CH_2$— group.

X of Formula (I) is S, O, or NH. In some embodiments, X is S. In some embodiments, X is O. In some embodiments, X is NH.

In some embodiments, X is S, O, or NH, and n is 0. In some embodiments, X is S, O, or NH, and n is 1. In some embodiments, X is S, O, or NH, and n is 2. In some embodiments, n is 0 and X is O or S. In some embodiments, n is 1 and X is O or S. In some embodiments, n is 2 and X is O or S. In some embodiments, n is 0, and X is S. In some embodiments, n is 1, and X is O.

$R^6$ of Formula (I) is selected from the group consisting of hydrogen, halogen, $C_{1-4}$alkyl, —O—$C_{1-4}$alkyl, $C_{1-4}$haloalkyl and —O—$C_{1-4}$haloalkyl. In some embodiments, $R^6$ is selected from the group consisting of hydrogen, halogen, $C_{1-4}$alkyl, and —O—$C_{1-4}$alkyl. In some embodiments, $R^6$ is selected from the group consisting of hydrogen and halogen. In some embodiments, $R^6$ is hydrogen.

$R^7$ of Formula (I) is selected from the group consisting of hydrogen, halogen, —CN, —$C_1$-6alkyl, $C_{3-10}$carbocyclyl, $C_{3-10}$heterocyclyl, —O—$C_{1-6}$alkyl, —O—$C_{3-10}$carbocyclyl, —O-(3-10 membered heterocyclyl), —NH($C_{1-6}$alkyl), —N($C_{1-6}$alkyl)$_2$, —NH—$C_{3-10}$carbocyclyl, —N($C_{1-4}$alkyl) $C_{6-10}$carbocyclyl, —NH-(3-10 membered heterocyclyl), —N($C_{1-4}$alkyl)-(3-10 membered heterocyclyl), —C(O)—$C_{1-4}$alkyl, —C(O)—$C_{3-10}$carbocyclyl, —C(O)-(3-10 membered heterocyclyl), and —C(O)N($C_{1-4}$alkyl)$_2$, wherein said alkyl, carbocyclyl or heterocyclyl may be unsubstituted or substituted with up to two substituents each independently selected from the group consisting of $C_{1-4}$alkyl, oxo, halogen and $C_{1-4}$haloalkyl.

In some embodiments. $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl.

In some embodiments, $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl.

In some embodiments, $R^7$ is selected from the group consisting of:

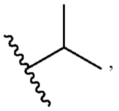
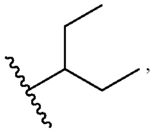
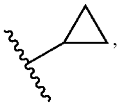
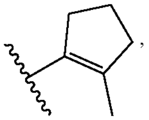
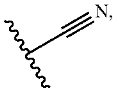
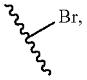
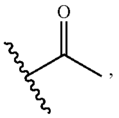
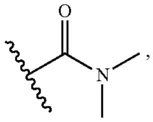
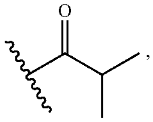
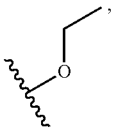
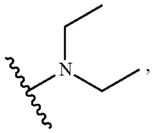

-continued

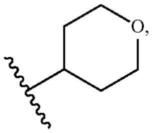
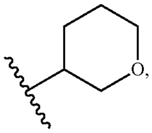
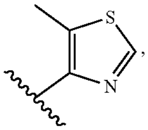
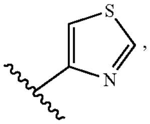
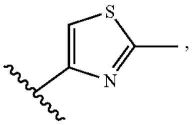
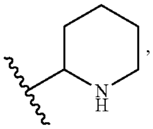
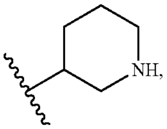
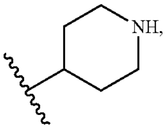
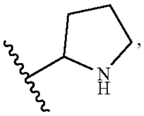
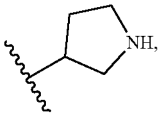
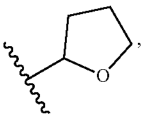
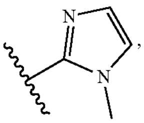
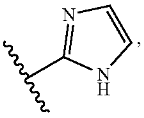

-continued

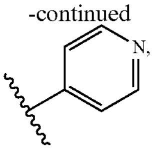

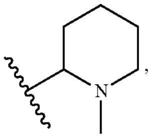

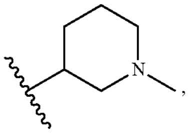

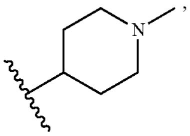

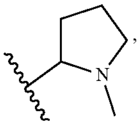

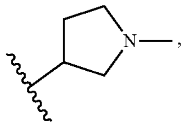

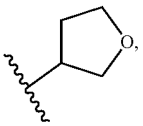

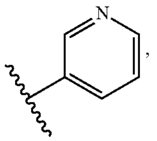

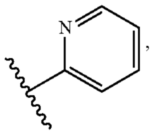

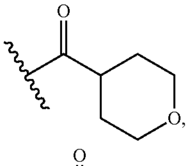

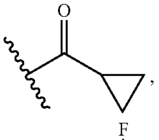

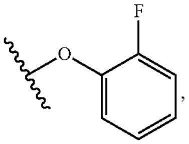

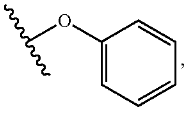

-continued

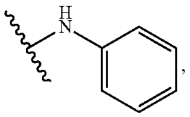

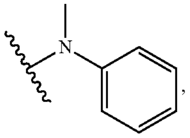

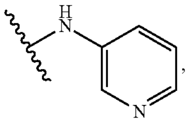

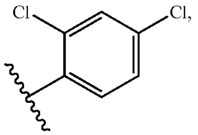

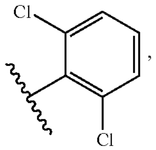

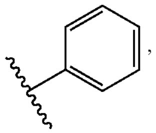

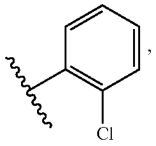

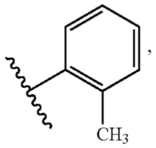

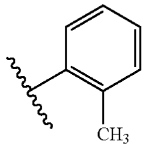

, and

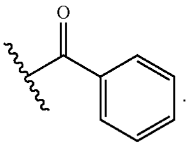

In some embodiments, $R^7$ is hydrogen.

In some embodiments, n is 0 or 1, X is O or S, $R^6$ is selected from the group consisting of hydrogen and halogen, and $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl.

In some embodiments, n is 0 or 1, X is O or S, $R^6$ is selected from the group consisting of hydrogen and halogen, and $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl.

In some embodiments, n is 0 or 1, X is O or S, $R^6$ is selected from the group consisting of hydrogen and halogen, and $R^7$ is selected from the group consisting of:

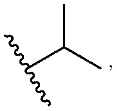
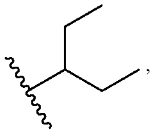
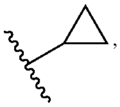
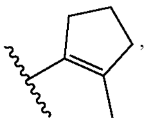
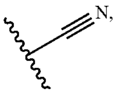
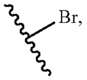
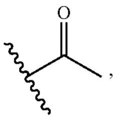
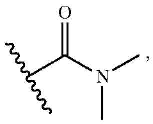
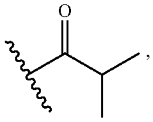
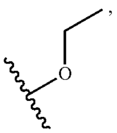

-continued

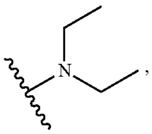
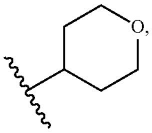
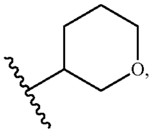
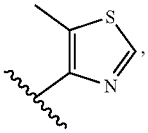
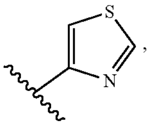
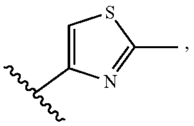
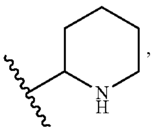
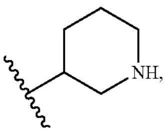
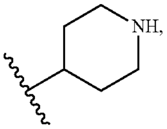
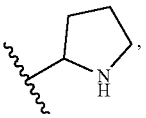
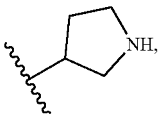
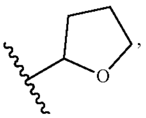
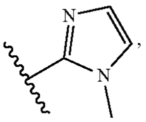

-continued
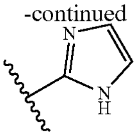,
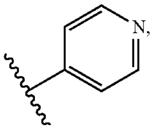
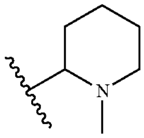,
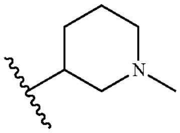,
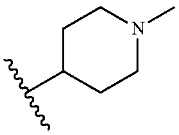,
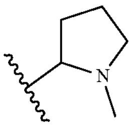,
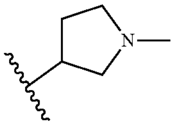,
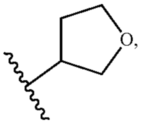
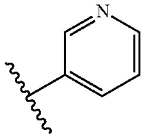,
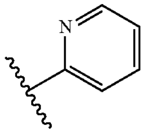,
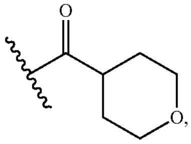
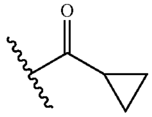,
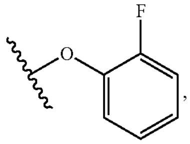,
-continued
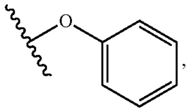,
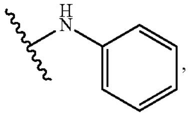,
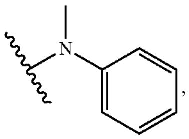,
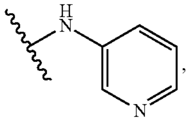,
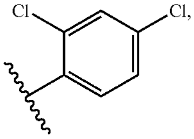
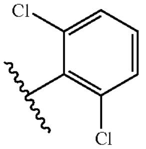,
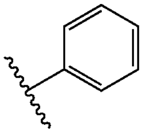,
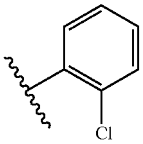,
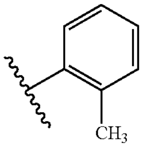,
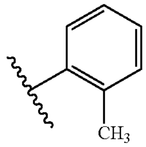, and
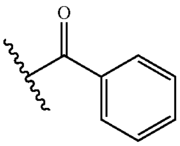.
In some embodiments, n is 0 or 1, X is O or S, $R^6$ is hydrogen, and $R^7$ is hydrogen.
In some embodiments, n is 1, X is O, $R^6$ is hydrogen, and $R^7$ is hydrogen.
In some embodiments, n is 0, X is S, $R^6$ is hydrogen, and $R^7$ is hydrogen.
In some embodiments, $R^2$ is hydrogen, $R^4$ is hydrogen, $R^1$, $R^3$ and $R^5$ are each independently selected from the group consisting of hydrogen, halogen, $C_{1-6}$alkyl, —O—$C_{1-6}$alkyl, $C_{1-6}$haloalkyl, —O—$C_{1-6}$haloalkyl, n is 0 or 1, X is O or S, $R^6$ is selected from the group consisting of hydrogen and halogen, and $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl.

In some embodiments, $R^2$ is hydrogen, $R^4$ is hydrogen, $R^1$, $R^3$ and $R^5$ are each independently selected from the group consisting of halogen, $C_{1-6}$alkyl, —O—$C_{1-6}$alkyl, n is 0 or 1, X is O or S, $R^6$ is selected from the group consisting of hydrogen and halogen, and $R^7$ is selected from the group consisting of hydrogen, —$C_{1-6}$alkyl, $C_{3-10}$carbocyclyl, —O—$C_{3-10}$carbocyclyl, —NH$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl.

In some embodiments, $R^2$ is hydrogen, $R^4$ is hydrogen, and $R^1$, $R^3$ and $R^5$ are each independently selected from the group consisting of halogen and —O—$C_{1-6}$alkyl, n is 0 or 1, X is O or S, $R^6$ is selected from the group consisting of hydrogen and halogen, and $R^7$ is selected from the group consisting of:

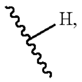

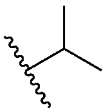

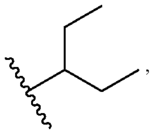

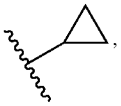

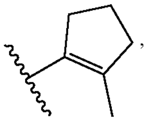

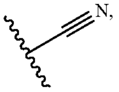

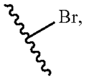

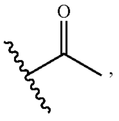

-continued

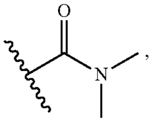

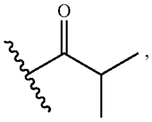

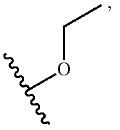

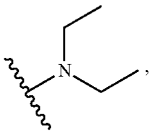

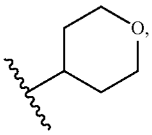

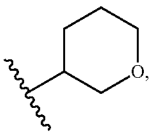

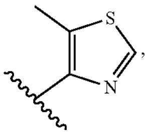

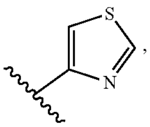

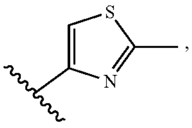

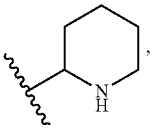

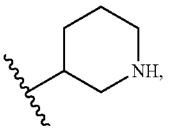

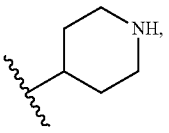

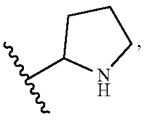

-continued
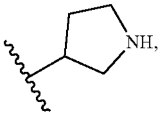
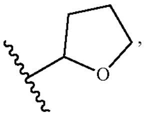
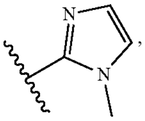
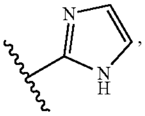
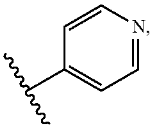
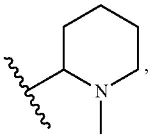
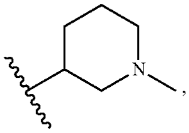
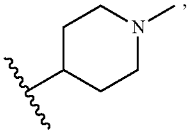
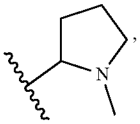
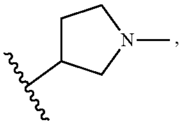
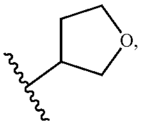
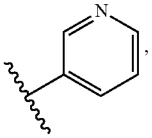
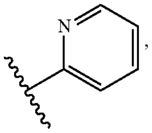
-continued
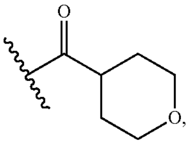
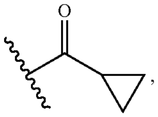
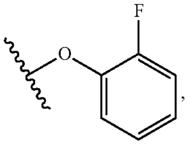
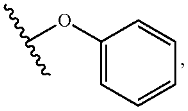
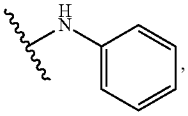
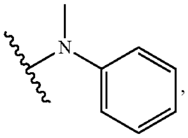
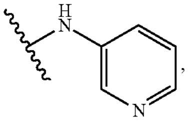
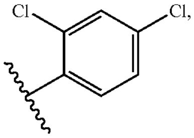
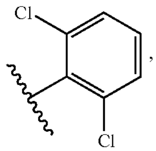
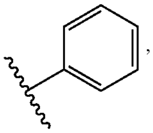
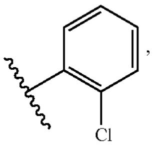
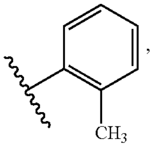

-continued

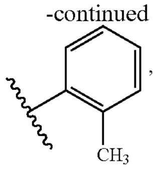

, and

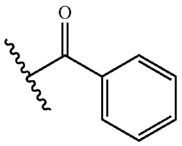

.

In some embodiments, $R^2$ is hydrogen, $R^4$ is hydrogen, $R^1$ is chlorine, $R^3$ is methoxy, $R^5$ is chlorine, n is 0 or 1, X is O or S, $R^6$ is hydrogen, and $R^7$ is hydrogen.

$R^8$ is selected from the group consisting of hydrogen, $-C_{1-8}$alkyl, $-O-C_{1-8}$alkyl, $-C_{1-4}$alkylene-$R^{13}$, $-O-C_{1-4}$alkylene-$R^{13}$ and $-O-R^{13}$.

In some embodiments, $R^8$ is selected from the group consisting of $-C_{1-4}$ alkyl and $-OC_{1-4}$alkyl.

In some embodiments, $R^8$ is selected from the group consisting of $-C_{1-4}$alkylene-$R^{13}$, $-O-C_{1-4}$alkylene-$R^{13}$ and $-O-R^{13}$, and $R^{13}$ is selected from the group consisting of hydrogen, $-C_{1-6}$alkyl, $C_{3-10}$carbocyclyl, $-O-C_{3-10}$carbocyclyl, $-NH-C_{3-10}$carbocyclyl, $C_{3-10}$heterocyclyl, $-O-C_{3-10}$heterocyclyl and $-NH-C_{3-10}$heterocyclyl.

In some embodiments, $R^8$ is selected from the group consisting of $-C_{1-4}$alkylene-$R^{13}$, $-O-C_{1-4}$alkylene-$R^{13}$ and $-O-R^{13}$, and $R^{13}$ is selected from the group consisting of hydrogen, $-C_{1-6}$alkyl, $C_{3-10}$carbocyclyl, $-O-C_{3-10}$carbocyclyl, $-NH-C_{3-10}$carbocyclyl, $C_{3-10}$heterocyclyl, $-O-C_{3-10}$ heterocyclyl and $-NH-C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl.

In some embodiments, $R^8$ is selected from the group consisting of $-C_{1-4}$alkylene-$R^{13}$, $-O-C_{1-4}$alkylene-$R^{13}$ and $-O-R^{13}$, and $R^{13}$ is selected from the group consisting of:

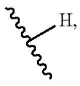

,

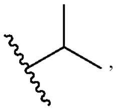

,

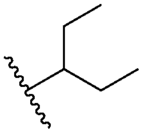

,

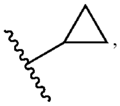

,

-continued

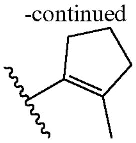

,

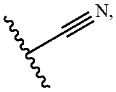

,

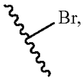

,

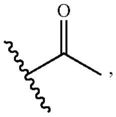

,

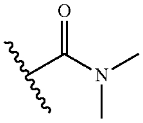

,

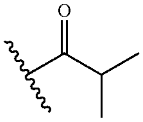

,

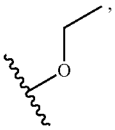

,

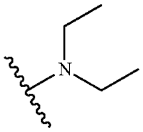

,

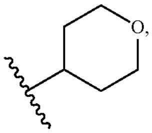

,

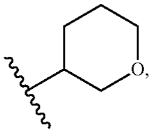

,

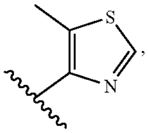

,

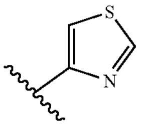

,

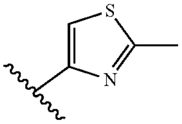

,

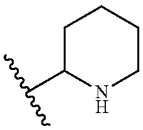

,

-continued
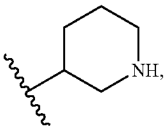
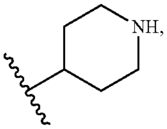
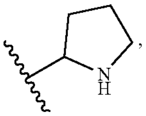
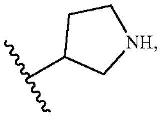
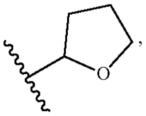
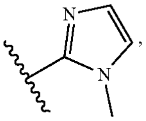
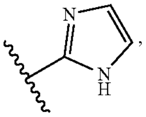
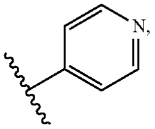
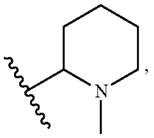
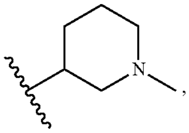
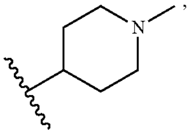
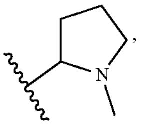
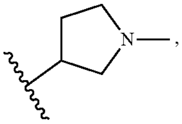
-continued
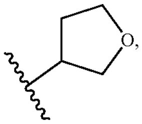
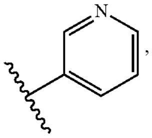
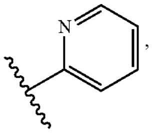
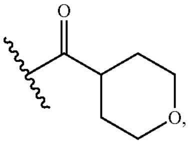
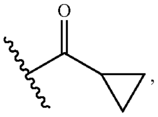
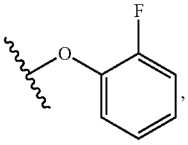
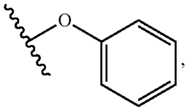
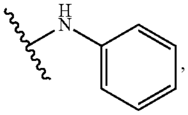
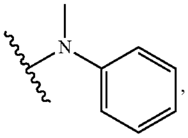
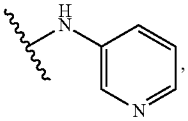
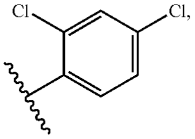
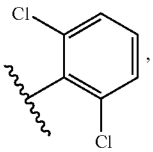
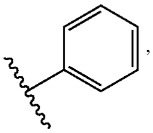

-continued

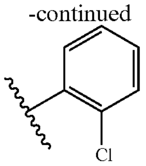,

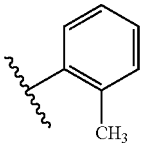,

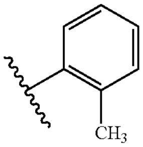, and

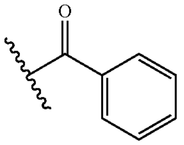.

In some embodiments, $R^8$ is hydrogen.

$R^9$ is selected from the group consisting of hydrogen and halogen. In some embodiments, $R^9$ is hydrogen. In some embodiments, $R^9$ is halogen.

$R^{10}$ is selected from the group consisting of hydrogen, $C_{1-6}$alkyl, $C_{1-6}$haloalkyl, $C_{6-10}$aryl, —$R^{14}$, —$C_{1-6}$alkylene-$R^{14}$, —$C_{6-10}$arylene-$R^{14}$, —NH—$C_{1-6}$alkyl-$R^{14'}$ and —NH—C(O)—$C_{1-6}$alkyl-$R^{14}$, wherein said aryl or arylene may optionally be substituted with one or two substituents each independently selected from the group consisting of $C_{1-4}$alkyl, halogen and $C_{1-4}$haloalkyl.

In some embodiments, $R^{10}$ is selected from the group consisting of $C_{1-6}$alkyl, $C_{1-6}$haloalkyl, and —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —O—$C_{3-10}$heterocyclyl, NH—$C_{3-10}$heterocyclyl and N(Me)-$C_{3-10}$heterocyclyl; wherein said heterocyclyl may be unsubstituted or substituted with up to three substituents each independently selected from $C_{1-4}$alkyl, oxo, halogen and $C_{1-4}$haloalkyl.

In some embodiments, $R^{10}$ is —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —$OC_{3-10}$heterocyclyl, NH—$C_{3-10}$heterocyclyl and N(Me)-$C_{3-10}$heterocyclyl; wherein said heterocyclyl is selected from the group consisting of thiomorpholinyl, piperazinyl, piperidinyl, pyrrolidinyl or morpholinyl, and wherein said heterocyclyl may be unsubstituted or substituted with up to three substituents each independently selected from $C_{1-4}$alkyl, oxo, halogen and $C_{1-4}$haloalkyl.

In some embodiments, $R^{10}$ is —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —$OC_{3-10}$heterocyclyl, NH—$C_{3-10}$heterocyclyl and N(Me)-$C_{3-10}$heterocyclyl; wherein said heterocyclyl is selected from the group consisting of

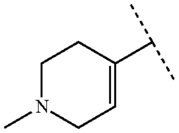, 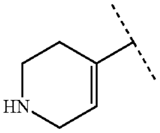 and

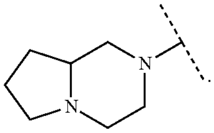.

In some embodiments, $R^{10}$ is selected from the group consisting of

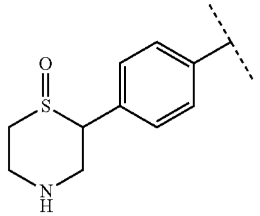, 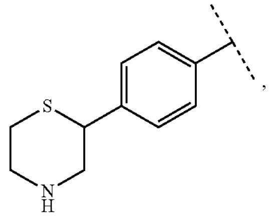,

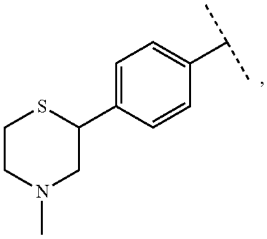, 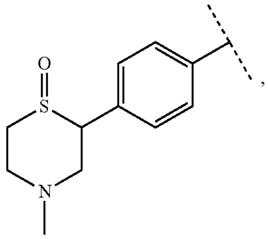,

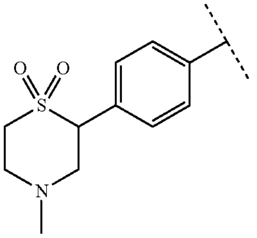, 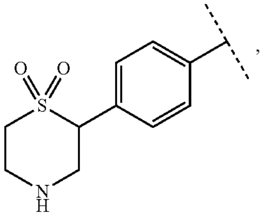,

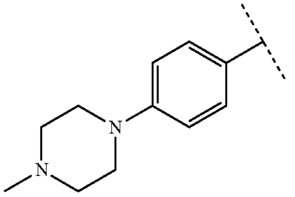,

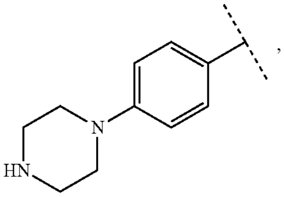,

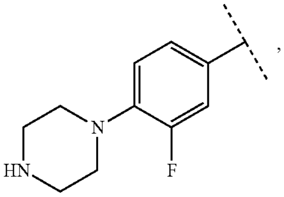,

-continued
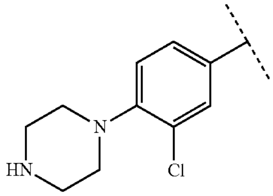,
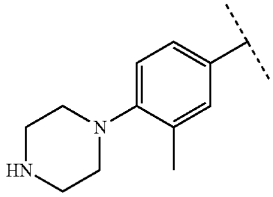,
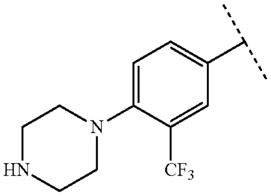, 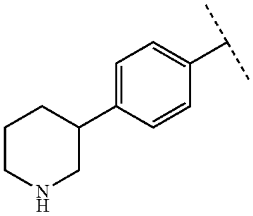,
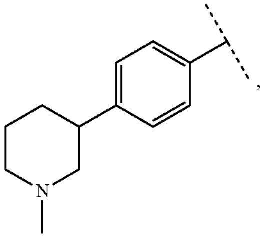, 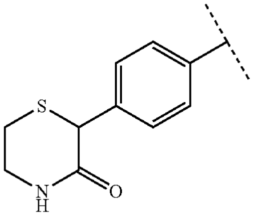,
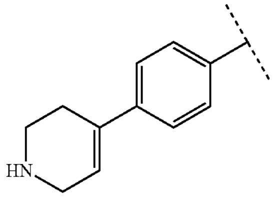,
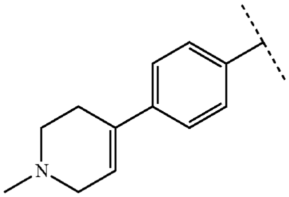,
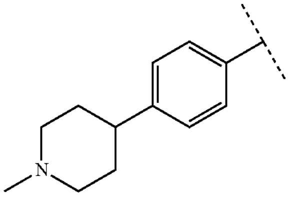,
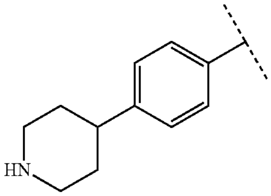, 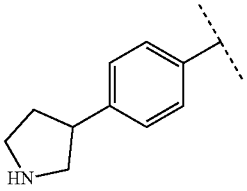,
-continued
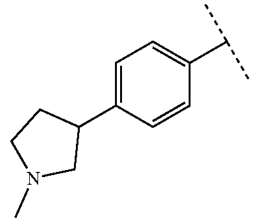, 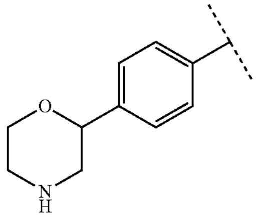,
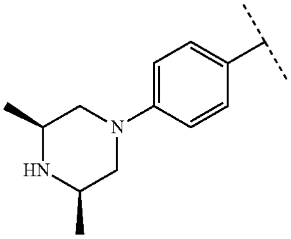,
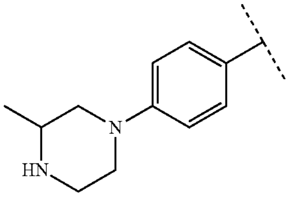,
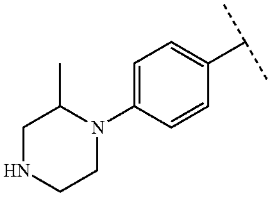,
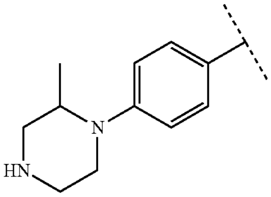,
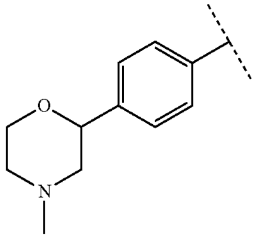,
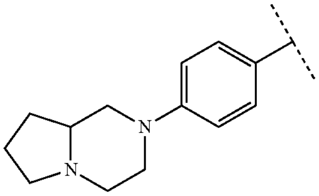,
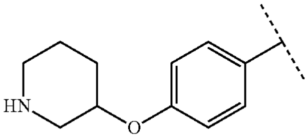, -continued

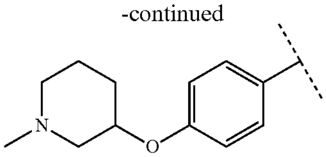,

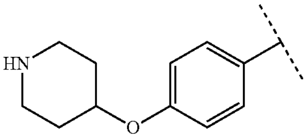,

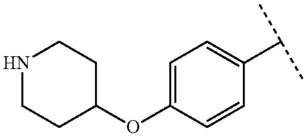,

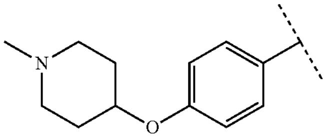,

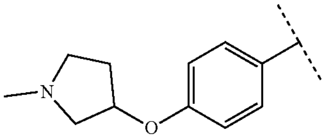,

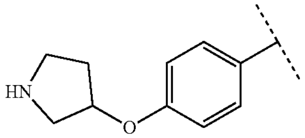,

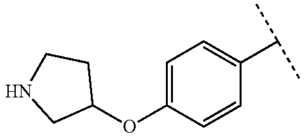,

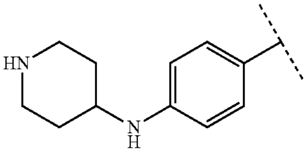,

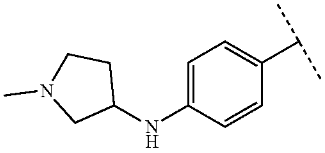,

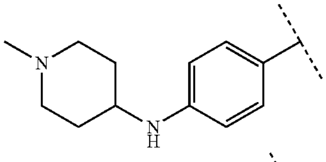,

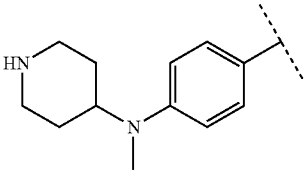,

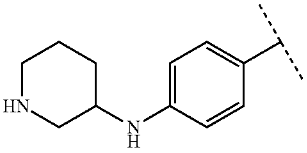,

-continued

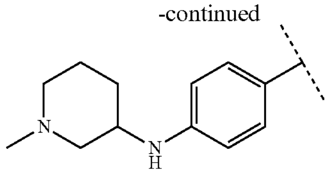

and

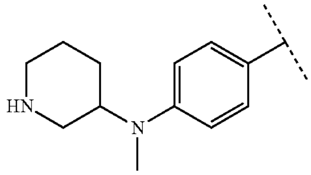.

In some embodiments, $R^{10}$ is $C_{1-6}$alkylene. In some embodiments $R^{10}$ is methyl.

In some embodiments, $R^{10}$ is —NH—$C_{1-6}$alkyl-$R^{14}$. In some embodiments, $R^{10}$ is —$NHCH_3$—$CH_3$—$R^{14}$.

In some embodiments, $R^{10}$ is —NH—C(O)—$C_{1-6}$alkyl-$R^{14}$. In some embodiments, $R^{10}$ is —NH—C(O)—$CH_3$—$R^{14}$.

In some embodiments, $R^{10}$ is —NH—$C_{1-6}$alkyl-$R^{14}$ and $R^{14}$ is —$NH_2$. In some embodiments, $R^{10}$ is —NH—C(O)—$C_{1-6}$alkyl-$R^{14}$ and $R^{14}$ is —$NH_2$.

In some embodiments, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, $R^9$ is hydrogen, and $R^{10}$ is selected from the group consisting of $C_{1-6}$alkyl, $C_{1-6}$haloalkyl, and —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —O—$C_{3-10}$heterocyclyl, NH—$C_{3-10}$heterocyclyl and N(Me)-$C_{3-10}$heterocyclyl; wherein said heterocyclyl may be unsubstituted or substituted with up to three substituents each independently selected from $C_{1-4}$alkyl, oxo, halogen and $C_{1-4}$haloalkyl.

In some embodiments, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl, $R^9$ is hydrogen, and $R^{10}$ is $C_{1-6}$alkylene or —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —O—$C_{3-10}$heterocyclyl, NH—$C_{3-10}$heterocyclyl and N(Me)-$C_{3-10}$heterocyclyl; wherein said heterocyclyl is selected from the group consisting of thiomorpholinyl, piperazinyl, piperidinyl, pyrrolidinyl or morpholinyl, and wherein said heterocyclyl may be unsubstituted or substituted with up to three substituents each independently selected from $C_{1-4}$alkyl, oxo, halogen and $C_{1-4}$haloalkyl.

In some embodiments, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl, $R^9$ is hydrogen, and $R^{10}$ is $C_{1-6}$alkylene or —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —O—$C_{3-10}$heterocyclyl, NH—$C_{3-10}$heterocyclyl and N(Me)-$C_{3-10}$heterocyclyl; wherein said heterocyclyl is selected from the group consisting of

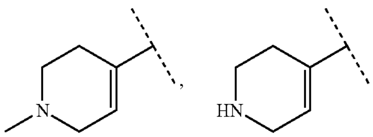

and

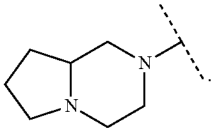

In some embodiments, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of:

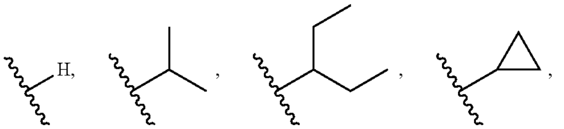

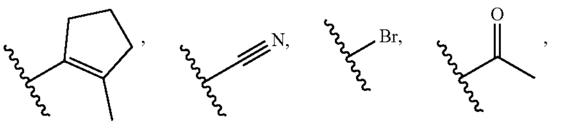

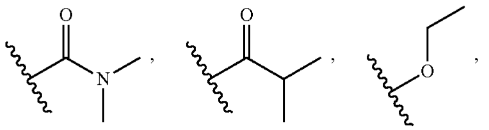

-continued

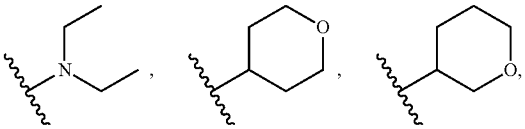

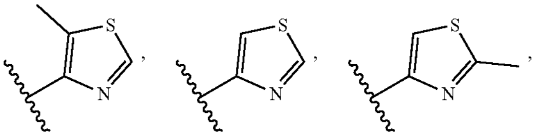

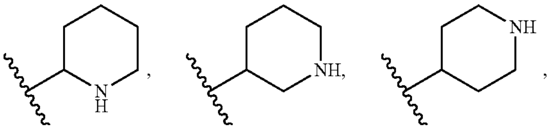

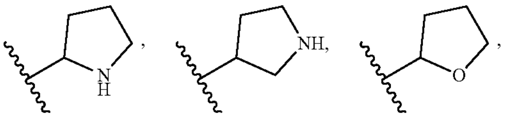

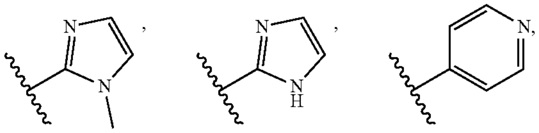

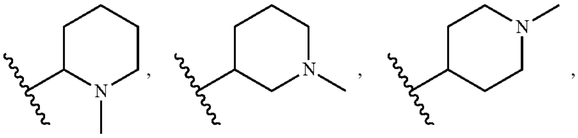

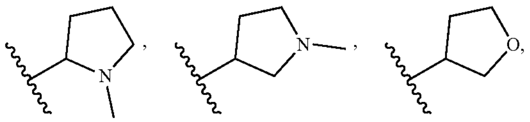

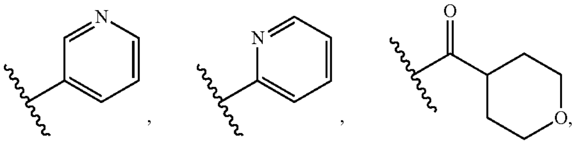

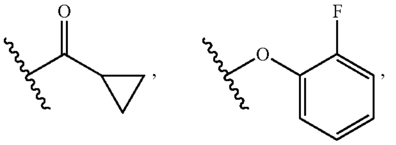

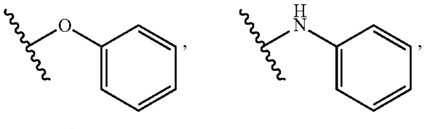

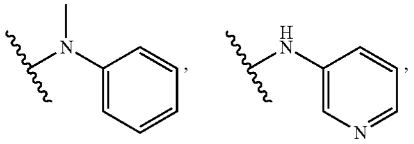

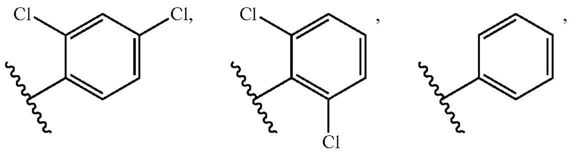

-continued
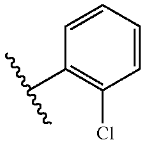,
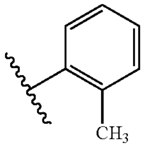,
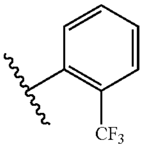, and
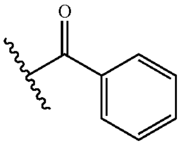.
In some embodiments, $R^9$ is hydrogen, and $R^{10}$ is methyl or is selected from the group consisting of
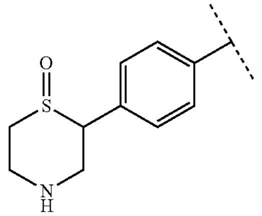,
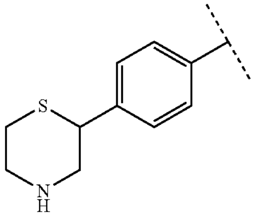,
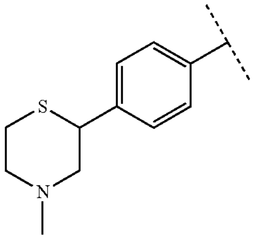,
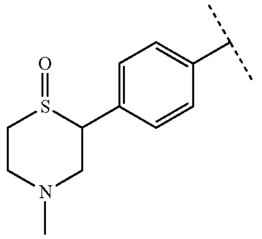,
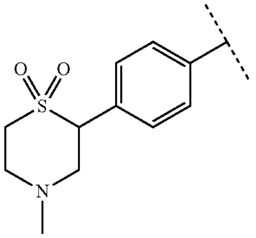,
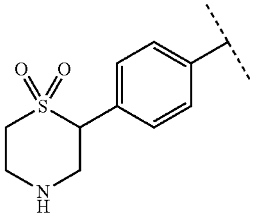,
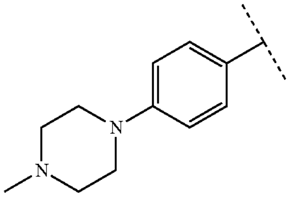,
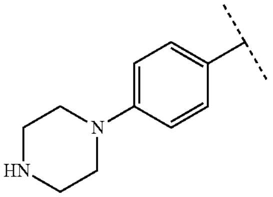,
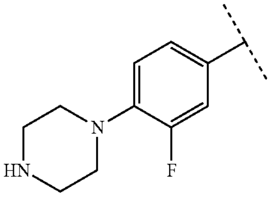,
-continued
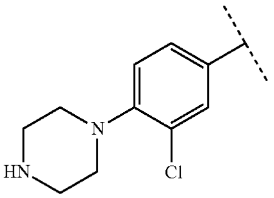,
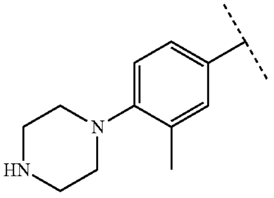,
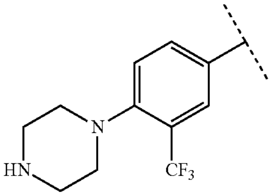,
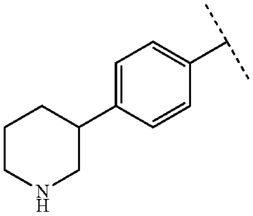,
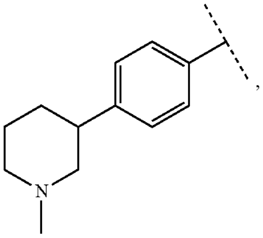,
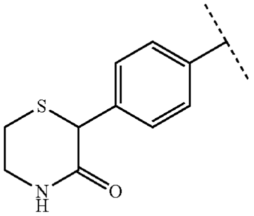,
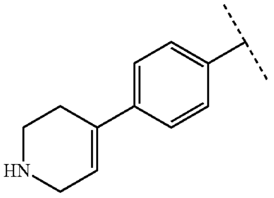,
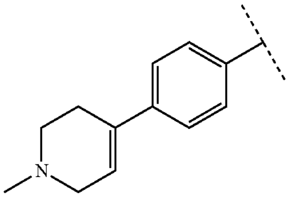,
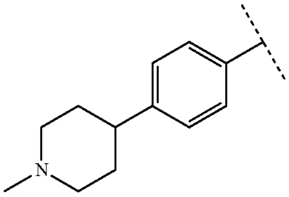,
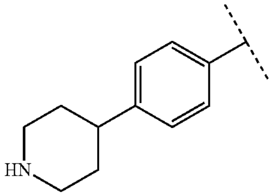,
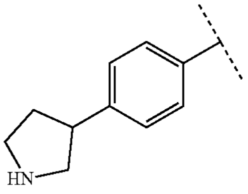, -continued
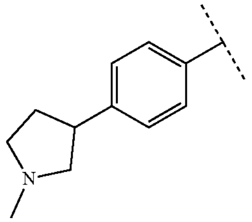
,
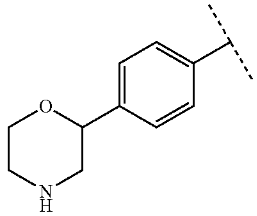
,
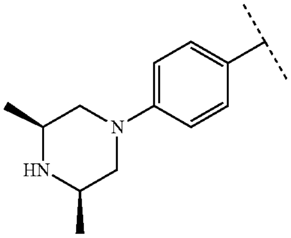
,
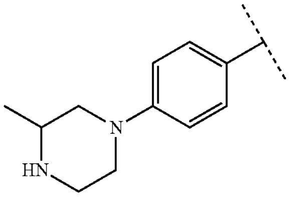
,
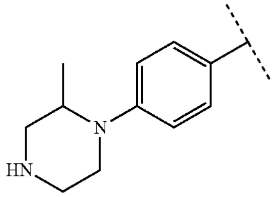
,
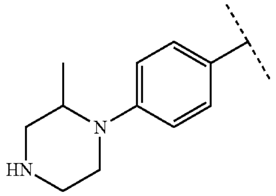
,
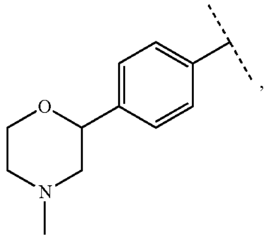
,
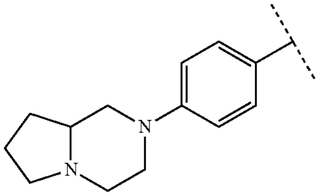
,
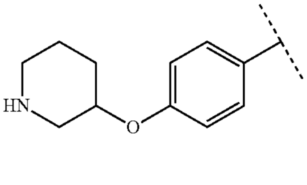
,
-continued
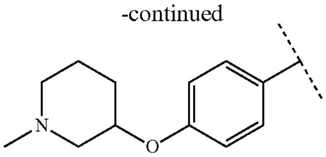
,
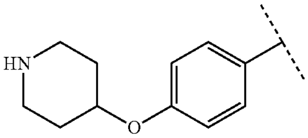
,
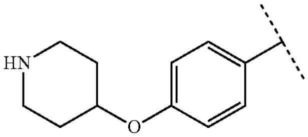
,
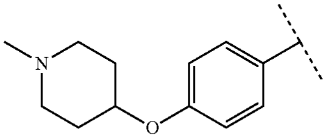
,
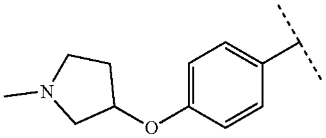
,
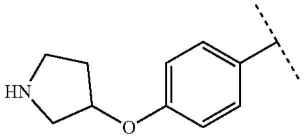
,
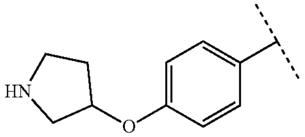
,
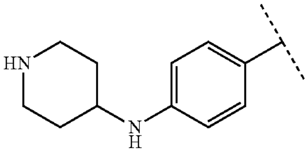
,
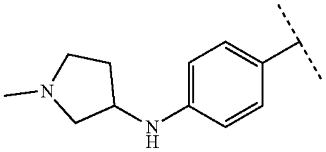
,
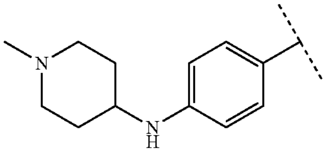
,
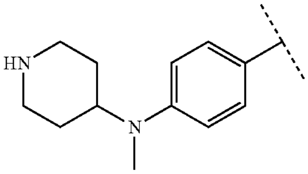
,
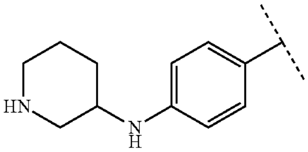
, -continued

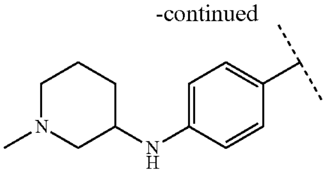

and

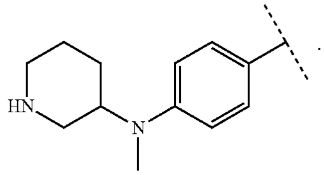

.

In some embodiments, $R^8$ is hydrogen, $R^9$ is hydrogen, and $R^{10}$ is methyl.

If present each of $R^{11}$ and $R^{12}$ is independently selected from the group consisting of hydrogen, $C_{1-6}$alkyl, $C_{3-10}$carbocyclyl, and 3-10 membered heterocyclyl. In some embodiments, each of $R^{11}$ and $R^{12}$ is independently selected from the group consisting of hydrogen and $C_{1-6}$alkyl.

In some embodiments, $R^2$ is hydrogen, $R^4$ is hydrogen, $R^1$, $R^3$ and $R^5$ are each independently selected from the group consisting of hydrogen, halogen, $C_{1-6}$alkyl, —O—$C_{1-6}$alkyl, $C_{1-6}$haloalkyl, —O—$C_{1-6}$haloalkyl, n is 0 or 1, X is O or S, $R^6$ is selected from the group consisting of hydrogen and halogen, and $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl, $R^9$ is hydrogen, and $R^{10}$ is $C_{1-6}$alkylene or —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —O—$C_{3-10}$heterocyclyl, NH—$C_{3-10}$heterocyclyl and N(Me)-$C_{3-10}$heterocyclyl; wherein said heterocyclyl is selected from the group consisting of thiomorpholinyl, piperazinyl, piperidinyl, pyrrolidinyl or morpholinyl, and wherein said heterocyclyl may be unsubstituted or substituted with up to three substituents each independently selected from $C_{1-4}$alkyl, oxo, halogen and $C_{1-4}$haloalkyl.

In some embodiments, $R^2$ is hydrogen, $R^4$ is hydrogen, $R^1$, $R^3$ and $R^5$ are each independently selected from the group consisting of halogen, $C_{1-6}$alkyl, —O—$C_{1-6}$alkyl, n is 0 or 1, X is O or S, $R^6$ is selected from the group consisting of hydrogen and halogen, $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl, $R^9$ is hydrogen, and $R^{10}$ is $C_{1-6}$alkylene or —$C_{1-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —O—$C_{3-10}$heterocyclyl, NH—$C_{3-10}$heterocyclyl and N(Me)-$C_{3-10}$heterocyclyl; wherein said heterocyclyl is selected from the group consisting of thiomorpholinyl, piperazinyl, piperidinyl, pyrrolidinyl or morpholinyl, and wherein said heterocyclyl may be unsubstituted or substituted with up to three substituents each independently selected from $C_{1-4}$alkyl, oxo, halogen and $C_{1-4}$haloalkyl.

In some embodiments, $R^2$ is hydrogen, $R^4$ is hydrogen, $R^1$, $R^3$ and $R^5$ are each independently selected from the group consisting of halogen, $C_{1-6}$alkyl, —O—$C_{1-6}$alkyl, n is 0 or 1, X is O or S, $R^6$ is selected from the group consisting of hydrogen and halogen, $R^7$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl, $R^8$ is selected from the group consisting of hydrogen, —$C_{1-4}$ alkylene-$R^{13}$, —O—$C_{1-4}$alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —$NHC_{3-10}$heterocyclyl, wherein said carbocyclyl is selected from the group consisting of $C_{1-6}$cycloalkyl, $C_{1-6}$cycloalkenyl, phenyl, which cycloalkyl, cycloalkenyl or phenyl may optionally be substituted with one or two substituents selected from the group consisting of halogen, $C_{1-2}$alkyl and $C_{1-2}$haloalkyl; and wherein said heterocyclyl is selected from the group consisting of morpholinyl, thiazolyl, piperidinyl, pyrrolidinyl, furyl, imidazolyl and pyridinyl, and said morpholinyl, thiazolyl, piperidinyl, pyrrolidinyl, furyl, imidazolyl or pyridinyl may optionally be substituted with one or two substituents selected from the group consisting of halogen, $C_{1-2}$alkyl and $C_{1-2}$haloalkyl, $R^9$ is hydrogen, and $R^{10}$ is $C_{1-6}$alkylene or —$C_{6-10}$arylene-$R^{14}$, wherein said arylene may optionally be substituted with one substituent selected from the group consisting of $C_{1-4}$alkyl, halogen and $C_{1-4}$haloalkyl; and wherein $R^{14}$ is selected from the group consisting of $C_{3-10}$heterocyclyl, —O—$C_{3-10}$heterocyclyl, NH—$C_{3-10}$heterocyclyl and N(Me)-$C_{3-10}$heterocyclyl; wherein said heterocyclyl is selected from the group consisting of

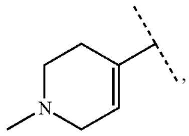
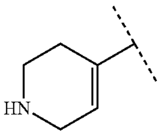
and
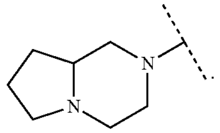

In some embodiments, $R^2$ is hydrogen, $R^4$ is hydrogen, and $R^1$, $R^3$ and $R^5$ are each independently selected from the group consisting of halogen and —O—$C_{1-6}$alkyl, n is 0 or 1, X is O or S, $R^6$ is selected from the group consisting of hydrogen and halogen, and $R^7$ is selected from the group consisting of:

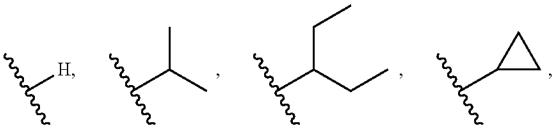
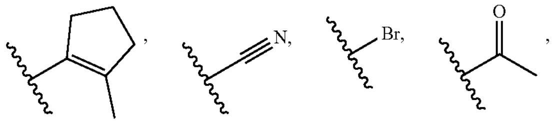
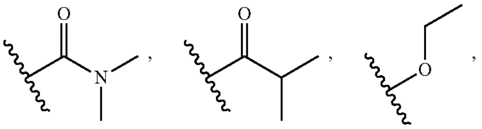
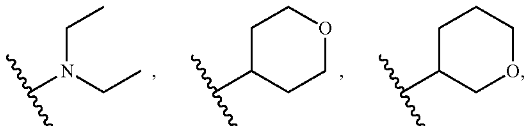
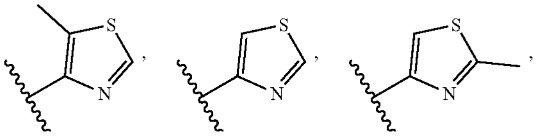

-continued

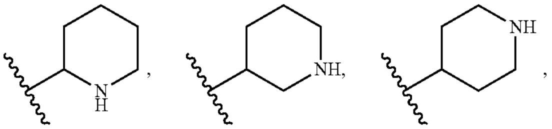
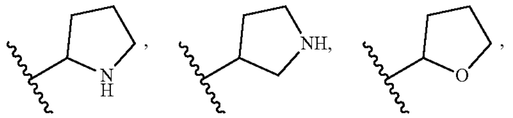
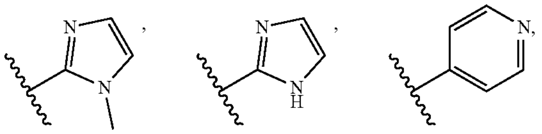
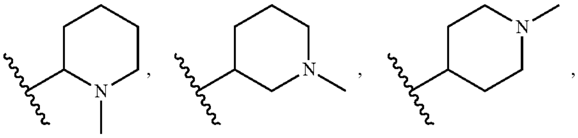
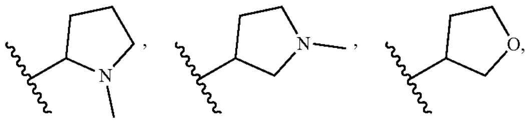
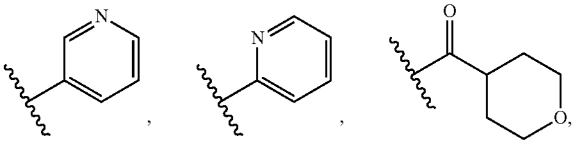
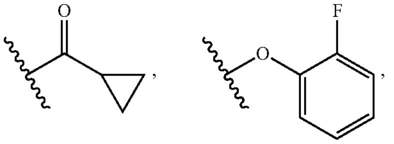
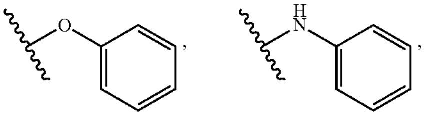
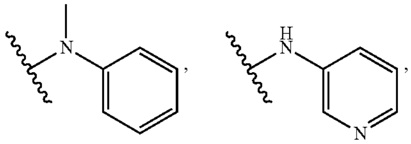
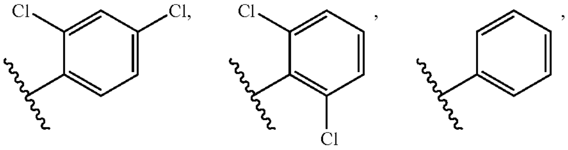
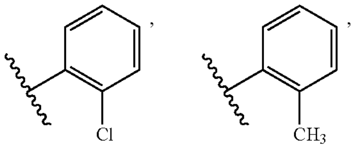
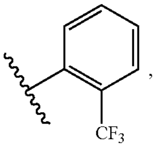
and
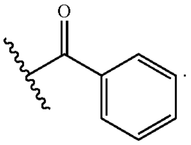

In some embodiments, $R^8$ is selected from the group consisting of hydrogen, —$C_{1-4}$alkylene-$R^{13}$, —O—$C_{1-4}$alkylene-$R^{13}$ and —O—$R^{13}$, and $R^{13}$ is selected from the group consisting of:
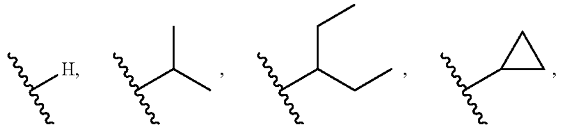
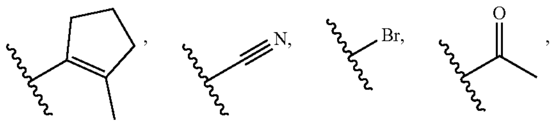
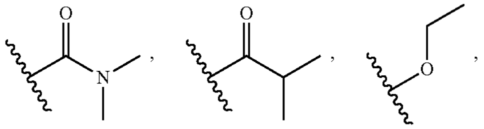
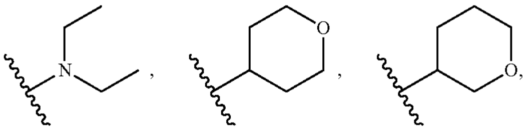
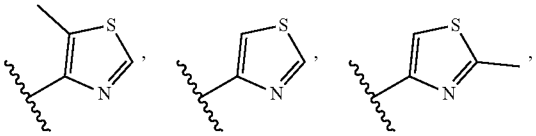
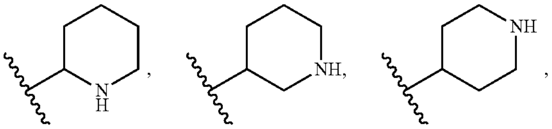
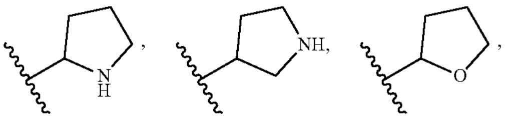
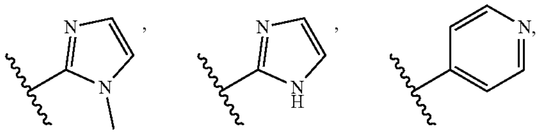
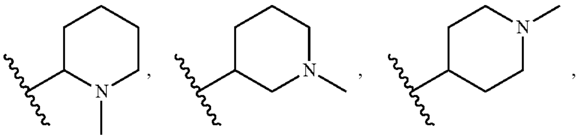
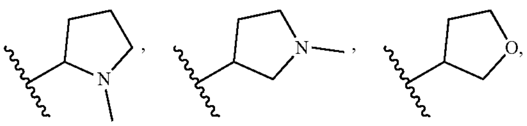
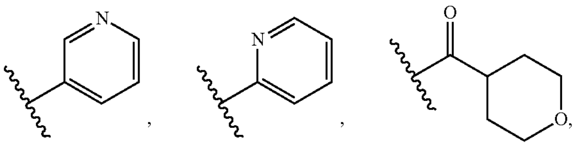
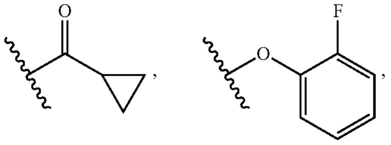
-continued
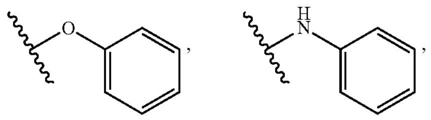
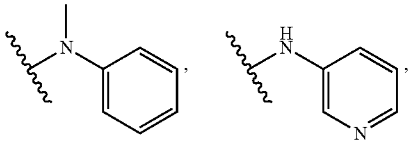
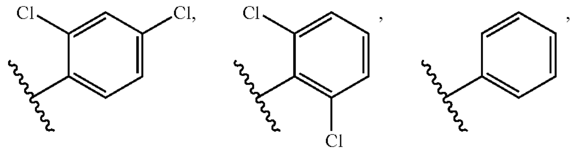
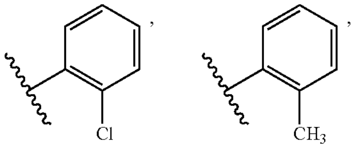
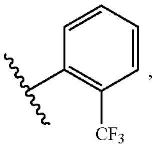
and
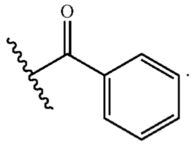
In some embodiments, $R^9$ is hydrogen, and $R^{10}$ is methyl or is selected from the group consisting of
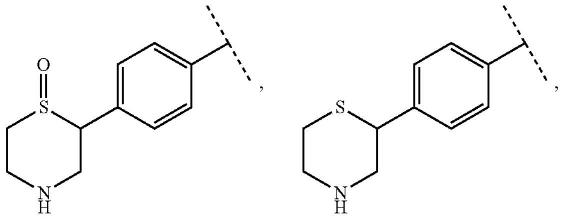
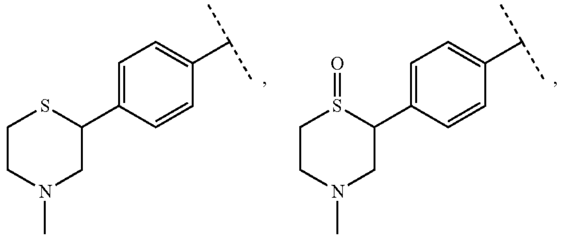
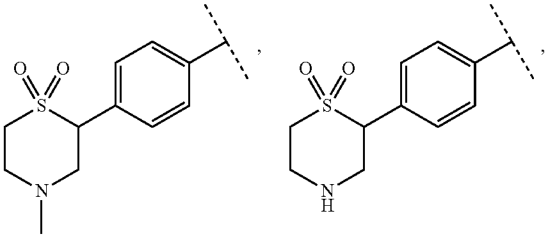

-continued
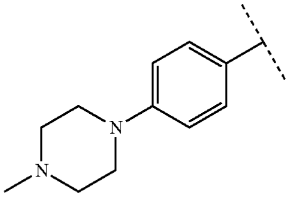
,
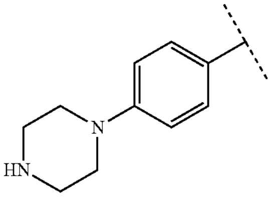
,
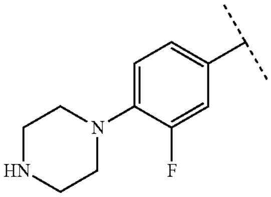
,
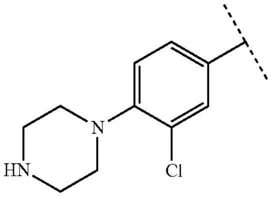
,
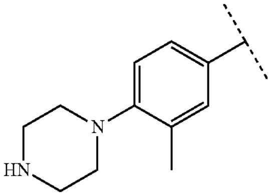
,
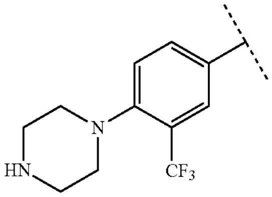
,
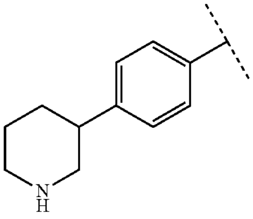
,
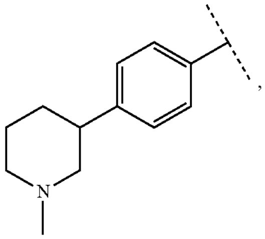
,
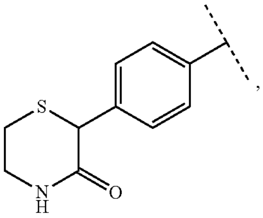
,
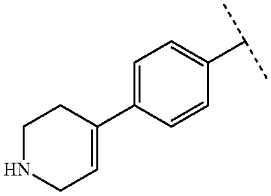
,
-continued
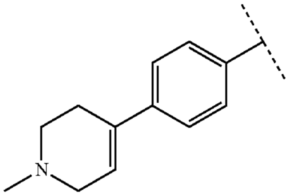
,
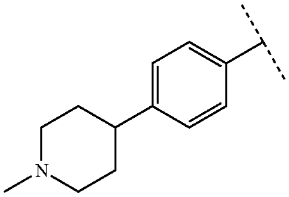
,
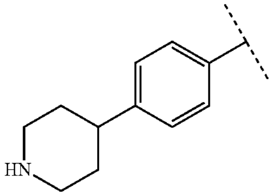
,
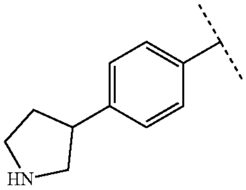
,
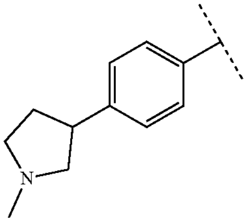
,
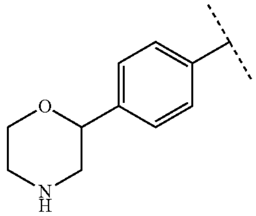
,
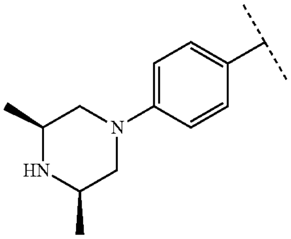
,
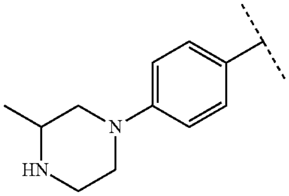
,
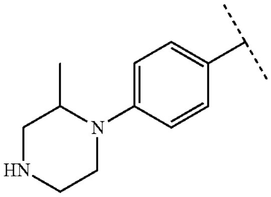
,
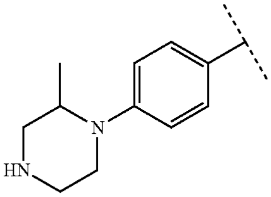
, -continued
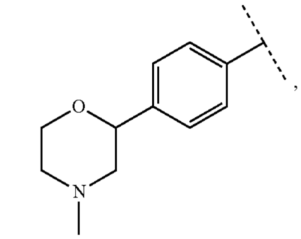
,
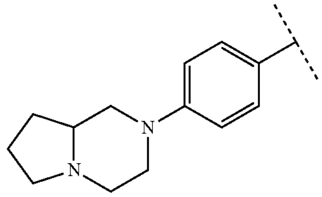
,
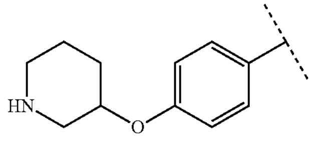
,
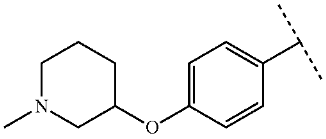
,
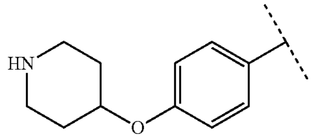
,
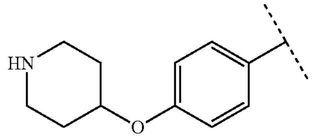
,
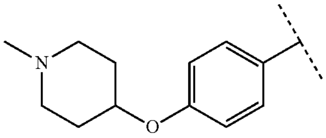
,
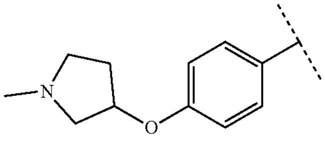
,
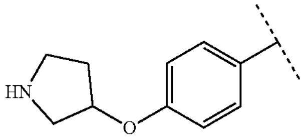
,
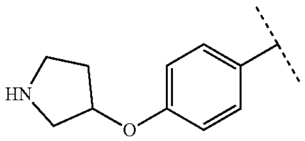
,
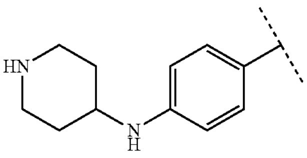
,
-continued
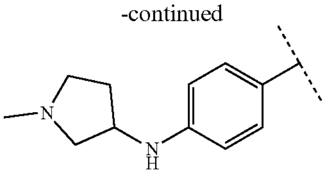
,
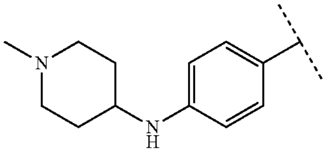
,
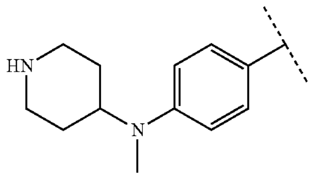
,
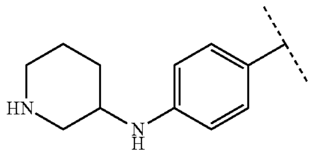
,
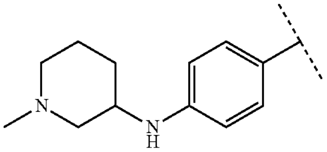
and
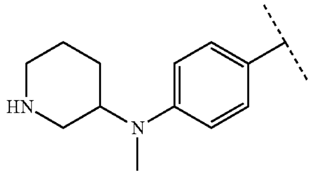
.
In some embodiments, $R^2$ is hydrogen, $R^4$ is hydrogen, $R^1$ is chlorine, $R^3$ is methoxy, $R^5$ is chlorine, n is 0 or 1, X is O or S, $R^6$ is hydrogen, $R^7$ is hydrogen, $R^8$ is hydrogen, $R^9$ is hydrogen, and $R^{10}$ is methyl.
In some embodiments, the compound of Formula (I) is:
(Ia)
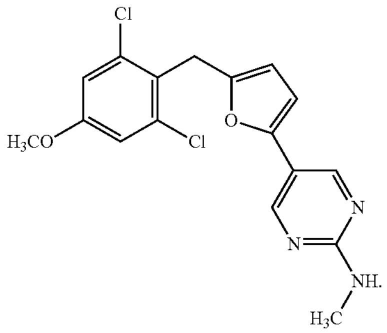
.

In some embodiments, the compound of Formula (I) is:

(Ib)

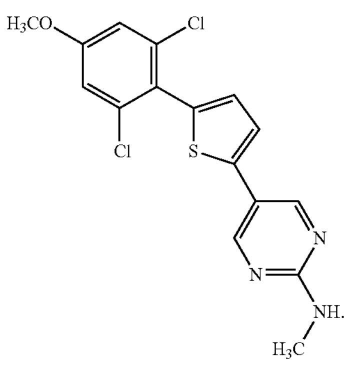

In some embodiments, the compound of Formula (I) is:

(Ic)

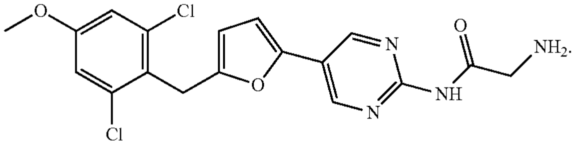

Compound Ic is considered a prodrug of Compound Ia. In some embodiments, Compound Ic is a prodrug of Compound Ia. As would be understood by the person skilled in the art, a "prodrug" is a biologically less active or inactive molecule that is capable of being metabolised in the body into the physiologically active drug form. A diverse array of biological enzymes are capable of metabolising various prodrugs into their more active forms, typically through alteration or removal of a functional moiety. In this instance, it is understood that Compound Ic is metabolised in the body into Compound Ia. Accordingly, in some embodiments, Compound Ic is metabolised into Compound Ia.

In some embodiments, the compound of Formula (I) is:

(Id)

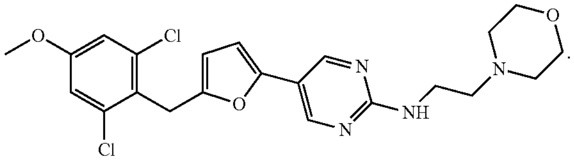

PAK Inhibitors

Compound Ia has been demonstrated to have activity as a PAK inhibitor. In some embodiments, a PAK inhibitor is a compound having an $IC_{50}$ against a PAK of at least 100 uM, at least 10 uM, at least 1 uM, or at least 200 nM.

The compounds of Formula (I) are understood to exhibit selectivity for inhibition of a particular PAK sub-type, e.g. PAK4. For example, a compound of Formula (I) may selectively bind to the PAK4 enzyme, such that it inhibits, or reduces or prevents, the downstream activity of the PAK4 enzyme. Accordingly, in some embodiments, the compound of Formula (I), or salt thereof, is a selective PAK4 inhibitor. By "selective", it is understood that the compound of Formula (I) shows a preference for binding to a particular PAK sub-type over other PAK subtypes, e.g. for PAK4 over other PAKs. In some embodiments, the compound of Formula (I) is selective for PAK4 over other PAK subtypes by at least 2-fold, at least 5-fold, or at least 10-fold.

Accordingly, the present disclosure also provides a method of inhibiting a PAK enzyme, comprising contacting a compound of Formula (I) or a salt thereof, or a pharmaceutical composition as described herein, with a PAK enzyme. The present disclosure also provides a method of inhibiting PAK4, comprising contacting a compound of Formula (I) or a salt thereof, or a pharmaceutical composition as described herein, with PAK4.

Therapeutic Methods and Uses

The compound of Formula (I) and salts thereof of the present disclosure, and pharmaceutical compositions comprising the compounds of Formula (I) and salts thereof, find use in the therapy of diseases, for example cancers. Accordingly, there is also provided a compound of Formula (I) or salt thereof as described herein, or pharmaceutical composition as described herein, for use in therapy.

A compound of Formula (I) or salt thereof, or a pharmaceutical composition as described herein, finds use in the treatment of diseases for which inhibition of PAK activity, particularly PAK 4 activity, provides a therapeutic effect. Such diseases include, but are not limited to, cancers, infectious diseases, and neurological disorders.

Accordingly, there is provided a method of preventing or treating cancer in a subject, comprising administering an effective amount of the compound of Formula (I) or a salt thereof, or of a pharmaceutical composition as described herein, to the subject. There is also provided a compound of Formula (I) or salt thereof, or a pharmaceutical composition as described herein, for use in preventing or treating cancer. There is also provided use of a compound of Formula (I) or salt thereof, or of a pharmaceutical composition as described herein, in the manufacture of a medicament for use in preventing or treating a cancer in a subject.

In some embodiments, the cancer is a PAK-dependent cancer, in other words it is a cancer in respect of which inhibition of a PAK provides a therapeutic or prophylactic effect. In some embodiments, the cancer is a PAK4-dependent cancer, i.e. a cancer in respect of which inhibition of PAK-4 provides a therapeutic or prophylactic effect.

Examples of cancers include but are not limited to pancreatic cancer, breast cancer, gastric cancer, glioma, hepatocellular cancer, cholangiocarcinoma, lung cancer, ovarian cancer, osteosarcoma, oesophageal squamous cell cancer, colon cancer, colorectal cancer, brain glioblastoma, melanoma, liver cancer, bile duct cancer, and prostate cancer. Lung cancer includes non-small-cell lung cancer.

The present compounds are understood not only to have anti-proliferative properties, but also to act by decreasing expression of PD-L1. One approach to cancer therapy is based on inhibiting the interaction between PD-1 and PD-L1, and preventing cancers from evading the immune system. This approach is referred to as immunotherapy, and agents which inhibit either PD-1 or PD-L1 are referred to as checkpoint inhibitors.

Similarly, the present compounds are understood to also act by decreasing expression of CHEK2. Further, the present compounds are understood to also act by inhibiting CHEK2.

Thus, the present compounds find use in immunotherapy. Examples of cancers for which the compounds are contemplated for use with also include, but are not limited to, melanoma, kidney cancer, bladder cancer, head and neck cancer, Hodgkin's lymphoma, colorectal cancer, brain glioblastoma, liver cancer, and bile duct cancer. In some embodiments, a compound of Formula (I) or salt thereof, or a pharmaceutical composition as described herein, is used in the prevention and/or treatment of pancreatic cancer. In some embodiments, a compound of Formula (I) or salt thereof, or a pharmaceutical composition as described herein, is used in the prevention and/or treatment of colon cancer. In some embodiments, a compound of Formula (I) or salt thereof, or a pharmaceutical composition as described herein, is used in the prevention and/or treatment of cholangiocarcinoma. In some embodiments, a compound of Formula (I) or salt thereof, or a pharmaceutical composition as described herein, is used in the prevention and/or treatment of lung cancer. In some embodiments, a compound of Formula (I) or salt thereof, or a pharmaceutical composition as described herein, is used in the prevention and/or treatment of non-small-cell lung cancer. In some embodiments, a compound of Formula (I) or salt thereof, or a pharmaceutical composition as described herein, is used in the prevention and/or treatment of melanoma. In some embodiments, a compound of Formula (I) or salt thereof, or a pharmaceutical composition as described herein, is used in the prevention and/or treatment of kidney cancer. In some embodiments, a compound of Formula (I) or salt thereof, or a pharmaceutical composition as described herein, is used in the prevention and/or treatment of bladder cancer. In some embodiments, a compound of Formula (I) or salt thereof, or a pharmaceutical composition as described herein, is used in the prevention and/or treatment of head and neck cancer. In some embodiments, a compound of Formula (I) or salt thereof, or a pharmaceutical composition as described herein, is used in the prevention and/or treatment of Hodgkin's lymphoma. In some embodiments, a compound of Formula (I) or salt thereof, or a pharmaceutical composition as described herein, is used in the prevention and/or treatment of colorectal cancer. In some embodiments, a compound of Formula (I) or salt thereof, or a pharmaceutical composition as described herein, is used in the prevention and/or treatment of brain glioblastoma. In some embodiments, a compound of Formula (I) or salt thereof, or a pharmaceutical composition as described herein, is used in the prevention and/or treatment of liver cancer. In some embodiments, a compound of Formula (I) or salt thereof, or a pharmaceutical composition as described herein, is used in the prevention and/or treatment of bile duct cancer.

In some embodiments, the cancer is selected from the group consisting of melanoma, kidney cancer, bladder cancer, head and neck cancer, Hodgkin's lymphoma, pancreatic cancer, breast cancer, gastric cancer, glioma, hepatocellular cancer, cholangiocarcinoma, lung cancer, ovarian cancer, osteosarcoma, oesophageal squamous cell cancer, colon cancer, colorectal cancer, brain glioblastoma, liver cancer, bile duct cancer, and prostate cancer.

In some embodiments, a compound of Formula (I) which is used in therapy (e.g. in cancer therapy) is:

(Ia)

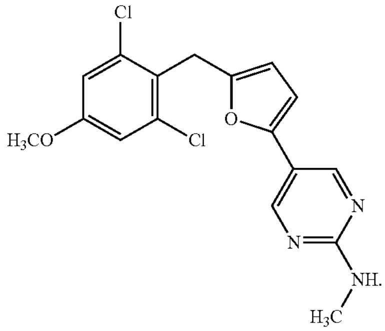

In some embodiments, a compound of Formula (I) which is used in therapy (e.g. in cancer therapy) is:

(Ib)

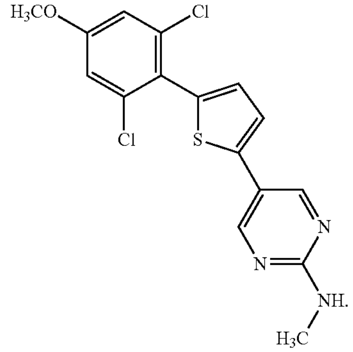

In some embodiments, a compound of Formula (I) which is used in therapy (e.g. in cancer therapy) is:

(Ic)

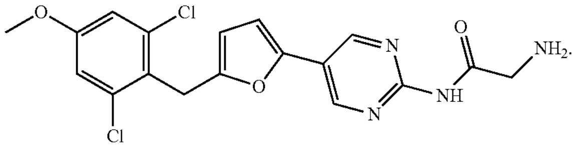

In some embodiments, a compound of Formula (I) which is used in therapy (e.g. in cancer therapy) is:

(Ic)

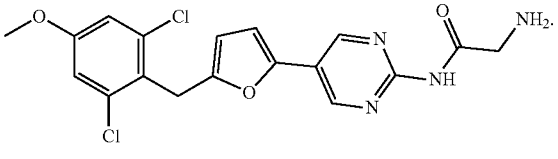

which is metabolised in the body to produce Compound Ia.

In some embodiments, a compound of Formula (I) which is used in therapy (e.g. in cancer therapy) is:

(Id)

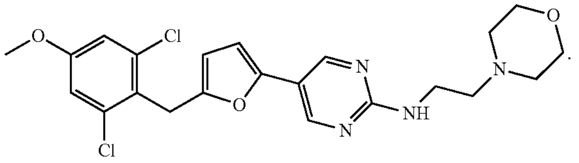

In some embodiments, there is provided a method of therapy comprising administering a therapeutically effective amount of a compound of Formula (I) to a patient in need thereof. In some embodiments, there is provided a method of therapy comprising administering a therapeutically effective amount of Compound Ia to a patient in need thereof. In some embodiments, there is provided a method of therapy comprising administering a therapeutically effective amount of Compound Ib to a patient in need thereof. In some embodiments, there is provided a method of therapy comprising administering a therapeutically effective amount of Compound Ic to a patient in need thereof. In some embodiments, there is provided a method of therapy comprising administering a therapeutically effective amount of Compound Id to a patient in need thereof.

In some embodiments, there is provided a method of therapy comprising administering a therapeutically effective amount of a prodrug of a compound of Formula (I) to a patient in need thereof. In some embodiments, there is provided a method of therapy comprising administering a therapeutically effective amount of the prodrug Compound Ic to a patient in need thereof, wherein Compound Ic is metabolised following administration to produce Compound Ia.

In some embodiments, there is provided a method of treating cancer comprising administering a therapeutically effective amount of a compound of Formula (I) to a patient in need thereof. In some embodiments, there is provided a method of treating cancer comprising administering a therapeutically effective amount of Compound Ia to a patient in need thereof. In some embodiments, there is provided a method of treating cancer comprising administering a therapeutically effective amount of Compound Ib to a patient in need thereof. In some embodiments, there is provided a method of treating cancer comprising administering a therapeutically effective amount of Compound Ic to a patient in need thereof. In some embodiments, there is provided a method of treating cancer comprising administering a therapeutically effective amount of Compound Id to a patient in need thereof.

In some embodiments, there is provided a method of treating cancer comprising administering a therapeutically effective amount of a prodrug of a compound of Formula (I) to a patient in need thereof. In some embodiments, there is provided a method of treating cancer comprising administering a therapeutically effective amount of the prodrug Compound Ic to a patient in need thereof, wherein Compound Ic is metabolised following administration to produce Compound Ia.

Immunotherapy and Combination Treatments

Compound Ia has been demonstrated to inhibit PD-L1 expression. In some embodiments there is provided a method of decreasing PD-L1 expression, comprising contacting a compound of Formula (I) or a salt thereof, or a pharmaceutical composition comprising the compound or salt, with a PAK enzyme. As discussed above, checkpoint inhibitors are understood to act by blocking the interaction and/or binding of PD-1 with one or both of its ligands, PD-L1 and PD-L2. In some embodiments, there is provided a method of decreasing the binding of PD-L1 to PD-1, comprising contacting a compound of Formula (I) or a salt thereof, or a pharmaceutical composition comprising the compound or salt, with a PAK enzyme.

In some embodiments, the PAK enzyme is a PAK4 enzyme. In one example, there is provided a method of decreasing PD-L1 expression, comprising contacting a compound of Formula (I) or a salt thereof, or a pharmaceutical composition comprising the compound or salt, with a PAK4 enzyme. In some embodiments, there is provided a method of decreasing the binding of PD-L1 to PD-1, comprising contacting a compound of Formula (I) or a salt thereof, or a pharmaceutical composition comprising the compound or salt, with a PAK4 enzyme.

Compound Ia has also been demonstrated to inhibit Checkpoint Kinase 2 (CHEK2) expression. CHEK2 is a tumour suppression gene, in which mutations to the gene are understood to cause a wide range of cancers. CHEK2 encodes the protein CHEK2, which is a versatile and multifunctional kinase that regulates the cell's response to DNA damage by phosphorylating a number of distinct cellular substrates. On the basis of its role during DNA damage response, CHEK2 has been suggested as an anticancer therapy target. Compound Ia has also been demonstrated to inhibit CHEK2. In some embodiments there is provided a method of decreasing CHEK2 expression, comprising contacting a compound of Formula (I) or a salt thereof, or a pharmaceutical composition comprising the compound or salt, with a PAK enzyme. In some embodiments there is provided a method of inhibiting CHEK2, comprising contacting a compound of Formula (I) or a salt thereof, or a pharmaceutical composition comprising the compound or salt, with a PAK enzyme.

In particular, it is understood that anticancer therapy is greatly enhanced by CHEK2 inhibition, as CHEK2 inhibition may sensitize the tumour to DNA-damaging agents used in chemotherapy. Therefore, CHEK2 inhibitors could protect healthy tissues and sensitize the tumour to chemotherapy.

Combination therapies, whereby both immune checkpoint inhibition and modulation of the tumour microenvironment are achieved, may for example prove a useful combination in treating cancer types that have developed resistance to immune checkpoint inhibition alone.

Combination therapy will be understood to mean the combined administration of two or more therapies. It will be understood that it is not necessary to administer such therapies simultaneously or via the same administration route. Instead, it will be understood that reference to a combination therapy refers to the two or more therapies being prescribed for use to a patient in need thereof. For example, the two or more therapies may be administered simultaneously, sequentially, and/or separately. The therapies may for example be administered periodically relative to each other (e.g. at a weekly interval from each other).

Accordingly, in some embodiments there is provided a compound of Formula (I) or a salt thereof, in combination with a further therapeutic agent. In some embodiments, there is provided a pharmaceutical formulation comprising the compound of Formula (I) or a salt thereof, further comprising a further therapeutic agent.

The further therapeutic agent may for example be any agent that is capable of modulating the tumour microenvironment such that the effects of immune checkpoint inhibition resistance are reduced. The further therapeutic agent may be, for example, any agent that is used in combination therapy with checkpoint inhibitors.

In some embodiments, a PAK inhibitor, for example a compound of Formula (I) or salt thereof, is used in a combination with a further therapeutic agent which is used in combination with a checkpoint inhibitor such as pembrolizumab or nivolumab. In such combinations, the PAK inhibitor may used in combination with a further therapeutic agent, for example a cytotoxic agent and/or an agent that serves to modulate the tumour microenvironment.

In one example, the further therapeutic agent is an anticancer agent. That is, an anticancer agent that has demonstrated anti-cancer, or chemotherapeutic, activity. In some embodiments, the further therapeutic agent is a monoclonal antibody. In one example, the further therapeutic agent is ipilimumab. In one example, the further therapeutic agent is bevacizumab. In some embodiments, the anti-cancer agent is a chemotherapeutic. In one example, the further therapeutic agent is pemetrexed. In one example, the further therapeutic agent is gemcitabine.

In one example, the further therapeutic agent is etoposide. In some embodiments, the further therapeutic agent is a platinum chemotherapeutic. In one example, the further therapeutic agent is cisplatin. In one example, the further therapeutic agent is oxaliplatin. In one example, the further therapeutic agent is carboplatin. In one example, the further therapeutic agent is nedaplatin. In some embodiments, the further therapeutic agent is a taxane. In one example, the further therapeutic agent is paclitaxel. In one example, the further therapeutic agent is nab-paclitaxel. In one example, the further therapeutic agent is cabazitaxel. In one example, the further therapeutic agent is docetaxel.

There is also provided a combination therapy comprising one or more PAK inhibitors, for example, a compound of Formula (I) or a salt thereof, and one or more further therapeutic agents. In some embodiments, there is provided a combination therapy comprising one or more PAK4 inhibitors, for example, a compound of Formula (I) or a salt thereof, and one or more further therapeutic agents. As an example, compound Ia may be used in a combination therapy with one or more further therapeutic agents. In one example, a combination therapy comprises a compound of Formula (I) or a salt thereof and one or more therapeutic agents. In one example, a combination therapy comprises compound Ia or a salt thereof and one or more further therapeutic agents.

Alternatively, in some embodiments, a checkpoint inhibitor is used in combination with a PAK inhibitor, for example a compound of Formula (I) or a salt thereof. In some embodiments, a checkpoint inhibitor is used in combination with a PAK4 inhibitor, for example a compound of Formula (I) or a salt thereof.

Accordingly, there is provided a combination therapy comprising one or more checkpoint inhibitors and one or more PAK inhibitors, for example, a compound of Formula (I) or a salt thereof. In one example, there is provided a combination therapy comprising one or more checkpoint inhibitors and one or more PAK4 inhibitors, for example, a compound of Formula (I) or a salt thereof. As an example, compound Ia may be used in a combination therapy with one or more checkpoint inhibitors. In one example, a combination therapy comprises a compound of Formula (I) or a salt thereof and one or more checkpoint inhibitors. In one example, a combination therapy comprises compound Ia or a salt thereof and one or more checkpoint inhibitors.

In some embodiments there is provided a compound of Formula (I) or a salt thereof, in combination with a checkpoint inhibitor. In some aspects, there is provided a pharmaceutical composition comprising a compound of Formula (I) or salt thereof, further comprising a checkpoint inhibitor. In some embodiments, the checkpoint inhibitor is a PD-1 or PD-L1 inhibitor.

In some embodiments, the checkpoint inhibitor is nivolumab. In one example, the checkpoint inhibitor is pembrolizumab. In some embodiments, the checkpoint inhibitor is pidilizumab. In some embodiments, the checkpoint inhibitor is AMP-224. In some embodiments, the checkpoint inhibitor is TSR-042. In some embodiments, the checkpoint inhibitor is BMS-936559. In some embodiments, the checkpoint inhibitor is BMS-1001. In some embodiments, the checkpoint inhibitor is BMS-1166. In some embodiments, the checkpoint inhibitor is BGB-A317. In some embodiments, the checkpoint inhibitor is atezolizumab. In one example, the checkpoint inhibitor is avelumab. In some embodiments, the checkpoint inhibitor is cemiplimab. In some embodiments, the checkpoint inhibitor is durvalumab. In some embodiments, the checkpoint inhibitor is a compound that reduces CHEK2 expression. In some embodiments, the checkpoint inhibitor is a CHEK2 inhibitor. In some embodiments, the checkpoint inhibitor is CCT241533. In some embodiments, the checkpoint inhibitor is BML-277.

Compositions

Whilst a compound of Formula (I) or salt thereof may in some embodiments be administered alone, it is more typically administered as part of a pharmaceutical composition or formulation. Thus, the present disclosure also provides a pharmaceutical composition comprising a compound of Formula (I) or salt thereof and a pharmaceutically acceptable excipient. The pharmaceutical composition comprises one or more pharmaceutically acceptable diluents, carriers or excipients (collectively referred to herein as "excipient" materials).

The present disclosure also provides pharmaceutical formulations or compositions, both for veterinary and for human medical use, which comprise compounds of Formula (I) of the present disclosure or a pharmaceutically acceptable salt thereof, with one or more pharmaceutically acceptable carriers, and optionally any other therapeutic ingredients, stabilisers, or the like. The carrier(s) must be pharmaceutically acceptable in the sense of being compatible with the other ingredients of the formulation and not unduly deleterious to the recipient thereof.

Examples of pharmaceutical formulations include those suitable for oral, parenteral (including subcutaneous, intradermal, intramuscular, intravenous, and intraarticular), inhalation (including fine particle dusts or mists that may be generated by means of various types of metered dose pressurised aerosols), nebulisers or insufflators, rectal, intraperitoneal and topical (including dermal, buccal, sublingual, and intraocular) administration, although the most suitable route may depend upon, for example, the condition and disorder of the recipient.

The pharmaceutical formulations may conveniently be presented in unit dosage form and may be prepared by any of the methods well known in the art of pharmacy. All methods include the step of brining a compound of Formula (I) or salt thereof into association with the excipient that constitutes one or more necessary ingredients. In general, the formulations are prepared by uniformly and intimately bringing into association the active ingredient with liquid carriers or finely divided solid carriers or both, and then, if necessary, shaping the product into the desired formulation.

In some embodiments, that composition is formulated for oral delivery. For example, pharmaceutical formulations of the present invention suitable for oral administration may be presented as discrete units such as capsules, cachets, pills or tablets each containing a predetermined amount of the active ingredient; as a powder or granules, as a solution or a suspension in an aqueous liquid or non-aqueous liquid, for example as elixirs, tinctures, suspensions or syrups; or as an oil-in-water liquid emulsion or a water-in-oil liquid emulsion. A compound of Formula (I) may also be presented as a bolus, electuary or paste.

A tablet may be made for example by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Moulded tablets may be made by moulding in a suitable machine a mixture of the powdered compound moistened with an inert liquid diluent. The tablets may be optionally coated or scored, and may be formulated so as to provide slow or controlled release of the compound of Formula (I). The compound of Formula (I) can, for example, be administered in a form suitable for immediate release or extended release. Immediate release or extended release can be achieved by the use of suitable pharmaceutical compositions comprising a compound of Formula (I) or, particularly in the case of extended release, by the use of devices such as subcutaneous implants or osmotic pumps. A compound of Formula (I) may also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavouring agents such as those well known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents, and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Disintegrators include without limitation, starch, methylcellulose, agar, bentonite, xanthan gum, and the like. A compound of Formula (I) can also be delivered through the oral cavity by sublingual and/or buccal administration. Moulded tablets, compressed tablets, or freeze-dried tablets are exemplary forms that may be used. Exemplary compositions include those formulating a compound of Formula (I) with fast dissolving diluents such as mannitol, lactose, sucrose and/or cyclodextrins. Also included in such formulations may be high molecular weight excipients such as cellulose (avicel) or polyethylene glycols (PEGs). Such formulations can also include an excipient to aid mucosal adhesion such as hydroxyl propyl cellulose (HPC), hydroxyl propyl methyl cellulose (HPMC), sodium carboxy methyl cellulose (SCMC), maleic anhydride copolymer, and agents to control release such as polyacrylic copolymer. Lubricants, glidants, flavours, colouring agents, and stabilisers may also be added for ease of fabrication and use. Lubricants used in these dosage forms include sodium oleate, sodium stearate, magnesium stearate, sodium benzoate, sodium acetate, sodium chloride, and the like. For oral administration in liquid form, the oral drug components can be combined with any oral, nontoxic, pharmaceutically acceptable inert carrier such as ethanol, glycerol, water, and the like.

In some embodiments, the composition is formulated for parenteral delivery. Formulations for parenteral administration include aqueous and non-aqueous sterile injections solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1.3-butanediol, water, Ringer's solution, an isotonic sodium chloride solution, or other suitable dispersing or wetting and suspending agents, including synthetic mono- or diglycerides, and fatty acids, including oleic acid, or Cremaphor.

For example, in one embodiment, the formulation may be a sterile, lyophilized composition that is suitable for reconstitution in an aqueous vehicle prior to injection. In one embodiment, a formulation suitable for parenteral administration conveniently comprises a sterile aqueous preparation of the compound of Formula (I), which may for example be formulated to be isotonic with the blood of the recipient.

The compounds of Formula (I) of the present disclosure may for example be formulated in compositions including those suitable for inhalation to the lung, by aerosol, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the compound of Formula (I) into association with a carrier that constitutes one or more accessory ingredients. In general, the compositions are prepared by bringing the compound of Formula (I) into association with a liquid carrier to form a solution or a suspension, or alternatively, bring the compound of Formula (I) into association with formulation components suitable for forming a solid, optionally a particulate product, and then, if warranted, shaping the product into a desired delivery form. Solid formulations of the present disclosure, when particulate, will typically comprise particles with sizes ranging from about 1 nanometer to about 500 microns. In general, for solid formulations intended for intravenous administration, particles will typically range from about 1 nm to about 10 microns in diameter. The composition may contain compounds of Formula (I) of the present disclosure that are nanoparticulate having a particulate diameter of below 1000 nm, for example, between 5 and 1000 nm, especially 5 and 500 nm, more especially 5 to 400 nm, such as 5 to 50 nm and especially between 5 and 20 nm. In one example, the composition contains compounds of Formula (I) with a mean size of between 5 and 20 nm. In some embodiments, the compound of Formula (I) is polydispersed in the composition, with PDI of between 1.01 and 1.8, especially between 1.01 and 1.5, and more especially between 1.01 and 1.2. In one example, the compounds of Formula (I) are monodispersed in the composition.

It should be understood that in addition to the ingredients particularly mentioned above, the formulations may include other agents conventional in the art having regard to the type of formulation in question, for example, those suitable for oral administration may include flavouring agents.

The compositions of the present disclosure may also include polymeric excipients/additives or carriers, e.g., polyvinylpyrrolidones, derivatised celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-pcyclodextrin and sulfobutylether-β-cyclodextrin), polyethylene glycols, and pectin. The compositions may further include diluents, buffers, citrate, trehalose, binders, disintegrants, thickeners, lubricants, preservatives (including antioxidants), inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the present disclosure are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), and in "Handbook of Pharmaceutical Excipients", Third Ed., Ed. A. H. Kibbe, Pharmaceutical Press, 2000.

Dosages

The amount of active ingredient that is required to achieve a therapeutic effect will, of course, vary with the particular compound, the route of administration, the subject under treatment, including the type, species, age, weight, sex, and medical condition of the subject being treated, and the renal and hepatic function of the subject, and the particular condition, disorder or disease being treated, as well as its severity. An ordinary skilled physician or clinician can readily determine and prescribe the effective amount of the drug required to prevent or treat the condition, disorder or disease.

Dosages of a compound of Formula (I) or salt thereof, when used for the indicated effects, will range between, for example, about 0.01 mg per kg of body weight per day (mg/kg/day) to about 1000 mg/kg/day. In some embodiments, the dosage of a compound of Formula (I) or salt thereof is between about 0.01 and 1000, 0.1 and 500, 0.1 and 100, 1 and 50 mg/kg/day. In some embodiments, the dosage of a compound of Formula (I) or salt thereof is between about 0.01 and 1000 mg/kg/day. In some embodiments, the dosage of a compound of Formula (I) or salt thereof is between about 0.1 and 100 mg/kg/day. In some embodiments, the dosage of a compound of Formula (I) or salt thereof is greater than about 0.01, 0.1, 1, 10, 20, 50, 75, 100, 500, 1000 mg/kg/day. In some embodiments, the dosage of a compound of Formula (I) or salt thereof is greater than about 0.01 mg/kg/day. In some embodiments, the dosage of a compound of Formula (I) or salt thereof is less than about 5000, 1000, 75, 50, 20, 10, 1, 0.1 mg/kg/day. In some embodiments, the dosage of a compound of Formula (I) or salt thereof is less than about 1000 mg/kg/day.

A compound of Formula (I) or salt thereof may for example be administered as a single daily dose, or otherwise the total daily dosage may be administered in divided doses of two, three, or four times daily. In some embodiments, the compound of Formula (I) or salt thereof may be dosed less frequently than once per day, for example once per two days, three days, four days, five days, six days, or once per week.

If administered intravenously, an infusion of the compound over a period of time may be used, for example. Furthermore, a compound of Formula (I) or salt thereof may be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Combination Therapy

Whilst a compound of Formula (I) or salt thereof may be used as the sole active agent in a medicament, as discussed above it is also possible for a compound of Formula (I) or salt thereof to be used in combination with one or more further therapeutic agents. Accordingly, in some embodiments, a compound of Formula (I) or salt thereof is used in combination with one or more further therapeutic agents. The present disclosure therefore also provides a combination of a compound of Formula (I) or salt thereof and a further therapeutic agent. The present disclosure also provides a pharmaceutical composition comprising a combination of a compound of Formula (I) or salt thereof, a further therapeutic agent, and a pharmaceutically acceptable excipient. Such one or more further therapeutic agents may for example be anti-cancer agents. Drugs are often coadministered with other drugs during chemotherapy. In some embodiments, a compound of Formula (I) or salt thereof is used in combination with one or more further anti-cancer agents.

The compound of Formula (I) or salt thereof and the one or more further pharmaceutically active agents may be administered simultaneously, subsequently or separately. For example, they may be administered as part of the same composition, or by administration of separate compositions. The one or more further pharmaceutically active agents may for example be anticancer agents for therapy of pancreatic cancer, colon cancer, cholangiocarcinoma, lung cancer, melanoma, colorectal cancer, brain glioblastoma, liver cancer, or bile duct cancer.

The further therapeutic agents, when employed in combination with a compound of Formula (I) or salt thereof, may be used for example in those amounts indicated in the Physicians' Desk Reference or as otherwise determined by one of ordinary skill in the art.

Synthesis of Compounds of Formula (I)

Numerous synthetic routes to the compounds of Formula (I) can be devised by any person skilled in the art and the possible synthetic routes described below are not intended to be limiting. Possible synthetic routes for the compounds of Formula (I) are shown schematically below. Where appropriate, any initially produced compound of Formula (I) can be converted into another compound of Formula (I) by known methods.

A compound of Formula (I) of the present disclosure may for example be prepared by any suitable method, for example by a) reacting a compound of Formula (II) with a compound of Formula (III)

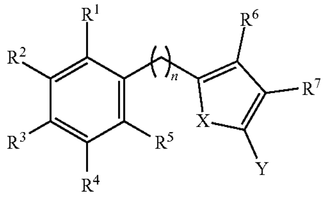

(II)

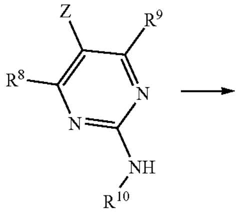

(III)

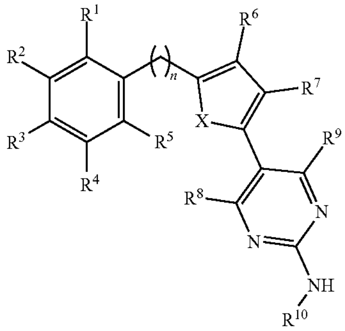

(I)

wherein X and n are as defined above, and $R^1$ to $R^{10}$ are as defined above or may be a protected version thereof, Y is a halide or a pseudohalide (e.g. —OTf), and Z is a boronic acid or boronic ester group (e.g. such as a pinacol ester); and, if required, b) deprotecting the product of step a).

Step a) may be carried out under suitable conditions, e.g. Suzuki coupling conditions, using a base such as potassium phosphate, a palladium catalyst (e.g. Pd(dppf)$Cl_2$ $CH_2Cl_2$, and a suitable solvent such as 1,4-dioxane, e.g. at a temperature in the range of from room temperature to 120° C.

Step b) may be carried out using deprotection conditions suitable for any protecting group or groups used.

A compound of Formula (I) may also be made, for example by a') reacting a compound of Formula (IV) with a compound of Formula (V)

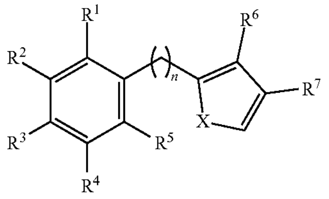

(IV)

-continued

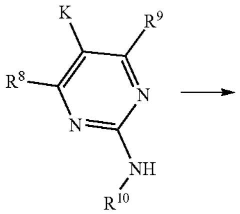

(V)

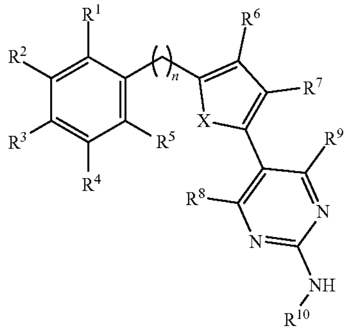

(I)

wherein X and n are as defined above, and $R^1$ to $R^{10}$ are as defined above or may be a protected version thereof, and K is a halide or a pseudohalide (e.g. —OTf); and, if required b') deprotecting the product of step a').

Step a) may be carried out under suitable conditions, e.g. using abase such as potassium acetate, a palladium catalyst (e.g. Pd$(OAc)_2$), and a suitable solvent such as dimethylacetamide, e.g. at a temperature in the range of from 60° C. to 180° C.

Step b') may be carried out using deprotection conditions suitable for any protecting group or groups used.

The present disclosure will now be described with reference to the following examples which illustrate some particular aspects of the present disclosure. However, it is to be understood that the particularity of the following description of the present disclosure is not to supersede the generality of the preceding description of the present disclosure.

EXAMPLES

Example 1: Design of Inhibitor Compounds

Figure 2:
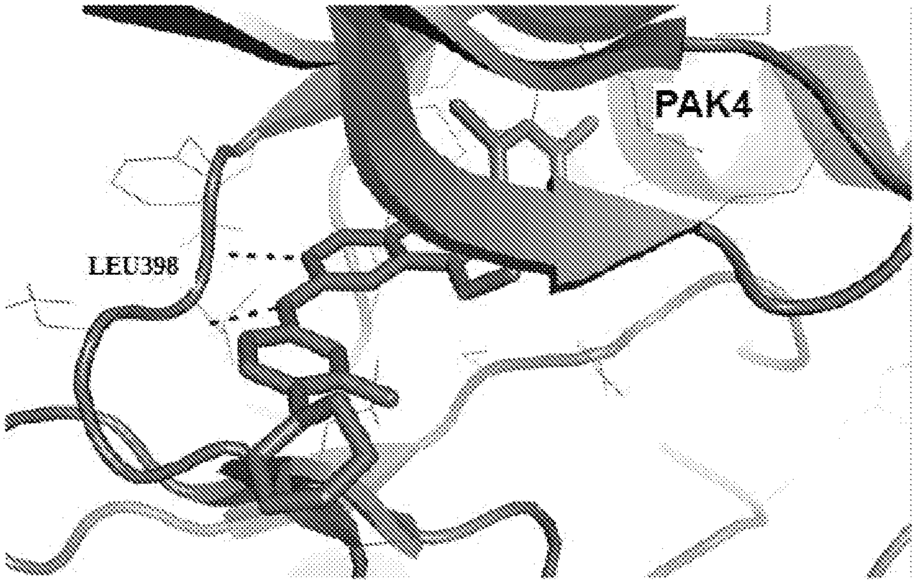
FIG. 2 shows an image of compound FRAX486 bound to PAK4.
Figure 3:
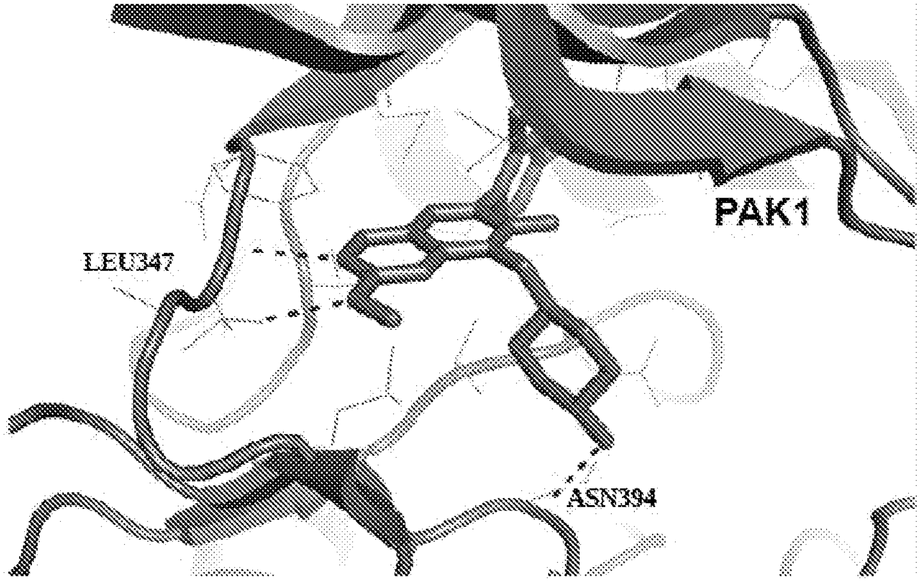
FIG. 3 shows an image of compound G5555 bound to PAK1.

Some inhibitors of PAKs have been developed and the crystal structures of the complexes between these inhibitors and PAK kinases have been available (Rudolph et al, 2015). Using the experimental structures of the inhibitors G-5555 bound to PAK1 (Ndubaku et al, 2015), FRAX486 bound to PAK4 (Zhang et al, 2018) and PF-3758309 to PAK1 (Staben et al, 2014) (as shown in FIGS. 1-3), a new series of compound were designed which could bind into the ATP binding site of PAK1 and PAK4 kinases, so as to inhibit the kinase activities of PAK1 and/or PAK4. These compounds designed included compound Ia, compound Ib, and related structures of Formula (I).

The pyrimidine and —NH of the compounds of Formula (I) are understood to form two typical hydrogen bonds to the backbone of hinge region residue Leu347 of PAK1 and Leu398 of PAK4 kinase catalytic domain, so as to inhibit the ATP-PAK4 binding.

Synthesis Examples

General Methods

All solvents used were commercially available and were used without further purification. Reactions were typically run using anhydrous solvents under an inert atmosphere of nitrogen.

Proton NMR spectra was recorded using a Bruker Plus 400 NMR Spectrometer; The deuterated solvent (DMSO-$d_6$) contained typically 0.03% to 0.05% v/v tetramethylsilane, which was used as the reference signal (set at ™ 0.00 for 1H).

LCMS analyses were performed on a SHIMADZU LCMS consisting of an UFLC 20-AD and LCMS 2020 MS detector. The column was used was a OBD C18 Column, 30×150 mm 5 μm. The instrument using reverse-phase conditions (acetonitrile/water, containing 10 mmol/L TFA).

Example 2: Synthesis of Compound Ia

5-[5-[(2,6-dichloro-4-methoxyphenyl)methyl]furan-2-yl]-N-methylpyrimidin-2-amine

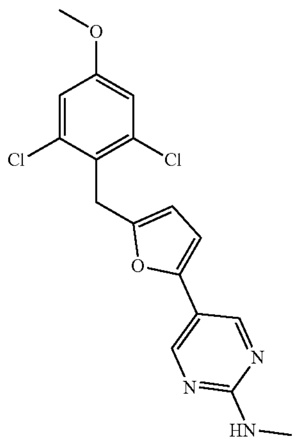

Chemical Formula: $C_{17}H_{15}Cl_2N_3O_2$
Exact Mass: 363
Molecular Weight: 364

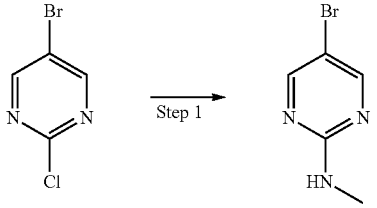

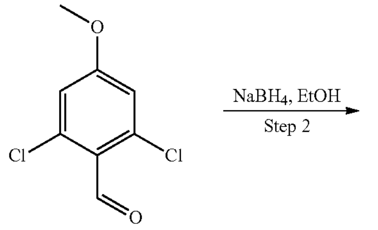

-continued

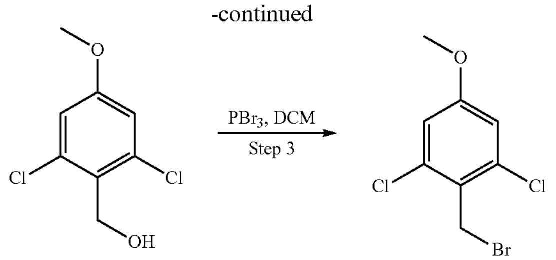

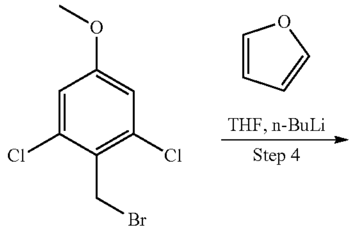

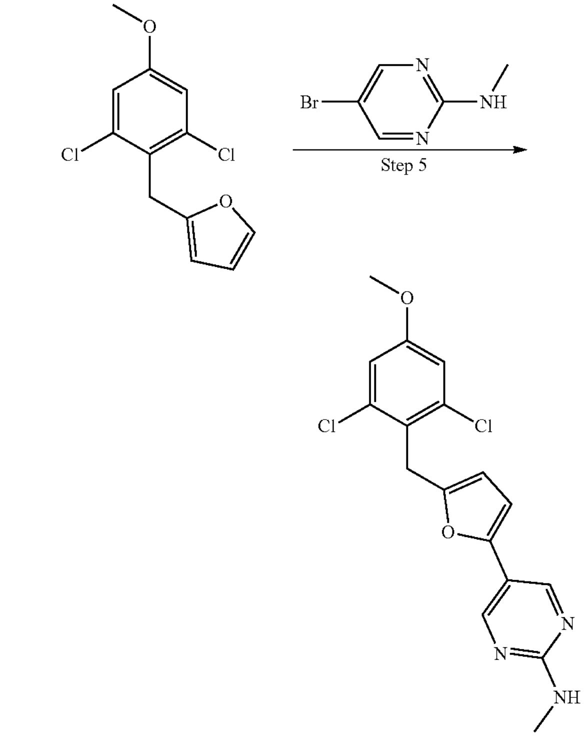

Step 1. 5-Bromo-N-methylpyrimidin-2-amine

A solution of 5-bromo-2-chloropyrimidine (10.0 g, 51.7 mmol) and a solution of $CH_3NH_2$ (31.0 mL, 2M in THF) in EtOH (50.0 mL) was refluxed for 16 h at 80° C. under nitrogen atmosphere. The mixture was allowed to cool down to 25° C. The resulting mixture was concentrated under vacuum. The residue was purified by silica gel column chromatography (eluting with 1:3 ethyl acetate/petroleum ether) to afford 5-bromo-N-methylpyrimidin-2-amine as a white solid (5.20 g, 50%). LCMS (ES, m/z): 188,190 $[M+H]^+$.

Step 2. (2,6-Dichloro-4-methoxyphenyl)methanol $NaBH_4$ (610 mg, 16.1 mmol) was added to a solution of 2,6-dichloro-4-methoxybenzaldehyde (3.00 g, 14.6 mmol) in EtOH (30.0 mL) at 0° C. The resulting mixture was stirred for 3 h at 25° C. The reaction was quenched with $NH_4Cl$ (5 mL, sat.) at 0° C. The resulting mixture was extracted with DCM (3×30 mL). The organic layers were combined, washed with brine (50 mL), dried over anhydrous sodium sulfate, filtered and concentrated under vacuum to give (2,6-dichloro-4-methoxyphenyl)methanol as a white solid (2.80 g, crude). GCMS (ES, m/z): 206 $[M+H]^+$.

Step 3. 2-(Bromomethyl)-1,3-dichloro-5-methoxybenzene

PBr3 (1.46 g, 5.41 mmol) was added to a solution of (2,6-dichloro-4-methoxyphenyl)methanol (2.80 g, 13.5 mmol) in DCM (30.0 mL) at 0° C. The resulting mixture was stirred for 1 h at 0° C. The reaction was quenched with $NaHCO_3$ (5 mL, sat.) at 0° C. The resulting mixture was extracted with DCM (3×30 mL). The organic layers were combined, washed with brine (30 mL), dried over anhydrous sodium sulfate, filtered and concentrated under vacuum. The residue was purified by silica gel column chromatography (eluting with 1:5 ethyl acetate/petroleum ether) to afford to give 2-(bromomethyl)-1,3-dichloro-5-methoxybenzene as an off-white solid (3.40 g, 88%). GCMS (ES, m/z): 268 $[M+H]^+$.

Step 4. 2-[(2,6-Dichloro-4-methoxyphenyl)methyl]furan

A solution of n-BuLi (3.33 mL, 2.5M in THF) was added to a solution of furan (0.76 g, 11.1 mmol) in THF (30.0 mL) at 0° C. under nitrogen atmosphere. The resulting mixture was stirred for 1 h at 25° C. under nitrogen atmosphere. 2-(bromomethyl)-1,3-dichloro-5-methoxybenzene (1.50 g, 5.55 mmol) was added. The resulting mixture was stirred for 16 h at 25° C. under nitrogen atmosphere. The reaction was quenched with $NH_4Cl$ (sat.) (10 mL) at 25° C. The resulting mixture was extracted with EA (3×30 mL). The organic layers were combined, washed with brine (30 mL), dried over anhydrous sodium sulfate, filtered and concentrated under vacuum. The residue was purified by reverse phase chromatography (Column: C18 silica gel; Mobile phase, A: water (containing 0.05% TFA) and B: ACN (0% to 60% in 30 min); Detector: UV 220 nm/254 nm) to afford a crude product. It was further purified via Prep-HPLC (Column, Xselect CSH OBD Column, 30×150 mm 5um; Mobile phase, A: water (containing 0.05% TFA) and B: ACN (55% to 70% in 8 min); Detector, UV 220/254 nm) to give 2-[(2,6-dichloro-4-methoxyphenyl)methyl]furan as a white solid (200 mg, 13%). GCMS (ES, m/z): 256 $[M+H]^+$.

Step 5. 5-[5-[(2,6-Dichloro-4-methoxyphenyl)methyl]furan-2-yl]-N-methylpyrimidin-2-amine A mixture of 2-[(2,6-dichloro-4-methoxyphenyl)methyl]furan (100 mg, 0.389 mmol), 5-bromo-N-methylpyrimidin-2-amine (109 mg, 0.583 mmol), $Pd(OAc)_2$ (8.73 mg, 0.039 mmol) and KOAc (76.3 mg, 0.778 mmol) in DMA (1.00 mL) was stirred for 48 h at 150° C. under nitrogen atmosphere. The mixture was allowed to cool down to 25° C. and purified by reverse phase chromatography (Column: C18 silica gel; Mobile phase, A: water (containing 0.05% TFA) and B: ACN (0% to 60% in 30 min); Detector: UV 220 nm/254 nm) to afford a crude product (20.0 mg). It was further purified via Prep-HPLC (Column, Sunfire Prep C18 OBD Column, 19×250 mm 10 um; Mobile phase, A: water (containing 0.05% TFA) and B: ACN (60% to 85% in 7 min); Detector, UV 220/254 nm). The collected fraction was lyophilized to afford 5-[5-[(2,6-dichloro-4-methoxyphenyl)methyl]furan-2-yl]-N-methylpyrimidin-2-amine as an off-white solid (5.60 mg, 4%). $^1H$-NMR (DMSO-$d_6$, 400 MHz) δ (ppm): 8.93 (s, 2H), 7.32-7.21 (m, 1H), 7.14 (s, 2H), 6.63 (d, J=3.2 Hz, 1H), 6.05 (d, J=3.2 Hz, 1H), 4.20 (s, 2H), 3.80 (s, 3H), 2.82 (d, J=4.4 Hz, 1H). LCMS (ES, m/z): 364 $[M+H]^+$.

Example 3: Synthesis of Compound Ib

5-[5-(2,6-dichloro-4-methoxyphenyl)thiophen-2-yl]-N-methylpyrimidin-2-amine

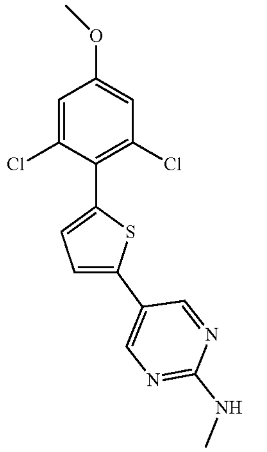

Chemical Formula: $C_{16}H_{13}Cl_2N_3OS$
Exact Mass: 365
Molecular Weight: 366

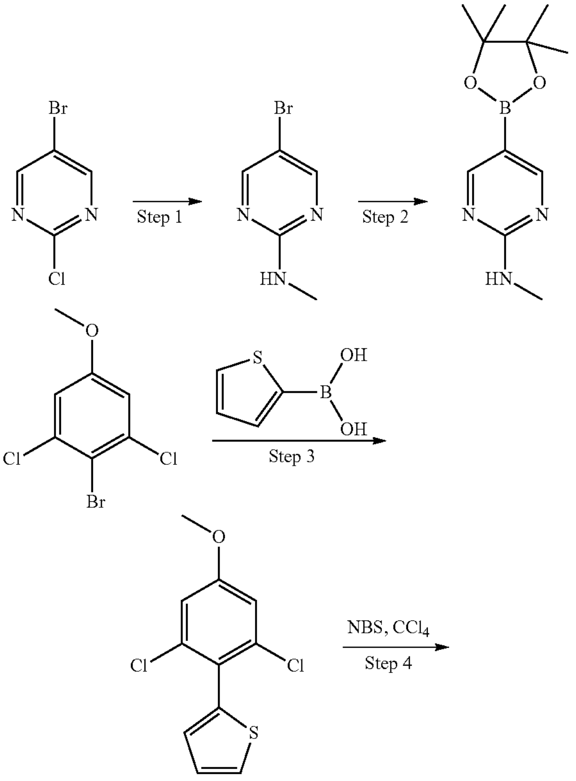

-continued

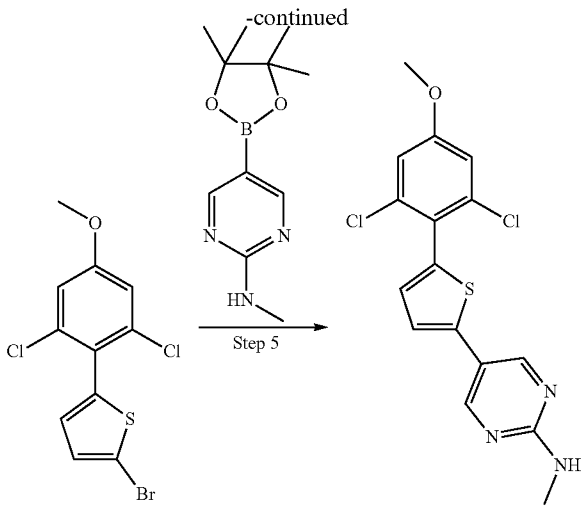

Step 1. 5-Bromo-N-methylpyrimidin-2-amine

A solution of 5-bromo-2-chloropyrimidine (10.0 g, 51.7 mmol) and a solution of $CH_3NH_2$ (31.0 mL, 2M in THF) in EtOH (50.0 mL) was refluxed for 16 h at 80° C. under nitrogen atmosphere. The mixture was allowed to cool down to 25° C. The resulting mixture was concentrated under vacuum. The residue was purified by silica gel column chromatography (eluting with 1:3 ethyl acetate/petroleum ether) to afford 5-bromo-N-methylpyrimidin-2-amine as a white solid (5.20 g, 50%). LCMS (ES, m/z): 188,190 $[M+H]^+$.

Step 2. N-methyl-5-(4,4,5,5-tetramethyl-1,3,2-dioxaborolan-2-yl)pyrimidin-2-amine A mixture of 5-bromo-N-methylpyrimidin-2-amine (1.00 g, 5.31 mmol), 4,4,5,5-tetramethyl-2-(tetramethyl-1,3,2-dioxaborolan-2-yl)-1,3,2-dioxaborolane (1.62 g, 6.38 mmol), $Pd(dppf)Cl_2$ $CH_2Cl_2$ (0.430 g, 0.532 mmol) and KOAc (1.57 g, 15.9 mmol) in 1,4-dioxane (10.0 mL) was stirred for 3 h at 80° C. under nitrogen atmosphere. The mixture was allowed to cool down to 20° C. The reaction was quenched by the addition of water (60 mL). The resulting mixture was extracted with ethyl acetate (3×50 mL). The organic layers were combined, washed with brine (50 mL), dried over anhydrous sodium sulfate, filtered and concentrated under vacuum. The residue was purified by silica gel column chromatography (eluting with 1:2 ethyl acetate/petroleum ether) to afford N-methyl-5-(4,4,5,5-tetramethyl-1,3,2-dioxaborolan-2-yl)pyrimidin-2-amine as a yellow oil (1.30 g, 93%). LCMS (ES, m/z): 236 $[M+H]^+$.

Step 3. 2-(2,6-Dichloro-4-methoxyphenyl)thiophene

A mixture of 2-bromo-1,3-dichloro-5-methoxybenzene (400 mg, 1.56 mmol), thiophen-2-ylboronic acid (240 mg, 1.87 mmol), $Pd(dppf)Cl_2$ $CH_2Cl_2$ (255 mg, 0.313 mmol) and $K_3PO_4$ (995 mg, 4.68 mmol) in 1,4-dioxane (5.00 mL)/$H_2O$ (2.50 mL) was stirred for 5 h at 80° C. under nitrogen atmosphere. The mixture was allowed to cool down to 25° C. The resulting mixture was diluted with water (20 mL) and extracted with EA (3×30 mL). The organic layers were combined, washed with brine (30 mL), dried over anhydrous sodium sulfate, filtered and concentrated under vacuum. The residue was purified by silica gel column chromatography (eluting with 1:2 ethyl acetate/petroleum ether) to afford 2-(2,6-dichloro-4-methoxyphenyl)thiophene as a yellow oil (130 mg, 30%). GCMS (ES, m/z): 258 $[M+H]^+$.

Step 4. 2-Bromo-5-(2,6-dichloro-4-methoxyphenyl)thiophene

A solution of 2-(2,6-dichloro-4-methoxyphenyl)thiophene (130 mg, 0.502 mmol) and NBS (107 mg, 0.602 mmol) in $CCl_4$ (2.00 mL) was stirred for 16 h at 60° C. under nitrogen atmosphere without light. The mixture was allowed to cool down to 25° C. and concentrated under vacuum. The residue was purified by silica gel column chromatography (eluting with 1:3 ethyl acetate/petroleum ether) to afford 2-bromo-5-(2,6-dichloro-4-methoxyphenyl)thiophene as a yellow solid (50.0 mg, 28%). GCMS (ES, m/z): 336 $[M+H]^+$.

Step 5. 5-[5-(2,6-Dichloro-4-methoxyphenyl)thiophen-2-yl]-N-methylpyrimidin-2-amine A solution of 2-bromo-5-(2,6-dichloro-4-methoxyphenyl) thiophene (45.0 mg, 0.133 mmol), N-methyl-5-(4,4,5,5-tetramethyl-1,3,2-dioxaborolan-2-yl)pyrimidin-2-amine (37.5 mg, 0.160 mmol), $Pd(dppf)Cl_2$ $CH_2Cl_2$ (21.7 mg, 0.027 mmol) and $K_3PO_4$ (84.7 mg, 0.399 mmol) in 1,4-dioxane (1.00 mL) and $H_2O$ (0.50 mL) was stirred for 3 h at 80° C. under nitrogen atmosphere. The reaction mixture was cooled to 25° C. and concentrated under vacuum. The residue was purified by Pre-TLC (eluting with 1:4 ethyl acetate/petroleum ether) to give a crude product. The crude product was purified via Prep-HPLC (Column, XBridge Shield RP18 OBD Column, 19×150 mm 5 um; Mobile phase, A: water (containing 0.05% TFA) and B: ACN (50% to 75% in 8 min); Detector, UV 220/254 nm). The collected fraction was lyophilized to afford 5-[5-(2,6-dichloro-4-methoxyphenyl)thiophen-2-yl]-N-methylpyrimidin-2-amine as an off-white solid (5.10 mg, 10%). $^1$H-NMR (DMSO-$d_6$, 400 MHz) δ (ppm): 8.74 (s, 2H), 7.54-7.39 (m, 2H), 7.23 (s, 2H), 7.09-6.98 (m, 1H), 3.86 (s, 3H), 2.85 (s, 3H). LCMS (ES, m/z): 366 $[M+H]^+$ Example 3a: Synthesis of Compound Ic

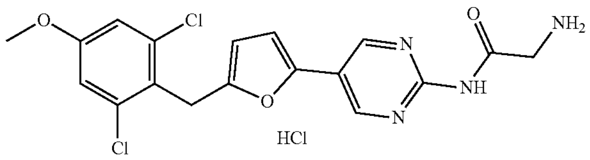

HCl

Chemical Formula: $C_{18}H_{17}Cl_3N_4O_3$
Exact Mass: 442.04
Molecular Weight: 443.71

-continued

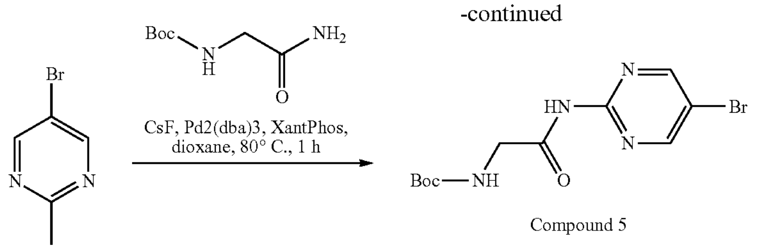

Compound 5

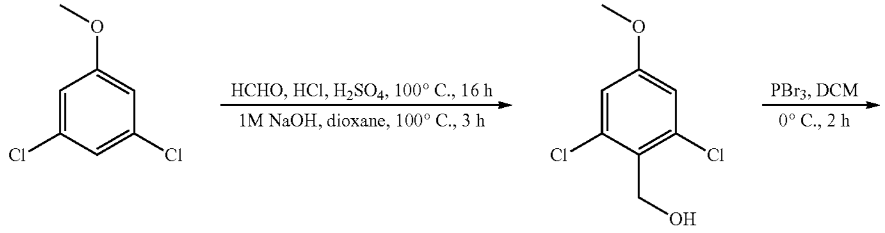

Compound 1

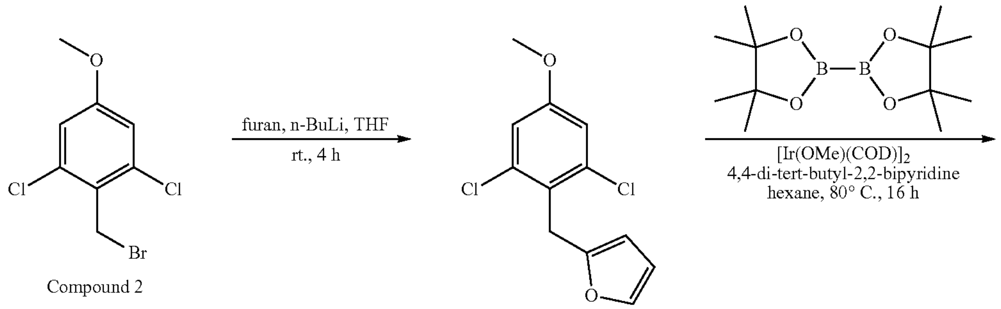

Compound 2

Compound 3

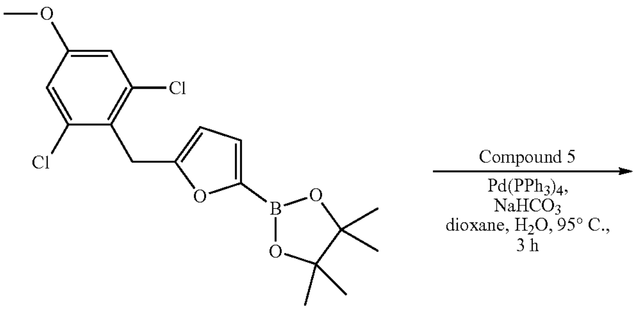

Compound 4

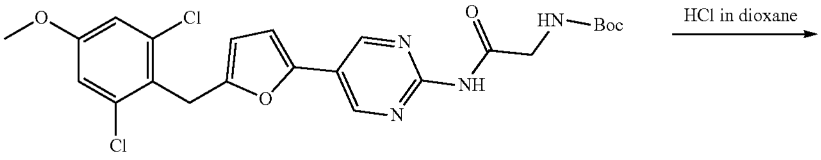

Compound 6

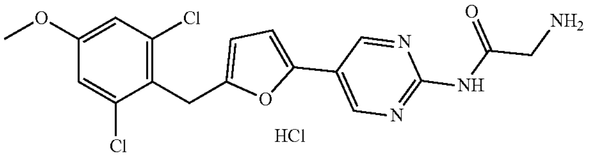

Compound 7

Synthesis of Compound 1

To a mixture of 3,5-dichloroanisole (18 g, 97.6 mmol, 1.00 equiv), Paraformaldehyde (4.26 g, 128 mmol, 1.31 equiv) and conc. hydrochloric acid (180 mL) was added conc. sulfuric acid (1.80 mL) at room temperature. After refluxing at 100° C. for 16 hours, the mixture was cooled to room temperature. he resulting mixture was extracted with ethyl acetate (5×50 mL). The organic layer was dried over anhydrous sodium sulfate, filtered and concentrated under reduced pressure. To the residue were added 1,4-dioxane (100 mL) and a sodium hydroxide aqueous solution (203 mL, 1 M). The mixture was refluxed at 100° C. for 3 hours. The reaction solution was cooled to room temperature, followed by extraction with DCM (5×50 mL). The organic layer was dried over anhydrous sodium sulfate, filtered and then concentrated under reduced pressure. The residue was purified by silica gel column chromatography (eluting with 85:15 PE/EA) to afford (2,6-dichloro-4-methoxyphenyl) methanol (5.6 g, 26.6%) as a white solid. GCMS (ES, m/z): 206,208.

Synthesis of Compound 2

To a solution of (2,6-dichloro-4-methoxyphenyl)methanol (5.6 g, 26.0 mmol, 1.00 equiv) in DCM (76 mL) was added PBr3 (2.81 g, 9.97 mmol, 0.40 equiv) at 0° C. The reaction mixture was stirred for 2 h at 0° C. The reaction was poured into icy water (50 mL). The resulting mixture was extracted with $CH_2Cl_2$ (3×50 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE/EA (20:1) to afford 2-(bromomethyl)-1,3-dichloro-5-methoxybenzene (6.9 g, 94.5%) as a white solid. GCMS (ES, m/z): 268, 270, 272.

Synthesis of Compound 3

To a solution of furan (3.50 g, 49.4 mmol, 2.01 equiv) in tetrahydrofuran (35 mL) was added n-BuLi (25 mL, 50 mmol, 2.03 equiv) dropwise at 0° C. The reaction mixture was stirred for 3 h at room temperature. A solution of 2-(bromomethyl)-1,3-dichloro-5-methoxybenzene (6.9 g, 24.5 mmol, 1.00 equiv) in THF (10 mL) was added dropwise at 0° C. The mixture was stirred for 1 h room temperature. The reaction was quenched with sat. $NH_4Cl$ (aq.) at room temperature. The resulting mixture was extracted with EA (3×50 mL). The combined organic layers were washed with brine (2×50 mL), dried over anhydrous $Na_2SO_4$. After filtration, the filtrate was concentrated under reduced pressure. The residue was purified by silica gel chromatography (eluting with pure PE) to give 2-[(2,6-dichloro-4-methoxyphenyl)methyl]furan (1.00 g, 15.4%) as a white solid. LCMS (ES, m/z): 257,259 $[M+H]^+$.

Synthesis of Compound 4

A solution of 2-[(2,6-dichloro-4-methoxyphenyl)methyl] furan (0.96 g, 3.61 mmol, 1.1 equiv), bis(pinacolato)diboron (0.85 g, 3.28 mmol, 1.00 equiv), (1,5-CYCLOOCTADIENE)(METHOXY)IRIDIUM(I) DIMERDi-m-methoxobis (1,5-cyclooctadiene)diiridium (I) (23 mg, 0.033 mmol, 0.01 equiv) and 4,4'-di-tert-butyl-2,2'-bipyridine (26 mg, 0.094 mmol, 0.03 equiv) in hexane (10 mL) was stirred at 80° C. for 1 h. The mixture was cooled down to room temperature. The mixture was concentrated under reduced pressure. The residue was purified by silica gel chromatography (eluting with 1:1 PE/DCM) to give 2-{5-[(2,6-dichloro-4-methoxyphenyl)methyl]furan-2-yl}-4,4,5,5-tetramethyl-1,3,2-dioxaborolane (900 mg, 68.0%) as a white solid. LCMS (ES, m/z): 383, 385 $[M+H]^+$.

Synthesis of Compound 5

A mixture of 5-bromo-2-iodopyrimidine (400 mg, 1.35 mmol, 1.00 equiv), tert-butyl N(carbamoylmethyl)carbamate (235 mg, 1.35 mmol, 1 equiv), $Pd_2(dba)_3$ (123 mg, 0.135 mmol, 0.1 equiv), XantPhos (78 mg, 0.135 mmol, 0.1 equiv), CsF (409 mg, 2.70 mmol, 2 equiv), and dioxane (5 mL) was stirred for 1 h at 80° C. under nitrogen atmosphere. The resulting mixture was cooled down to room temperature, filtered, the filtrate was concentrated under vacuum. The residue was purified directly via reverese phase chromatography (Column: C18 silica gel; Mobile phase, A: water (containing 10 mmoL/L $NH_4HCO_3$) and B: $CH_3CN$; Gradient: 0% to 70% in 30 min; Detector: 220 nm) to give tert-butyl N-{[(5-bromopyrimidin-2-yl)carbamoyl] methyl}carbamate (470 mg, 99.0%) as an off-white solid. LCMS (ES, m/z): 331, 333$[M+H]^+$.

Synthesis of Compound 6

A mixture of 2-{5-[(2,6-dichloro-4-methoxyphenyl) methyl]furan-2-yl}-4,4,5,5-tetramethyl-1,3,2-dioxaborolane (252 mg, 0.624 mmol, 1.10 equiv), tert-butyl N-{[(5-bromopyrimidin-2-yl)carbamoyl]methyl}carbamate (163 mg, 0.568 mmol, 1.00 equiv), $Pd(PPh_3)_4$ (68 mg, 0.057 mmol, 0.1 equiv), $NaHCO_3$ (120 mg, 1.42 mmol, 2.5 equiv), dioxane (5 mL) and $H_2O$ (1 mL) was stirred for 3 h at 90° C. under nitrogen atmosphere. The resulting mixture was allowed to cooled down to room temperature. The mixture was filtered, the filtrated was purified via reverse phase chromatography (Column: C18 silica gel; Mobile phase, A: water (containing 10 mmoL/L $NH_4HCO_3$) and B: $CH_3CN$; Gradient: 0% to 70% in 30 min; Detector: 220 nm) to give tert-butyl N-{1[(5-{5-[(2,6-dichloro-4-methoxyphenyl) methyl]furan-2-yl}pyrimidin-2-yl)carbamoyl] methyl}carbamate (57 mg, 15.6%) as an off-white solid. LCMS (ES, m/z): 507, 509$[M+H]^+$.

Synthesis of Compound 7

To a stirred mixture of tert-butyl N-{[(5-{5-[(2,6-dichloro-4-methoxyphenyl)methyl]-furan-2-yl}pyrimidin-2-yl)carbamoyl]methyl}carbamate (57 mg, 0.089 mmol, 1.00 equiv) in DCM (5 mL) was added HCl (gas) in 1,4-dioxane (1 mL, 4M) dropwise at 0° C. The resulting mixture was stirred for 1 h at 0° C. under nitrogen atmosphere. The resulting mixture was concentrated under vacuum. The residue was purified by reverse phase chromatography (Column, C18 silica gel; Mobile phase, A: water (containing 0.05% HCl) and B: MeCN (30% to 45% in 10 min) to afford 2-amino-N-(5-{5-[(2,6-dichloro-4-methoxyphenyl)methyl] furan-2-yl}pyrimidin-2-yl)acetamide hydrochloride (19 mg, 46.0%). 1H-NMR (DMSO-d6, 300 MHz) δ (ppm): 11.2-11.40 (br s, 1H), 8.92 (s, 2H), 8.25 (s, 2H), 7.16 (s, 2H), 7.03 (s, 1H), 6.18 (s, 1H), 4.26 (s, 3H), 4.07 (s, 2H), 3.81 (s, 3H). LCMS (ES, m/z): 407,409 $[M+H]^+$.

Example 3b: Synthesis of Compound Id

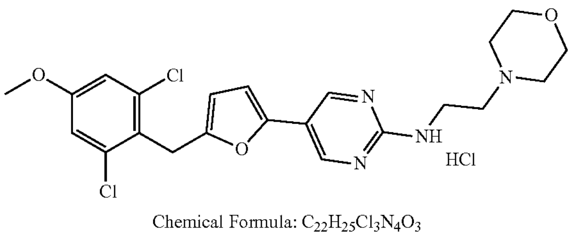

Chemical Formula: $C_{22}H_{25}Cl_3N_4O_3$
Exact Mass: 498.10
Molecular Weight: 499.82

-continued

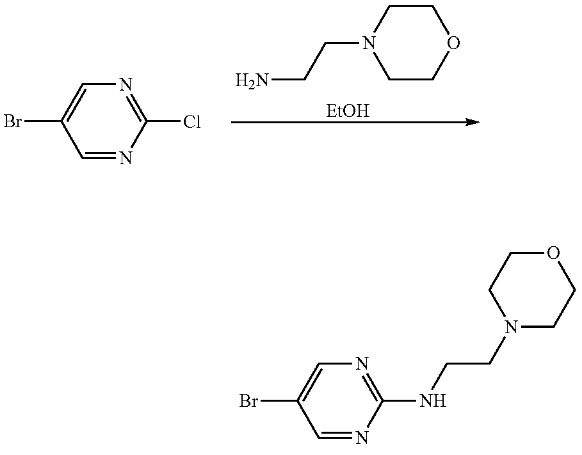

1

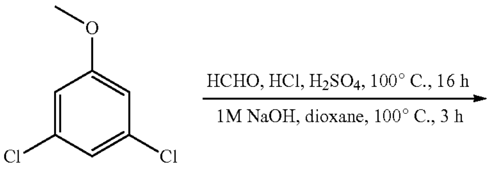

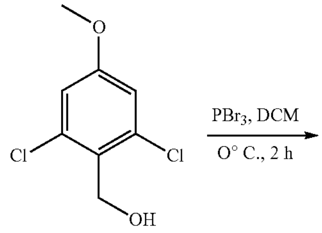

2

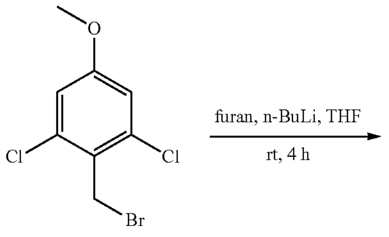

3

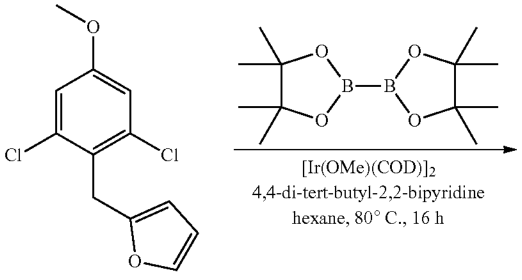

4

-continued

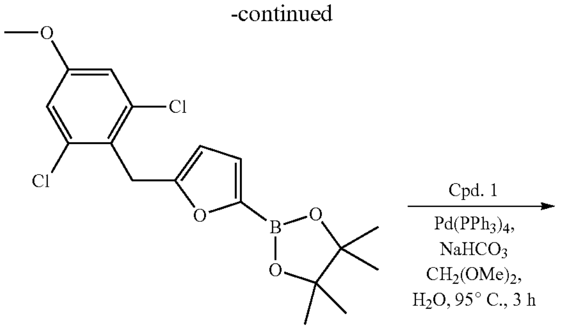

5

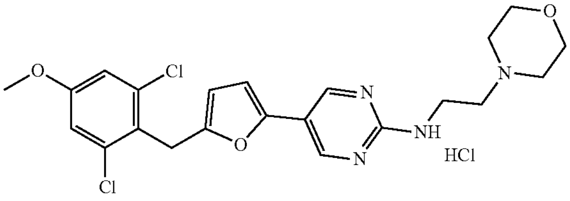

6

Synthesis of Compound 1

A mixture of 5-bromo-2-chloropyrimidine (1 g, 5.12 mmol, 1.00 equiv) and 2-morpholinoethan-1-amine (885 mg, 6.81 mmol, 1.33 equiv) in EtOH (10 mL) was stirred for overnight at 100° C. The mixture was cooled down to room temperature, concentrated under vacuum. The residue was washed with 20/1 PE/EA to give 5-bromo-N-(2-morpholinoethyl)pyrimidin-2-amine (1.2 g, 82%) as a white solid. LCMS (ES, m/z): 287, 289 $[M+H]^+$.

Synthesis of Compound 2

To a mixture of 3,5-dichloroanisole (180 g, 1.02 mol, 1.00 equiv), Paraformaldehyde (40.0 g, 1.33 mol, 1.31 equiv) and conc. hydrochloric acid (1.80 L) was added conc. sulfuric acid (18.0 mL) at room temperature. After refluxing at 100° C. for 16 hours, the mixture was cooled to room temperature. The resulting mixture was extracted with ethyl acetate (5×500 mL). The organic layer was dried over anhydrous sodium sulfate, filtered and concentrated under reduced pressure. To the residue were added 1,4-dioxane (1.00 L) and a sodium Hydroxide aqueous (2.03 L, 1 M). The mixture was refluxed at 100° C. for 3 hours. The reaction solution was cooled to room temperature, followed by extraction with DCM (5×500 mL). The organic layer was dried over anhydrous sodium sulfate, filtered and then concentrated under reduced pressure. The residue was purified by silica gel column chromatography (eluting with 85:15 PE/EA) to afford (2,6-dichloro-4-methoxyphenyl)methanol (56 g, 25.5%) as a white solid. GCMS (ES, m/z): 206, 208.

Synthesis of Compound 3

To a solution of (2,6-dichloro-4-methoxyphenyl)methanol (56.0 g, 270 mmol, 1.00 equiv) in DCM (764 mL, 8.99 mol, 44.4 equiv) was added PBr3 (29.3 g, 108 mmol, 0.40 equiv) at 0° C. The reaction micture was stirred for 2 h at 0° C. The reaction was poured into icy water (500 mL). The resulting mixture was extracted with $CH_2Cl_2$ (3×500 mL). The combined organic layers were washed with brine (2×500 mL), dried over anhydrous $Na_2SO_4$. After filtration, the filtrate was concentrated under reduced pressure. The residue was purified by silica gel column chromatography, eluted with PE/EtOAc (20:1) to afford 2-(bromomethyl)-1,3-dichloro-5-methoxybenzene (69.5 g, 95.2%) as a white solid. GCMS (ES, m/z): 268, 270, 272.

Synthesis of Compound 4

To a solution of furan (35.0 g, 514 mmol, 2.00 equiv) in tetrahydrofuran (350 mL) was added n-BuLi (206 mL, 515 mmol, 2.00 equiv) dropwise at 0° C. The reaction mixture was stirred for 3 h at room temperature. A solution of 2-(bromomethyl)-1,3-dichloro-5-methoxybenzene (69.5 g, 257 mmol, 1.00 equiv) in THF (100 mL) was added dropwise at 0° C. The mixture was stirred for 1 h room temperature. The reaction was quenched with sat. $NH_4Cl$ (aq.) at room temperature. The resulting mixture was extracted with EtOAc (3×500 mL). The combined organic layers were washed with brine (2×500 mL), dried over anhydrous $Na_2SO_4$. After filtration, the filtrate was concentrated under reduced pressure. The residue was purified by silica gel chromatography (eluting with pure PE) to give 2-[(2,6-dichloro-4-methoxyphenyl)methyl]furan (10.4 g, 15.1%) as a white solid. LCMS (ES, m/z): 257, 259 $[M+H]^+$.

Synthesis of Compound 5

A solution of 2-[(2,6-dichloro-4-methoxyphenyl)methyl] furan (10.4 g, 40.5 mmol, 1.10 equiv), bis(pinacolato) diboron (9.36 g, 36.9 mmol, 1.00 equiv), [Ir(OMe)(COD)]2 (CAS: 12148-71-9) (366 mg, 0.552 mmol, 0.01 equiv), 4,4'-Di-tert-butyl-2,2'-bipyridine (297 mg, 1.11 mmol, 0.03 equiv) and hexane (96 mL) was stirred at 80° C. for 1 h. The mixture was cooled down to room temperature. The mixture was concentrated under reduced pressure. The residue was purified by silica gel chromatography (eluting with 1:1 PE/DCM) to give 2-[5-[(2,6-dichloro-4-methoxyphenyl) methyl]furan-2-yl]-4,4,5,5-tetramethyl-1,3,2-dioxaborolane (9.5 g, 64.6%) as a white solid. LCMS (ES, m/z): 383, 385 $[M+H]^+$.

Synthesis of Compound 6

A mixture of 2-{5-[(2,6-dichloro-4-methoxyphenyl) methyl]furan-2-yl}-4,4,5,5-tetramethyl-1,3,2-dioxaborolane (252 mg, 0.624 mmol, 1.10 equiv), 5-bromo-N-(2-morpholinoethyl)pyrimidin-2-amine (163 mg, 0.568 mmol, 1.00 equiv), $Pd(PPh_3)_4$ (68 mg, 0.057 mmol, 0.1 equiv), $NaHCO_3$ (120 mg, 1.42 mmol, 2.5 equiv), dioxane (5 mL) and $H_2O$ (1 mL) was stirred for 3 h at 90° C. under nitrogen atmosphere. The resulting mixture was allowed to cooled down to room temperature. The mixture was filtered, the filtrated was concentrated under vacuum. The residue was purified via reverse phase chromatography (Column: C18 silica gel; Mobile phase, A: water (containing 5 mmoL/L HCl) and B: $CH_3CN$; Gradient: 0% to 50% in 30 min; Detector: 220 nm) to give 5-(5-(2,6-dichloro-4-methoxybenzyl)furan-2-yl)-N-(2-morpholinoethyl)pyrimidin-2-amine hydrochloride (30 mg, 10.2%) as a white solid. LCMS (ES, m/z): 463,465 $[M+H]^+$. $^1H$-NMR (DMSO-$d_6$, 400 MHz) δ (ppm): 10.87 (br s, 1H), 8.60 (s, 2H), 7.71 (br s, 1H), 7.14 (s, 2H), 6.71 (s, 1H), 6.08 (s, 1H), 4.20 (s, 2H), 4.04-3.94 (m, 2H), 3.84-3.73 (m, 7H), 3.60-3.49 (m, 2H), 3.33-3.27 (m, 2H), 3.19-3.03 (m, 2H).

Example 4: Biological Testing of Compound Ia

Control Compound

PF3758309 is an established PAK inhibitor, which is a competitive inhibitor of PAK kinases developed by Pfizer (see Murray et al) and entered into clinical development. PF3758309 is not a selective inhibitor, as it inhibits not only PAKs 1-6, but also off target kinases such as AMPKa1, AMPKa2, CDK7, CHK1, CHEK2, MARK3, PKC0, RSK1, RSK2, TSSK1, Yes and Ret (Semenova and Chernoff, 2017), and was eventually withdrawn from clinical trials. The structure of PF3758309 is provided below.

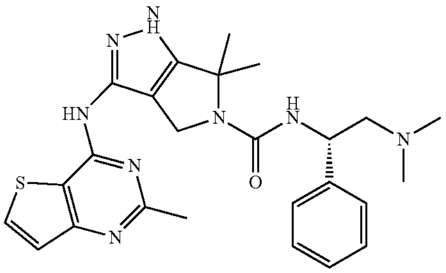

PF3758309

Cell-Free Kinase Assay

Figure 4:
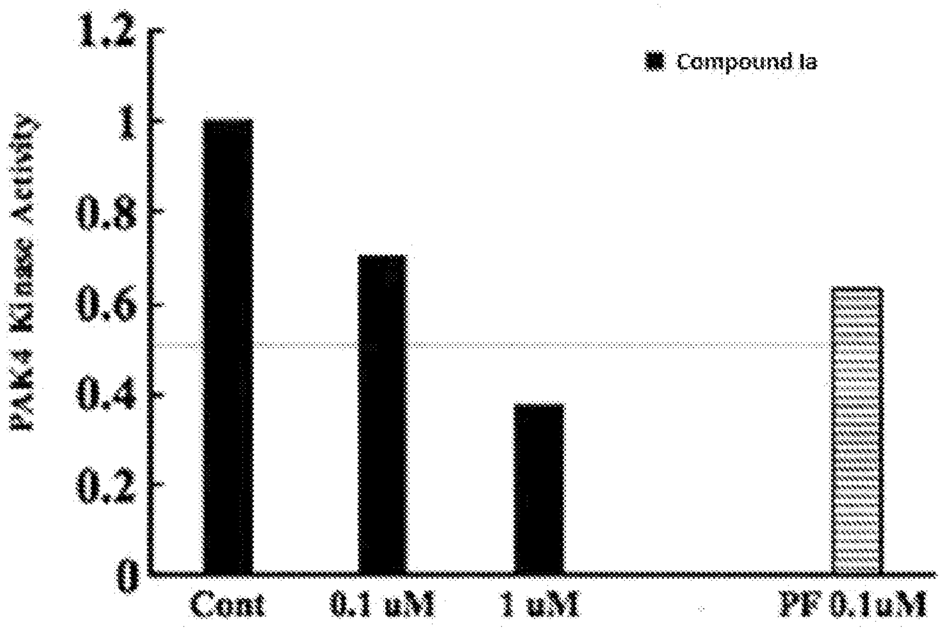
FIG. 4 shows a chart showing PAK4 kinase activity at different concentrations of compound Ia in a cell-free kinase assay, together with a negative and positive control (PF03758309).
Figure 5:
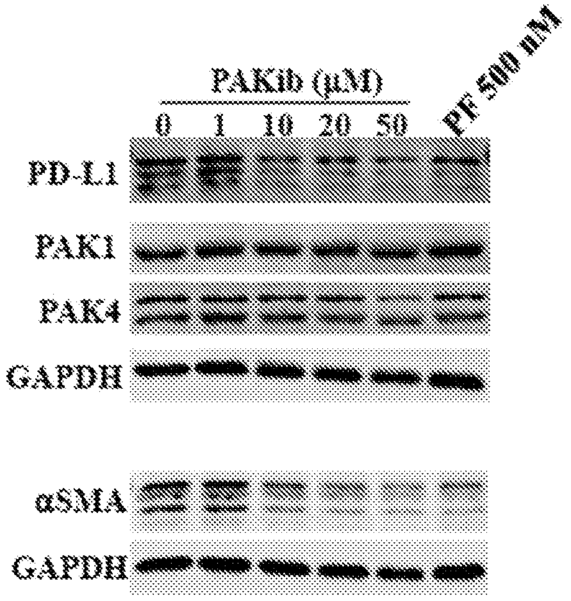
FIG. 5 shows a Western Blot demonstrating that Compound Ia dose-dependently inhibited the expression of PD-L1 in DLD1 cells.

In a cell-free kinase assay (Murray B W, Guo C, Piraino J, et al, Proc. Natl. Acad. Sci. USA 2010; 107:9446), compound Ia was found to inhibit PAK4 kinase with IC50 of 0.2-0.5 uM, comparable to control compound PF3758309 (see FIG. 4). Moreover, compound Ia did not show significant effect on the kinase activity of PAK1, making it a selective PAK4 inhibitor for cancers such as pancreatic ductal adenocarcinoma (Wang et al, 2018).

Inhibition of Different Cancer Cell-Lines

Pancreatic cancer cell lines MiaPaCa-2, PANC1 (human), TB33117 (mouse), and KPCWT833 were used to test the effect of Compound Ia on cell proliferation. PANC1 and TB33117 cell lines express high levels of PAK1 and PAK4, while MiaPaCa-2 cell has low levels of PAK1 and PAK4 (Yeo, 2014 and unpublished data). Compounds Ia has been found to inhibit the cell proliferation of PANC1 and TB33117 with IC50 of 1.11 uM and 1.72 uM respectively, while its effect on MiaPaCa-2 is much weaker (IC50=8.29 uM). The control compound PF375803 was found to inhibit both PAK1 and PAK4, with IC50 of cell proliferation detected at 0.087 uM for MiaPaCa-2, 0.5 uM for PANC1 and 0.805 uM for TB33117, respectively. Compound Ia was also shown to inhibit colorectal cell line MC-38, brain glioblastoma cancer cell like U-87, melanoma cell line B16F1, liver cell line HepG2, and bile duct cancer cell line EIG-1 at low to sub-micromolar IC50 values.

IC50 of Cell Proliferation by Compound Ia and PF375803 (uM)

| Cell | Compound Ia IC50 (uM) | PF3758309 IC50 (uM) |
|---|---|---|
| PANC1 (pancreatic cancer) | 1.11 ± 0.25 | 0.5 ± 0.07 |
| TB33117 (pancreatic cancer) | 1.72 ± 1.45 | 0.805 ± 0.155 |
| MiaPaCa-2 (pancreatic cancer) | 8.29 ± 1.81 | 0.087 ± 0.015 |
| KPCWT833 (pancreatic cancer) | 1.23 ± 0.39 | |

-continued

| Cell | Compound Ia IC50 (uM) | PF3758309 IC50 (uM) |
|---|---|---|
| MC-38 (colon cancer) | 0.46 ± 0.39 | |
| U-87 (brain tumour) | 6.55 ± 3.55 | |
| B16F10 (skin cancer) | 13.34 | |
| HepG2 (liver cancer) | 3.76 ± 0.66 | |
| EIG-1 (cholangiocarcinoma) | 4.63 | |

Compound Ia has been shown to be able to inhibit the cell proliferation of pancreatic cancer cells PANC1 and TB33117 at IC50 of 1.0-2.0 uM. Compound Ta has also been shown to inhibit the proliferation of colon cancer cells, brain tumour cells, skin cancer cells, liver cancer cells, and cholangiocarcinoma cells.

Example 5: Effects of Compound Ta on PD-L1 Expression

Cells from a colorectal cancer cell line (DLD-1) were incubated with Compound Ia (0, 1, 10, 20, 50 μM), or with compound PF-3758309 (500 nM) for 24 h. At the end of 24 h culture, the medium was removed from the cells, and the cells were washed once with PBS. The cells were lysed in SDS-sample buffer. The resultant cell lysates were subjected to 10% SDS-PAGE to separate the proteins with different molecular weights, which then were blotted with antibodies against PD-L1, PAK1, PAK4, α-SMA and GAPDH.

Compound Ia was shown to dose-dependently inhibit the expression of PD-L1 in the colorectal cancer cell line DLD-1. This was associated with a reduced expression of PAK4 and alpha smooth muscle actin (α-SMA). Compound Ta reduced the expression of PD-L1 to a comparable level of PD-L1 when inhibited by PF-3758309, a pan-PAK inhibitor.

The inhibitory effect of Compound Ta on the expression of PD-L1 in cancer cells is expected to decrease the binding of PD-L1 to PD-1 on the surface of T cells, and therefore facilitate the effect of immune checkpoint inhibitors.

Example 5a: Effects of Compound Ia on CHEK2 Inhibition

The effects of Compound Ia on CHEK2 kinase activity was assessed using an ADP-Glo kinase assay kit purchased from Promega (Sydney, NSW, Australia). The assay was undertaken in accordance with the manufacturer's instructions.

Figure 6:
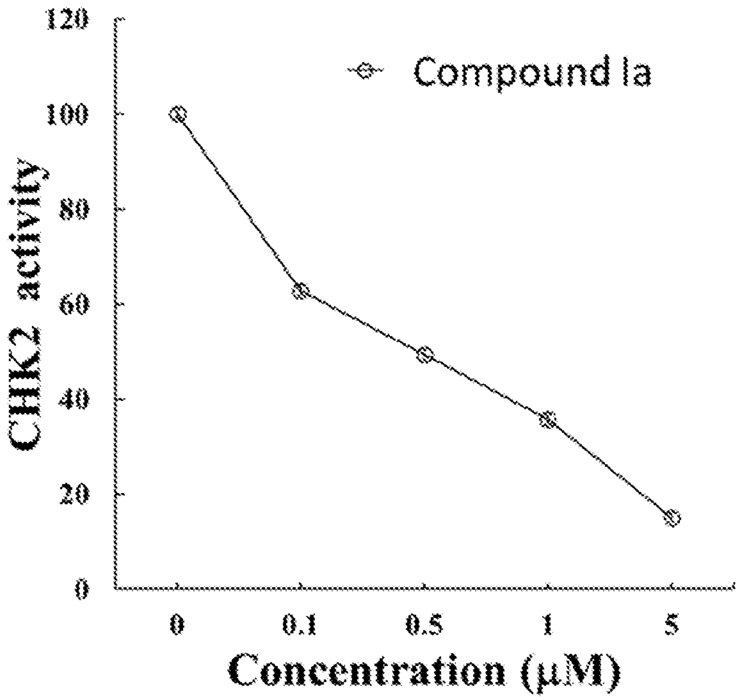
FIG. 6 shows the efficacy of Compound Ia on CHEK2 inhibition.

The results, shown in FIG. 6, demonstrate that Compound Ia is able to inhibit CHEK2 with an IC50 value of 737 nM.

Example 6: Efficacy of Compound Ia in Combination with Gemcitabine

The in vivo efficacy of Compound Ia in combination with anticancer agent, Gemcitabine, was assessed.

Male C57Bl6 (6-week-old) were subcutaneously injected KPC833 cells (50,000 cells/100 ul) at the back of a hind leg. When tumour volume reached 50 or 100 $mm^3$, PAK227 (40 mg/Kg) was given by subcutaneous injection every other day, and gemcitabine 25 or 50 mg/Kg) was given by intraperitoneal injection every 4 days for 3 weeks or more. Tumour volume was measured using a calliper. Tumour weight was measured at the end of experiments.

The results, shown in FIG. 7, demonstrate that combination treatment of Compound Ia and Gemcitabine, for a duration of both 21 days (FIG. 7*a*) and 31 days (FIG. 7*b*), caused regression of pancreatic tumour growth as evidenced by a decrease in tumour volume compared to untreated control tumours. Beneficially, this tumour regression was observed without increased toxicity (e.g., no body weight loss was observed).

Figure 7A:
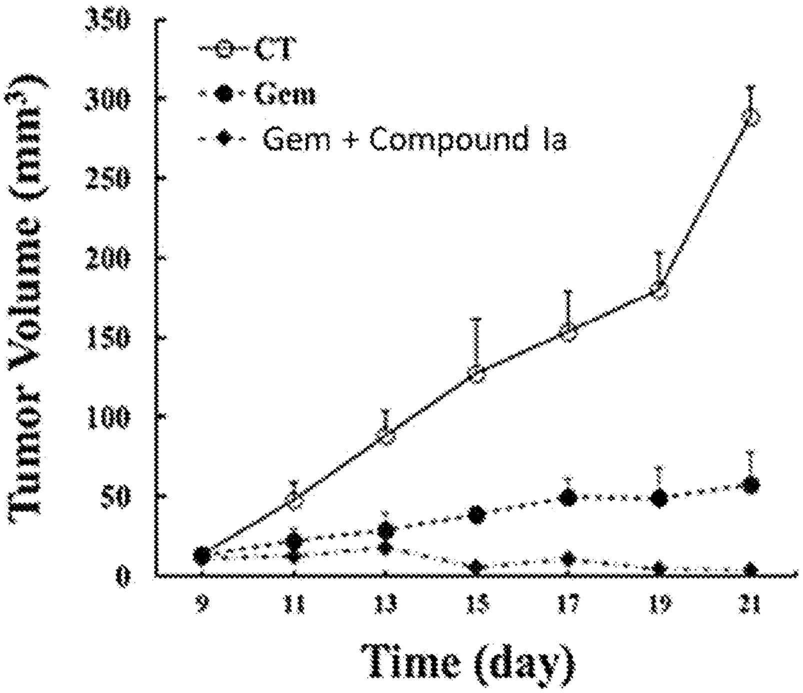
FIG. 7A shows the efficacy of Gemcitabine, alone and in combination with Compound Ia, against tumour volume over 21 days.
Figure 7B:
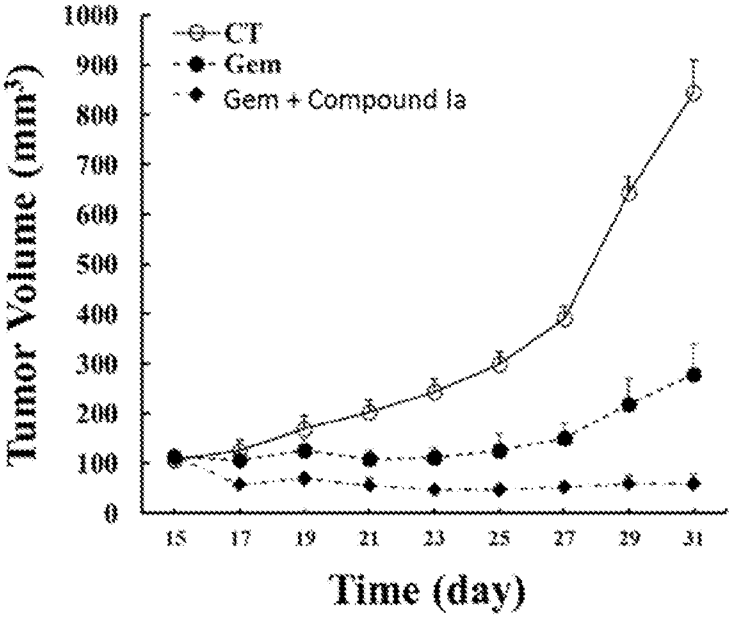
FIG. 7B shows the efficacy of Gemcitabine, alone and in combination with Compound Ia, against tumour volume over 31 days.
Figure 7C:
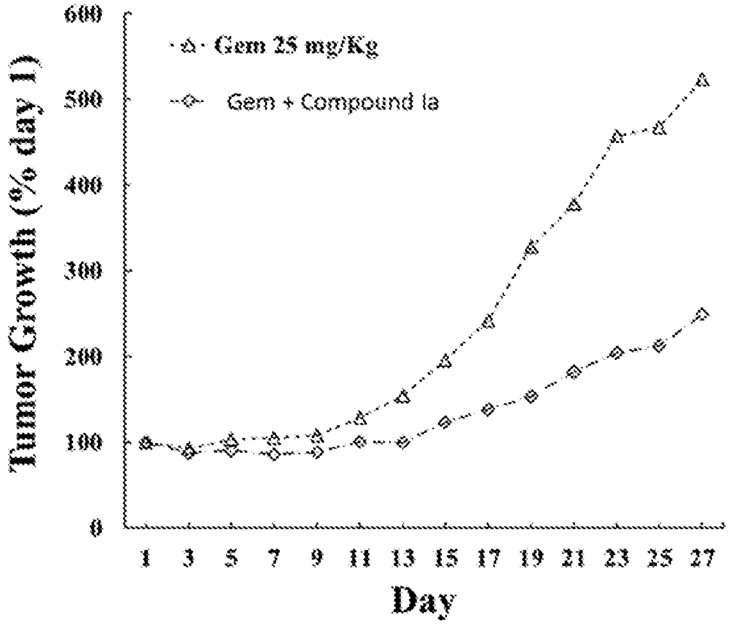
FIG. 7C shows the efficacy of Gemcitabine, alone and in combination with Compound Ia, against advanced tumours (size=100 $mm^3$).

The combination treatment of Compound Ia and Gemcitabine also demonstrated improved efficacy compared to Gemcitabine treatment alone, when tested against advanced tumours (size=100 $mm^3$), as shown in FIG. 7*c*.

Figure 7D:
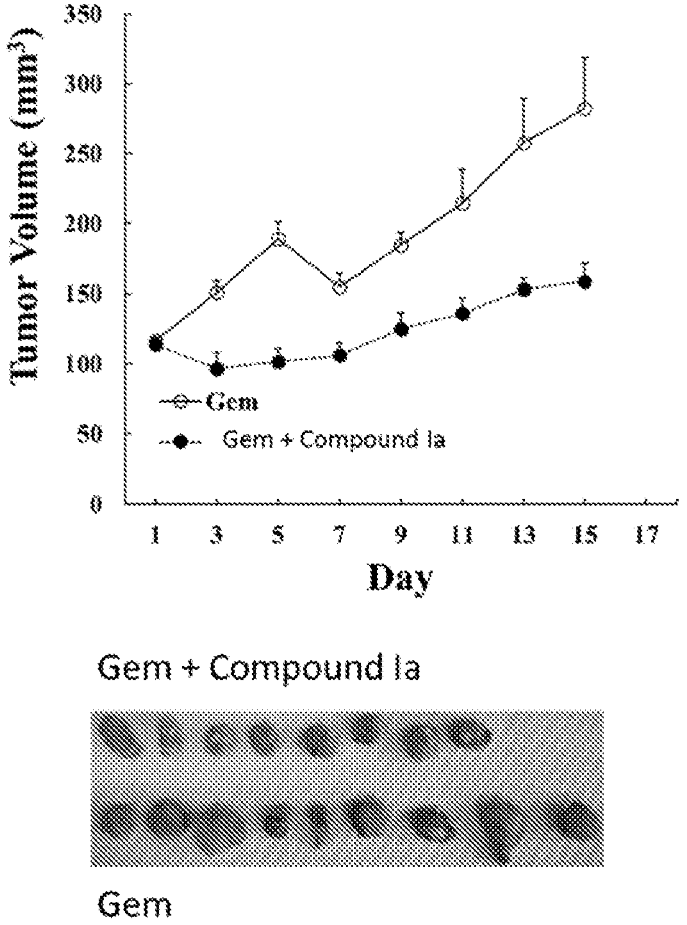
FIG. 7D shows the efficacy of Gemcitabine, alone and in combination with Compound Ia, against tumour volume following intra-tumour injection.

Intra-tumour injection of Compound Ia at 10 mg/kg on day 1, followed by gemcitabine treatment (50 mg/kg) also demonstrated efficacy as observed by decreased tumour volume over 21 days compared to gemcitabine treatment alone, as shown in FIG. 7*d*. From this, it can be concluded that a single dose injection of Compound Ia significantly enhances the anti-cancer effect of Gemcitabine.

Example 7: Effects of Compound Ia on Immunological Biomarkers

The effects of Compound Ia on immunological biomarkers was assessed using syngeneic mouse models of pancreatic cancer.

Single cell suspension was made from tumour tissues isolated from mice treated with either gemcitabine alone or gemcitabine plus PAK227. The cell suspension was incubated with antibodies against CD45, CD4, CD8, B220, PD-L1, PD-1, CD11b and Ly6c, and then subjected to a flow-cytometry machine for cell number counting and percentage calculation.

Figure 8:
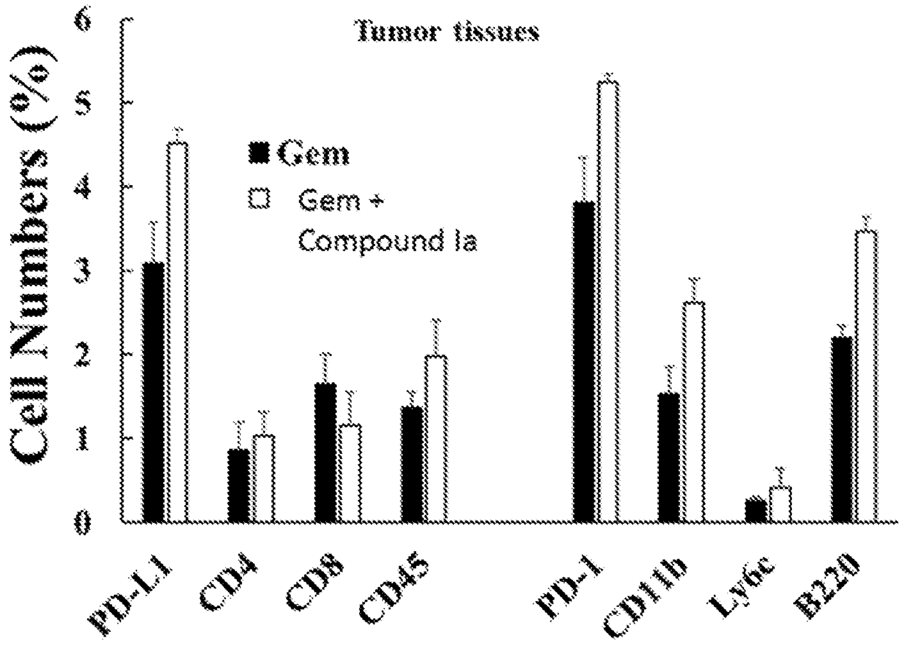
FIG. 8 shows that Compound Ia in combination with Gemcitabine increases various immunological biomarkers.

The results, shown in FIG. 8, demonstrate that Compound Ia in combination with Gemcitabine increases the expression of immunological biomarkers in tumour tissues in comparison to Gemcitabine treatment alone.

Example 8: Prodrug Formulation of Compound Ia

The efficacy of a prodrug formulation of Compound Ia was assessed. The prodrug, Compound Ic, was synthesised and characterised according to Example 3a.

Pancreatic cancer cells (BxPC) were seeded at 5000 cell/100 ul/well in a 96-well plate overnight. The cells were then treated with Compound Ic with concentrations indicated in the figure in the absence of serum for 24 hours. By the end of 24 hour incubation, MTT assay was performed to measure the cell proliferation. The values obtained in control (non-treated) cells were taken as 100%.

Figure 9:
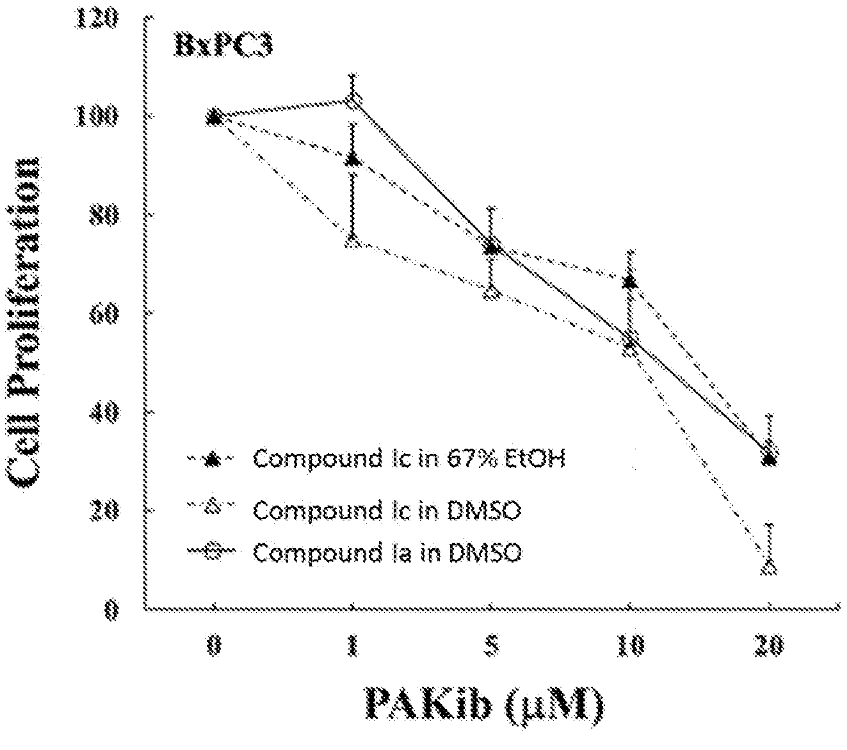
FIG. 9 shows that a prodrug derivative of Compound Ia is able to inhibit pancreatic cell proliferation with a comparable potency to Compound Ia.

The prodrug derivative, Compound Ic, of Compound I is able to be dissolved in a 67% ethanol in water solution, suitable for intraperitoneal, intravenous, and subcutaneous administration. Further, the results, shown in FIG. 9, demonstrate that the prodrug, Compound Ic, of Compound Ia is able to inhibit pancreatic cell proliferation with similar potency to Compound Ia.

REFERENCES

Amro Aboukameel, A. Irfana Muqbil, William Senapedis, Erkan Baloglu, Yosef Landesman, Sharon Shacham, Michael Kauffman, Philip A. Philip, Ramzi M. Mohammad, and Asfar S.
Azmi, Mol. Cancer Ther., 2017, 16(1), 76-87.
Dart A E, Wells C M, Eur J. Cell Biol. 2013: 92:129.
Hakoshima T, Shimizu T, Maesaki R, J. Biochem. 2003; 134:327.

Kimmelman A C, Hezel A F, Aguirre A J, et al, Proc. Natl. Acad. Sci. USA, 2008; 105:19372.
Mehlamaki E H, Kauraniemi P, Monni O et al, Neoplasia, 2004; 6:432.
Murray B W, Guo C, Piraino J, et al, Proc. Natl. Acad. Sci. USA 2010; 107:9446.
Ndubaku, C. O., Crawford, J. J., Drobnick, J., Aliagas, I., Campbell, D., Dong, P., Dornan,
L. M., Duron, S., Epler, J., Gazzard, L., Heise, C. E., Hoeflich, K. P., Jakubiak, D., La, H., Lee, W., Lin, B., Lyssikatos, J. P., Maksimoska, J., Marmorstein, R., Murray, L. J., O'Brien, T., Oh, A., Ramaswamy, S., Wang, W., Zhao, X., Zhong, Y., Blackwood, E., Rudolph, J. Acs Med. Chem. Lett. 2015; 6: 1241-1246.
Rudolph, J., Crawford, J. J., Hoeflich, K. P., Wang, W., J. Med. Chem. 2015; 58: 11-129 Semenova G, Chernoff J. Biochem. Soc. Trans. 2017; 45:79.
Wang, K., Huynh, N., Wang, X., Baldwin, G., Nikfarjam, M., He, H., Int. J. Oncol. 2018; 52:261-269
Yeo D, Huynh N, Beutler J A, et al, Cancer Lett, 2014; 346:264.
Zhang, E. Y., Ha, B. H., Boggon, T. J. (2018) Biochim. Biophys. Acta 1866: 356-365.
Staben, S. T., Feng, J. A., Lyle, K., Belvin, M., Boggs, J., Burch, J. D., Chua, C. C., Cui, H., Dipasquale, A. G., Friedman, L. S., Heise, C., Koeppen, H., Kotey, A., Mintzer, R., Oh, A., Roberts, D. A., Rouge, L., Rudolph, J., Tam, C., Wang, W., Xiao, Y., Young, A., Zhang, Y., Hoeflich, K. P. J. Med. Chem. 2014; 57: 1033-1045.

The invention claimed is:

1. A compound of Formula (I) or a salt thereof:

Formula (I)

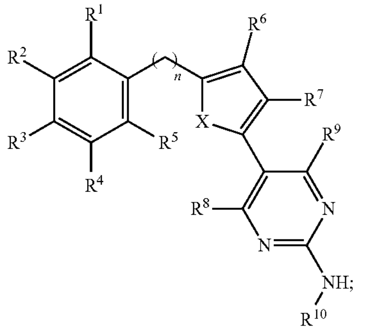

wherein $R^1$ and $R^5$ are each independently selected from the group consisting of halogen and $C_{1-4}$alkyl, wherein $R^3$ is selected from the group consisting of hydrogen, halogen, $C_{1-6}$alkyl, —O—$C_{1-6}$alkyl, $C_{1-6}$haloalkyl, —O—$C_{1-6}$haloalkyl, $C_{2-6}$alkenyl, $C_{2-6}$alkynyl, $C_{3-10}$carbocyclyl, 3-10 membered heterocyclyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$, wherein said alkyl, alkenyl, alkynyl, carbocyclyl or heterocyclyl may be unsubstituted or substituted with one or more substituents each independently selected from the group consisting of halogen, $C_{1-4}$alkyl, O—$C_{1-4}$alkyl, $C_{1-4}$haloalkyl, —O—$C_{1-4}$haloalkyl, —CN, —$OR^{11}$, —$SR^{11}$, —$NR^{11}R^{12}$, —$COR^{11}$, —$CO_2R^{11}$, —$CONR^{11}R^{12}$, —$NR^{11}COR^{12}$, —$SO_2R^{11}$, —$SO_2NR^{11}R^{12}$, and —$NR^{11}SO_2R^{12}$;

$R^2$ and $R^4$ are each independently selected from the group consisting of hydrogen, halogen, $C_{1-4}$alkyl, —O—$C_{1-4}$alkyl, $C_{1-4}$haloalkyl and —O—$C_{1-4}$haloalkyl;

n is an integer of from 0 to 2;

X is S, O, or NH;

$R^6$ is selected from the group consisting of hydrogen, halogen, $C_{1-4}$alkyl, —O—$C_{1-4}$alkyl, $C_{1-4}$haloalkyl and —O—$C_{1-4}$haloalkyl;

$R^7$ is selected from the group consisting of hydrogen, halogen, —CN, —$C_{1-6}$ alkyl, $C_{3-10}$carbocyclyl, $C_{3-10}$heterocyclyl, —O—$C_{1-6}$alkyl, —O—$C_{3-10}$carbocyclyl, —O-(3-10 membered heterocyclyl), —NH($C_{1-6}$alkyl), —N($C_{1-6}$alkyl)$_2$, —NH—$C_{3-10}$carbocyclyl, —N($C_{1-4}$alkyl)-$C_{6-10}$carbocyclyl, —NH-(3-10 membered heterocyclyl), —N($C_{1-4}$alkyl)-(3-10 membered heterocyclyl), —C(O)—$C_{1-4}$alkyl, —C(O)—$C_{3-10}$carbocyclyl, —C(O)-(3-10 membered heterocyclyl), and —C(O)N($C_{1-4}$alkyl)$_2$, wherein said alkyl, carbocyclyl or heterocyclyl may be unsubstituted or substituted with up to two substituents each independently selected from the group consisting of $C_{1-4}$alkyl, oxo, halogen and $C_{1-4}$haloalkyl;

$R^8$ is selected from the group consisting of hydrogen, —$C_{1-8}$alkyl, —O—$C_{1-8}$ alkyl, —$C_{1-4}$alkylene-$R^{13}$, —O—$C_{1-4}$alkylene-$R^{13}$ and —O—$R^{13}$;

$R^9$ is selected from the group consisting of hydrogen and halogen;

$R^{10}$ is selected from the group consisting of hydrogen, $C_{1-6}$alkyl, $C_{1-6}$haloalkyl, $C_{6-10}$aryl, —$R^{14}$, —$C_{1-6}$alkylene-$R^{14}$, —$C_{6-10}$arylene-$R^{14}$, —NH—$C_{1-6}$alkyl-$R^{14}$, and —NH—C(O)—$C_{1-6}$alkyl-$R^{14}$;

wherein said aryl or arylene may optionally be substituted with one or two substituents each independently selected from the group consisting of $C_{1-4}$alkyl, halogen and $C_{1-4}$haloalkyl;

if present, each $R^{11}$ and $R^{12}$ is independently selected from the group consisting of hydrogen, $C_{1-6}$alkyl, $C_{3-10}$carbocyclyl, and 3-10 membered heterocyclyl;

if present, $R^{13}$ is selected from the group consisting of hydrogen, —$C_{1-6}$ alkyl, halogen, —CN, $C_{3-10}$carbocyclyl, 3-10 membered heterocyclyl, —O—$C_{1-6}$alkyl, —O—$C_{3-10}$carbocyclyl, —O-(3-10 membered heterocyclyl), —NH($C_{1-6}$alkyl), —N($C_{1-6}$alkyl)$_2$, —NH—$C_{3-10}$carbocyclyl, —N($C_{1-4}$alkyl)-$C_{6-10}$carbocyclyl, —NH-(3-10 membered heterocyclyl), —N($C_{1-4}$alkyl)-(3-10 membered heterocyclyl), —C(O)—$C_{1-4}$alkyl, —C(O)—$C_{3-10}$carbocyclyl, —C(O)-(3-10 membered heterocyclyl), and —C(O)N($C_{1-4}$alkyl)$_2$, wherein said alkyl, carbocyclyl or heterocyclyl may be unsubstituted or substituted with up to two substituents each independently selected from the group consisting of $C_{1-4}$alkyl, oxo, halogen and $C_{1-4}$haloalkyl; and if present, $R^{14}$ is selected from the group consisting of —$NH_2$, $C_{3-10}$heterocyclyl, —O—$C_{3-10}$heterocyclyl, —NH—$C_{3-10}$heterocyclyl and —N(Me)-$C_{3-10}$heterocyclyl;

wherein said heterocyclyl may be unsubstituted or substituted with up to three substituents each independently selected from $C_{1-4}$alkyl, oxo, halogen and $C_{1-4}$haloalkyl.

2. The compound or salt as claimed in claim 1, wherein $R^3$ is selected from the group consisting of $C_{1-6}$alkyl, —O—$C_{1-6}$alkyl, phenyl, or 5-6 membered heteroaromatic, said phenyl or heteroaromatic being unsubstituted or substituted by one or two $C_{1-4}$ alkyl groups.

3. The compound or salt as claimed in claim 1, wherein $R^2$ and $R^4$ are each hydrogen.

4. The compound or salt as claimed in claim 1, wherein $R^8$ is selected from the group consisting of hydrogen, —$C_{1-4}$alkylene-$R^{13}$, —O—$C_{1-4}$ alkylene-$R^{13}$ and —O—$R^{13}$, and $R^{13}$ is selected from the group consisting of hydrogen, —$C_{1-6}$alkyl, $C_{3-10}$carbocyclyl, —O—$C_{3-10}$carbocyclyl, —NH—$C_{3-10}$carbocyclyl, $C_{3-10}$heterocyclyl, —O—$C_{3-10}$heterocyclyl and —NH—$C_{3-10}$heterocyclyl.

5. The compound or salt as claimed in claim 4, wherein $R^8$ is hydrogen.

6. The compound or salt as claimed in claim 1, wherein $R^9$ is hydrogen.

7. The compound or salt as claimed in claim 1, wherein $R^{10}$ is selected from the group consisting of hydrogen, $C_{1-6}$alkyl, $C_{1-6}$haloalkyl, $C_{6-10}$aryl, —$R^{14}$, —$C_{1-6}$alkylene-$R^{14}$ and —$C_{6-10}$arylene-$R^{14}$, wherein said aryl or arylene may optionally be substituted with one or two substituents each independently selected from the group consisting of $C_{1-4}$alkyl, halogen and $C_{1-4}$haloalkyl.

8. The compound or salt as claimed in claim 1, wherein n is 1.

9. The compound or salt as claimed in claim 1, wherein X is O.

10. The compound or salt as claimed in claim 1, wherein n is 1, X is O, $R^1$ and $R^5$ are chlorine, $R^3$ is —$OCH_3$, and $R^2$ and $R^4$ are each hydrogen.

11. The compound or salt as claimed in claim 1, wherein the compound of Formula (I) is:

(Ia)

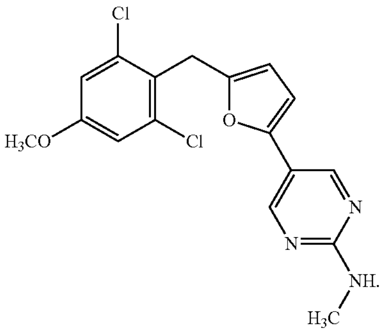

12. The compound or salt as claimed in claim 1, wherein the compound of Formula (I) is:

(Ic)

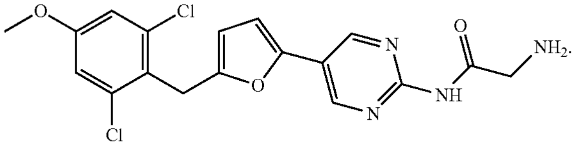

13. The compound or salt as claimed in claim 1, wherein the compound of Formula (I) is:

(Id)

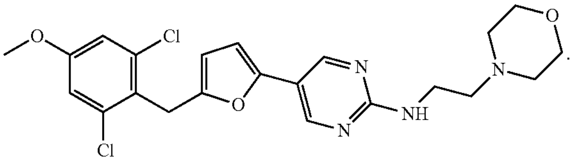

14. The compound or salt as claimed in claim 1, wherein the compound of Formula (I) is:

(Ib)

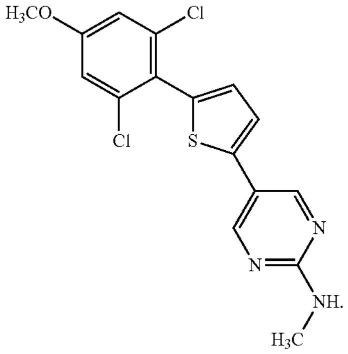

15. A pharmaceutical composition comprising the compound or salt as claimed in claim 1, and a pharmaceutically acceptable excipient.

16. The pharmaceutical composition as claimed in claim 15, further comprising a further therapeutic agent.

17. The pharmaceutical composition as claimed in claim 16, wherein the further therapeutic agent is an anti-cancer agent.

18. The pharmaceutical composition as claimed in claim 15, further comprising a checkpoint inhibitor.

19. The pharmaceutical composition as claimed in claim 18, wherein the checkpoint inhibitor is a CHEK2 inhibitor.

20. A method of immunotherapy, comprising administering an effective amount of the compound or salt as claimed in claim 1 to a subject in need thereof.

* * * * *